US006936442B2

(12) United States Patent
Pichuantes et al.

(10) Patent No.: US 6,936,442 B2
(45) Date of Patent: Aug. 30, 2005

(54) DIAGNOSTIC ASSAYS FOR PARVOVIRUS B19

(75) Inventors: Sergio Pichuantes, El Cerrito, CA (US); Venkatakrishna Shyamala, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/187,253

(22) Filed: Jun. 28, 2002

(65) Prior Publication Data

US 2003/0170612 A1 Sep. 11, 2003

Related U.S. Application Data

(60) Provisional application No. 60/302,077, filed on Jun. 28, 2001, provisional application No. 60/365,956, filed on Mar. 19, 2002, and provisional application No. 60/369,224, filed on Mar. 29, 2002.

(51) Int. Cl.[7] .................................................. C12P 19/34

(52) U.S. Cl. .......................................... 435/91.2; 435/6

(58) Field of Search .................. 435/91.2, 6; 536/23.1, 536/24.1

(56) References Cited

U.S. PATENT DOCUMENTS

| | | | |
|---|---|---|---|
| 5,283,174 A | 2/1994 | Nelson et al. | 435/6 |
| 5,399,491 A | 3/1995 | Kacian et al. | |
| 5,516,630 A | 5/1996 | Ticehurst et al. | |
| 5,538,848 A | 7/1996 | Livak et al. | |
| 5,723,591 A | 3/1998 | Livak et al. | |
| 5,876,930 A | 3/1999 | Livak et al. | |
| 6,154,707 A | 11/2000 | Livak et al. | |
| 6,183,999 B1 | 2/2001 | Weimer et al. | |
| 6,204,044 B1 | 3/2001 | Brown | |
| 6,238,860 B1 | 5/2001 | Whelihan | |
| 6,287,815 B1 | 9/2001 | Brown | |
| 6,294,338 B1 * | 9/2001 | Nunomura | 435/6 |
| 6,642,033 B1 | 11/2003 | Lazo et al. | |

FOREIGN PATENT DOCUMENTS

| | | |
|---|---|---|
| EP | 0 514 413 B1 | 5/1994 |
| EP | 0 491 824 B1 | 5/1995 |
| EP | 0 690 990 B1 | 11/1998 |
| JP | 06293798 A2 | 10/1994 |
| JP | 09010000 A2 | 1/1997 |
| JP | 11225797 A2 | 8/1999 |
| WO | WO 91/12269 A1 | 8/1991 |
| WO | WO 94/10294 A1 | 5/1994 |
| WO | WO 96/09391 A2 | 3/1996 |
| WO | WO 97/21346 A1 | 6/1997 |
| WO | WO 99/18227 A1 | 4/1999 |
| WO | WO 01/06019 A2 | 1/2001 |

OTHER PUBLICATIONS

Shade et al. (GenBank Accession M12178 (GI: 333375), Human parvovirus B19–Au DNA, partial genome).*

Bassam et al. (Australasian Biotechnology, vol. 6, No. 5, Oct. 1996, pp. 285–294).*

Aberham et al. (Journal of Virological Methods 92(2001)183–191).*

Ticehurst, et al., "Hepatitis A Virus (HAV) Peptide Corresponding to the Capsid Protein Region of Poliovirus RNA." Database Geneseq, accession No: AAP50287 sequence alignment with instant SEQ ID NO: 1, Nov. 30, 1991 (Abstract).

Bostic et al., "Quantitative analysis of neutralizing immune responses to human parvovirus B19 using a novel reverse transcriptase–polymerase chain reaction–based assay," *J. Inf. Dis.* 179:619–626, 1999.

Calvet et al., "Parvovirus B19 infection in thoracic organ transplant recipients," *J. Clin. Virol.* 13:37–42, 1999.

Cassinotti et al., "Human parvovirus B19 infections: routine diagnosis by a new nested polymerase chain reaction assay," *J. Med. Virol.* 40:228–234, 1993.

Clewlhy, "Polymerase chain reaction assay of parvovirus B19 DNA in clinical specimens," *J. Clin. Microbiol.* 27:2647–2651, 1989.

Cubie et al., "Synthetic oligonucleotide cocktails as probes for detection of human parvovirus B19," *J. Vir. Meth.* 53:91–102, 1995.

Durigon et al., "Multiple primer pairs for polymerase chain reaction (PCR) amplification of human parvovirus B19 DNA," *J. Vir. Meth.* 44:155–165, 1993.

Fini, "Development of a chemiluminescence competitive PCR for the detection and quantification of parvovirus B19 DNA using a microplate luminometer," *Clin. Chem.* 45:1391–1396, 1999.

Fukada et al. "Four putative subtypes of human parvovirus B19 based on amino acid polymorphism in the C–terminal region of non–structural protein," *J. Med Virol.* 62:60–69, 2000.

Gallinella et al., "Efficient parvovirus B19 DNA purification and molecular cloning," *J. Virol. Meth.* 41:203–211, 1993.

Gruber et al., "Precise quantitation of human parvovirus B19 DNA in biological samples by PCR," *Biologicals* 26:213–216, 1998.

Hicks et al., "A simple and sensitive DNA hybridization assay used for the routine diagnosis of human parvovirus B19 infection," *J. Clin. Microbiol.* 33:2473–2475, 1995.

(Continued)

*Primary Examiner*—Juliet C. Switzer
(74) *Attorney, Agent, or Firm*—Roberta L. Robins; Marcella Lillis; Alisa A. Harbin

(57) ABSTRACT

Human parvovirus B19 primers and probes derived from conserved regions of the parvovirus B19 genome are disclosed. Also disclosed are nucleic acid-based assays using the primers and probes.

20 Claims, 38 Drawing Sheets

OTHER PUBLICATIONS

Holland et al., "Detection of specific polymerase chain reaction product by utilizing the 5' —>3' exonuclease activity of *Thermus aquaticus* DNA polymerase," *PNAS* 88:7276–7280, 1991.

Koch et al., "Detection of human parvovirus B19 DNA by using the polymerase chain reaction," *J. Clin. Microbiol.* 28:65–69, 1990.

Mcomish et al., "Detection of parvovirus B19 in donated blood: a model system for screening by polymerase chain reaction," *J. Clin. Microbiol.* 31:323–328, 1993.

Nelson, "Molecular tools for building nucleic acid IVDS," *IVDT archive*, Mar. 1998 http://devicelink.com/ivdt/archive/98/03/013.html Patou et al., "Characterization of a nested polymerase chain reaction assay for detoction of parvovirus B19," *J. Clin. Microbiol.* 31:540–546, 1993.

Searle et al., "Acute parvovirus B19 infection in pregnant women—an analysis of serial samples by serological and semi–quantitative PCR techniques," *Infection* 26:139–143, 1998.

Shade et al., "Nucleotide sequence and genome organization of human parvovirus B19 isolated from the serum of a child during aplastic crisis," *J. Virol.* 58:921–936, 1986.

Sisk et al., "Expression of human parvovirus B19 structural protein in *E. coli* and detection of antiviral antibodies in human serum," *Biotechnology* 5:1077–1080, 1987.

Takahashi et al., "Genetic heterogeneity of the immunogenic viral capsid protein region of human parvovirus B19 isolates obtained from an outbreak in a pediatric ward," *FEBS Lett.* 450:289–293, 1999.

* cited by examiner

CH47-26 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgttaaaagcatgtggagtgagggggccacttttagtgccaact
ctgtaacttgtacattttccagacagtttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttgtttttttcacctttagagtttcagcatttaattgaaaact
atggaagtatagctcctgatgctttaactgtaaccatatcagaaattgctgttaaggatgttacagacaaaactg
gaggggagtacaagttactgacagcactaccgggcgcctatgcatgttagtagaccatgaatacaagtac
ccatatgtgttagggcaaggtcaggatactttag

FIG. 2A

CH48-29 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaacaatacccaagcatgacttcagttaattctgcagaagccagcac
tggtgcaggagggggtggcagtaatcctgccaaaagcatgtggagtgagggggccacttttactgccaact
ctgtaacttgtacattttccagacagtttttaattccatatgacccagagcaccattataaggtgttttctcccgca
gctagtagctgccacaatgccagtggaaaggaggcaaaggtttgcaccattagtcccataatgggatactca
actccatggagatatttagattttaatgctttaaatttatttttttcacctttagagtttcagcacctaattgaaaattat
ggaagtatagctcctgatgatttaactgtaaccatatcagaaattgctgttaaggatgttacagacaaaactgg
aggggggtacaggttactgacagcactacagggcgcctatgcctgttagtagaccatgaatacaagtacc
catatgtgttagggcaaggtcaggatactttag

FIG. 2B

CH33-2 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaacaatacccaagcatgacttcagttaattctgcagaagccagcac
tggtgcaggaggggggtggcagtaatcctgccaaaagcatgtggagtgaggggggccacttttactgccaact
ctgtaacttgtacattttccagacagtttttaattccatatgacccagagcaccattataaggtgttttctcccgca
gctagtagctgccacaatgccagtggaaaggaggcaaaggtttgcaccattagtcccataatgggatactca
actccatggagatatttagattttaatgctttaaatttatttttttcacctttagagtttcagcacctaattgaaaattat
ggaagtatagctcctgatgatttaactgtaaccatatcagaaattgctgttaaggatgttacagacaaaactgg
aggggggggtacaggttactgacagcactacagggcgcctatgcttgttagtagaccatgaatacaagtacc
catatgtgttagggcaaggtcaggatactttag

FIG. 2C

CH33-3 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaacatacccaagcatgacttcagttaattctgcagaagccagcac
tggtgcaggaggggggtggcagtaatcctgccaaaagcatgtggagtgaggggggccacttttactgccaact
ctgtaacttgtacattttccagacagtttttaattccatatgacccagagcaccattataaggtgttttctcccgca
gctagtagctgccacaatgccagtggaaaggaggcaaaggtttgcaccattagtcccataatgggatactca
actccatggagatatttagattttaatgctttaaatttatttttttcacctttagagtttcagcacctaattgaaaattat
ggaagtatagctcctgatgatttaactgtaaccatatcagaaattgctgttaaggatgttacagacaaaactgg
aggggggggtacaggttactgacagcactacagggcgcctatgcctgttagtagaccatgaatacaagtacc
catatgtgttagggcaaggtcaggatactttag

FIG. 2D

CH33-4 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggtggcagtaatcctgccaaaagcatgtggagtgagggggccacttttactgccaact
ctgtaacttgtacattttccagacagtttttaattccatatgacccagagcaccattataaggtgttttctcccgca
gctagtagctgccacaatgccagtggaaaggaggcaaaggtttgcaccattagtcccataatgggatactca
actccatggagatatttagattttaatgctttaaatttattttttcacctttagagtttcagcacctaattgaaaattat
ggaagtatagctcctgatgatttaactgtaaccatatcagaaattgctgttaaggatgttacagacaaaactgg
agggggggtacaggttactgacagcactacagggcgcctatgcctgttagtagaccatgaatacaagtacc
catatgtgttagggcaaggtcaggatactttag

FIG. 2E

CH42-7 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggggcagtaatcctgtcaaaagcatgtggagtgagggggccacttttagtgccaac
tctgtaacttgtacattttccaggcagtttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacagacaaaact
ggagggggggtacaggttactgacagcactacagggcgcctatgcatgttagtagaccatgaatacaagta
cccatatgtgttagggcaaggtcaggatactttag

FIG. 2F

CH42-18 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgtcaaaagcatgtggagtgagggggccacttttagtgccaac
tctgtaacttgtacattttccagacagtttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacagacaaaact
ggagggggggtgcaggttactgacagcactacagggcgcctatgcatgttagtagaccatgaatacaagta
cccatatgtgttagggcaaggtcaggatactttag

FIG. 2G

CH42-19 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgtcaaaagcatgtggagtgagggggccacttttagtgccaac
tctgtaacttgtacattttccagacagtttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacagacaaaact
ggagggggggtacaggttactgacagcactacagggcgcctatgcatgttagtagaccatgaatacaagta
cccatatgtgttagggcaaggtcaggatactttag

FIG. 2H

CH46-23 ataaatccatatactcattggactgtagcagatgaagagcttttaaaaaatataaaaaatgaaactgggtttcaa
ncacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgtcaaaagcatgtggagtgagggggccacttttagtgccaac
tctgtaacttgtacattttccaggcagtttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacagacaaaact
ggagggggggtacaggttactgacagcactacagggcgcctatgcatgttagtagaccatgaatacaagta
cccatatgtgttagggcaaggtcaggatactttag

FIG. 2I

CH1-1 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgtcaaaagcatgtggagtgagggggccacttttagtgccaac
tctgtaacttgtacattttccagacagtttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacagacaaaact
ggagggggggtacaggttactgacagcactacagggcgcctatgcatgttagtagaccatgaatacaagta
cccatatgtgttagggcaaggtcaggatactttag

FIG. 2J

CH1-6 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtcaaaagcatgtggagtgagggggccacttttagtgccaac
tctgtaacttgtacattttccagacagtttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacagacaaaact
ggaggggggtacaggttactgacagcactacagggcgcctatgcatgttagtagaccatgaatacaagta
cccatatgtgttagggcaaggtcaggatactttag

FIG. 2K

CH2-8 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacagacaaaactg
gaggggggtgcaggttactgacagcactacagggcgcctatgcatgttagtagaccatgaatataagtac
ccatatgtgttagggcaaggtcaggatactttag

FIG. 2L

CH2-10 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacagacagaactg
gaggggggggtgcaggttactgacagcactacagggcgcctatgcatgttagtagaccatgaatataagtac
ccatatgtgttagggcaaggtcaggatactttag

FIG. 2M

H2-11C ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacagacaaaactg
gaggggggggtgcaggttactgacagcactacagggcgcctatgcatgttagtagaccatgaatataagtac
ccatatgtgttagggcaaggtcaggatactttag

FIG. 2N

CH5-13 ctaaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgttaaaagcatgtggagtgagggggccacttttagtgccaact
ctgtaacttgtacattttccagacagtttttaattccatatgacccagagcaccattataaggtgttttctcccgca
gcaagtagctgccacaatgccagtggaaaagaggcaaaggtttgcactattagtcccataatgggatactca
accccatggagatatttagattttaatgctttaaatttattttttcacctttagagtttcagcacttaattgaaaattat
ggcagtatagctcctgatgctttaactgtaaccatatcagaaattgctgttaaggatgttacagacaaaactgg
agggggggtacaggttactgacagcactacagggcgcctatgcatgttagtagaccatgaatacaagtacc
caatgtgttagggcaaggtcaggatactttag

FIG. 2O

CH7-22 ataaatccatgtactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgttaaaagcatgtggagtgagggggccacttttagtgccaact
ctgtaacttgtacattttccagacagtttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttgttttttcacctttagagtttcagcatttaattgaaaact
atggaagtatagctcctgatgctttaactgtaaccatatcagaaattgctgttaaggatgttacagacaaaactg
gagggggagtacaagttactgacagcactaccgggcgcctatgcatgttagtagaccatgaatacaagtac
ccatatgtgttagggcaaggtcaggatactttag

FIG. 2P

CH13-27 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaattctgtcaaaagcatgtggagtgagggggccacttttagtgctaact
ctgtaacttgtacattttccagacagtttttaattccatatgacccagagcaccattataaggtgttttctcccgca
gcgagtagctgccacaatgccagtggaaaggaggcaaaggtttgcaccatcagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacagacaaaactg
gaggggggggtacaggttactgacagcactacagggcgcctatgcatgttagtagaccatgaatacaagtac
ccatatgtgttagggcaaggtcaggatactttag

FIG. 2Q

CH14-33 ataaatccatatactcattggactgtggcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggagtaatcctgttaaaagcatgtggagtgagggggccacttttagtgccaactc
tgtaacttgtacattttccagacagtttttaattccatatgacccagagcaccattataaggtgttttctcccgcag
caagtagctgccacaatgccagtggaaaagaggcaaaggtttgcaccattagtcccataatgggatactcaa
ccccatggagatatttagattttaatgctttaaatttattttttcacctttagagtttcagcacttaattgaaaattatg
gtagtatagctcctgatgctttaactgtaaccatatcagaaattgctgttaaagatgttacagacaaaactggag
gggggtacaggttactgacagcactacagggcgcctatgcatgttagtggaccatgaatacaagtaccca
tatgtgttagggcaaggtcaggatactttag

FIG. 2R

CH62-2 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcaattaattctgcagaagccagcact
ggtgcaggagggggggcagtaatcctgtcaaaagcatgtggagtgagggggccacttttagtgccaact
ctgtaacttgtacakttccagacagtttttaattccatatgacccagagcaccattataaggtgttttctcccgca
gccagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacagacaaaactg
gaggggggtacaggttactgacagcactacaggccgcctatgcatgttagtagaccatgaatacaagtac
ccatatgtgttagggcaaggtcaggatactttag

FIG. 2S

CH64-2 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgttaaaagcatgtggagtgagggggccacttttagtgccaact
ctgtaacttgtacattttccagacagtttttaattccatatgacccagagcaccattataaggtgttttcgcccgca
gcaagtagctgccacaatgccagtggaaaggaggcaaaggtttgcaccattagtcccataatgggatactc
aaccccatggagatacttagattttaatgctttaaatttattttttcacctttagagtttcagcacttaattgaaaatt
atggaagtatagctcctgatgctttaactgtaaccatatcagaaattgctgttaaggatgttacggacaaaactg
gaggggggtgcaggttactgacagcactacagggcgcctatgcatgttagtagaccatgaatacaagtac
ccatatgtgttagggcaaggtcaggatactttag

FIG. 2T

CH67-2 ataaatccatatactcattggactgtggcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggggagtaatcctgttaaaagcatgtggagtgagggggccacttttagtgccaact
ctgtaacttgtacattttccagacagtttttaattccatatgacccagagcaccattataaggtgttttctcccgca
gcaagtagctgccacaatgccagtggaaaagaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaagatgttacagacaaaactg
gagggggggtacaggttactgacagcactacagggcgcctatgcatgttagtggaccatgaatacaagtac
ccatatgtgttagggcaaggtcaggatactttag

FIG. 2U

Parvovirus B19 clone #2-B1

1 cccgccttat gcaaatgggc agccatctta agtgttttac tataatttta ttggtcagtt
61 ttgtaacggt taaaatgggc ggagcgtagg caaggactac agtatatata gcacagcact
121 gccgcagctc tttctttctg ggctgctttt ttcctggact tacttgctgt tttttgtgag
181 ctaactaaca ggtatttata ctacttgtta acatactaac atggagctat ttagaggggt
241 gcttcaagtt tcttctaatg ttctggactg tgctaacgat aactggtggt gctctttact
301 ggatttagac acttctgact gggaaccact aactcatact aacagactaa tggcaatata
361 cttaagcagt gtggcttcta agcttgactt tactgggggg ccactagcag ggtgcttgta
421 ctttttcaa gtagaatgta acaaatttga agaaggctat catattcatg tggttattgg
481 ggggccaggg ttaaacccca gaaacctcac agtgtgtgta gaggggttat ttaataatgt
541 actttatcac cttgtaactg aaaatctgaa gctaaaattt ttgccaggaa tgactacaaa
601 aggcaaatac tttagagatg gagagcagtt tatagaaaac tatttaatga aaaaaatacc
661 tttaaatgtt gtatggtgtg ttactaatat tgatggacat atagatacct gtatttctgc
721 tacttttaga aagggagctt gccatgccaa gaaaccccgc atcaccacag ccataaatga
781 tactagtact gatgctgggg agtctagcgg cacaggggca gaggttgtgc catttaatgg
841 gaagggaact aaggctagca taaagtttca aactatggta aactggttgt gtgaaaacag
901 agtgtttaca gaggataagt ggaaactagt tgactttaac cagtacactt tactaagcag
961 tagtcacagt ggaagttttc aaattcaaag tgcactaaaa ctagcaattt ataaagcaac
1021 taatttagtg cctactagca catttttatt gcatacagac tttgagcaag ttatgtgtat
1081 taaaaacaat aaaattgtta aattgttact ttgtcaaaac tatgaccccc tattagtggg
1141 gcagcatgtg ttaaagtgga ttgataaaaa atgtggcaag aaaaacacac tgtggtttta
1201 tgggccgcca agtacaggga aaacaaactt ggcaatggcc attgctaaaa gtgttccagt
1261 atatggcatg gttaactgga ataatgaaaa ctttccattt aatgatgtag caggaaaaag
1321 cttggtggtc tgggatgaag gtattattaa gtctacaatt gtagaagctg caaaagccat
1381 tttaggcggg caacccacca gggtagatca aaaaatgcgt ggaagtgtag ctgtgcctgg
1441 agtacctgtg gttataacca gcaatggtga cattactttt gttgtaagcg ggaacactac
1501 aacaactgta catgctaaag ccttaaaaga gcgcatggta aagttaaact ttactgtaag
1561 atgcagccct gacatggggt tactaacaga ggctgatgta caacagtggc ttacatggtg
1621 taatgcacaa agctgggacc actatgaaaa ctgggcaata aactacactt ttgatttccc
1681 tggaattaat gcagatgccc tccacccaga cctccaaacc accccaattg tcacagacac
1741 cagtatcagc agcagtggtg gtgaaagctc tgaagaactc agtgaaagca gcttttttaa
1801 cctcatcacc ccaggcgcct ggaacactga aaccccgcgc tctagtacgc ccatccccgg
1861 gaccagttca ggagaatcat ctgtcggaag cccagtttcc tccgaagttg tagctgcatc
1921 gtgggaagaa gccttctaca cacctttggc agaccagttt cgtgaactgt tagttggggt
1981 tgattatgtg tgggacggtg taaggggttt acctgtctgt tgtgtgcaac atattaacaa

FIG. 3A 2041 tagtggggga ggcttgggac tttgtcccca ttgcattaat gtaggggctt ggtataatgg
2101 atggaaattt cgagaattta ccccagattt ggtgcgatgt agctgccatg tgggagcttc
2161 taatcccttt tctgtgctaa cctgcaaaaa atgtgcttac ctgtctggat tgcaaagctt
2221 tgtagattat gagtaaagaa agtggcaaat ggtgggaaag tgatgataaa tttgctaaag
2281 ctgtgtatca gcaatttgtg gaattttatg aaaaggttac tggaacagac ttagagctta
2341 ttcaaatatt aaaagatcat tataatattt ctttagataa tcccctagaa aacccatcct
2401 ctttgtttga cttagttgct cgtattaaaa ataaccttaa aaactctcca gacttatata
2461 gtcatcattt tcaaagtcat ggacagttat ctgaccaccc ccatgcctta tcatccagta
2521 gcagtcatgc agaacctaga ggagaagatg cagtattatc tagtgaagac ttacacaagc
2581 ctgggcaagt tagcgtacaa ctacccggta ctaactatgt tgggcctggc aatgagctac
2641 aagctgggcc cccgcaaagt gctgttgaca gtgctgcaag gattcatgac tttaggtata
2701 gccaactggc taagttggga ataaatccat atactcattg gactgtagca gatgaagagc
2761 ttttaaaaaa tataaaaaat gaaactgggt ttcaagcaca agtagtaaaa gactacttta
2821 ctttaaaagg tgcagctgcc cctgtggccc attttcaagg aagtttgccg gaagttcccg
2881 cttacaacgc ctcagaaaaa tacccaagca tgacttcagt taattctgca gaagccagca
2941 ctggtgcagg aggggggggc agtaatcctg tgaaaagcat gtggagtgag gggggccactt
3001 ttagtgccaa ctctgtaact tgtacatttt ccagacaatt tttaattcca tatgacccag
3061 agcaccatta taaggtgttt tctcccgcag caagtagctg ccacaatgcc agtggaaagg
3121 aggcaaaggt ttgcaccatt agtcccataa tgggatactc aaccccatgg agatatttag
3181 attttaatgc tttaaattta ttttttcac ctttagagtt tcagcactta attgaaaatt
3241 atggaagtat agctcctgat gctttaactg taaccatatc agaaattgct gttaaggatg
3301 ttacggacaa aactggaggg ggggtgcagg ttactgacag cactacaggg cgcctatgca
3361 tgttagtaga ccatgaatat aagtacccat atgtgttagg gcaaggtcaa gatactttag
3421 ccccagaact tcctatttgg gtatactttc cccctcaata cgcttactta acagtaggag
3481 atgttaacac acaaggaatt tctggagaca gcaaaaaatt ggcaagtgaa gaatcagcat
3541 tttatgtttt ggaacacagt tcttttcagc ttttaggtac aggaggtaca gcaactatgt
3601 cttataagtt tcctccagtg cccccagaaa atttagaggg ctgcagtcaa cacttttatg
3661 aaatgtacaa ccccttatac ggatcccgct taggggttcc tgacacatta ggaggtgacc
3721 caaaatttag atctttaaca catgaagacc atgcaattca gccccaaaac ttcatgccag
3781 ggccactagt aaactcagtg tctacaaagg agggagacag ctctagtact ggagctggaa
3841 aagccttaac aggccttagc acaggtacct ctcaaaacac tagaatatcc ttacgccctg
3901 ggccagtgtc tcagccgtac caccactggg acacagataa atatgtcaca ggaataaatg
3961 ccatttctca tggtcagacc acttatggta acgctgaaga caaagagtat cagcaaggag
4021 tgggtagatt tccaaatgaa aaagaacagc taaaacagtt acagggttta aacatgcaca
4081 cctactttcc caataaagga acccagcaat atacagatca aattgagcgc cccctaatgg
4141 tgggttctgt atggaacaga agagcccttc actatgaaag ccagctgtgg agtaaaattc
4201 caaatttaga tgacagtttt aaaactcagt ttgcagcctt aggaggatgg ggtttgcatc

FIG. 3B 4261 agccacctcc tcaaatattt ttaaaaatat taccacaaag tgggccaatt ggaggtatta
4321 aatcaatggg aattactacc ttagttcagt atgccgtggg aattatgaca gtaaccatga
4381 catttaaatt ggggccccgt aaagctacgg gacggtggaa tcctcaacct ggagtgtatc
4441 ccccgcacgc agcaggtcat ttaccatatg tactatatga ccccacagct acagatgcaa
4501 aacaacacca cagacatgga tatgaaaagc ctgaagaatt gtggacagcc aaaagccgtg
4561 tgcacccatt gtaaacactc cccaccgtgc cctcagccag gatgtgtaac taaacgccca
4621 ccagtaccac ccagactgta cctgccccct cctataccta taagacagcc taacacaa

FIG. 3C

Parvovirus B19 clone #2-B6

1 cccgccttat gcaaatgggc agccatctta agtgttttac tataatttta ttggtcagtt
61 ttgtaacggt taaaatgggc ggagcgtagg caaggactac agtatatata gcacagcact
121 gccgcagctc tttctttctg ggctgctttt ttcctggact tacttgctgt tttttgtgag
181 ctaactaaca ggtatttata ctacttgtta acatactaac atggagctat ttagaggggt
241 gcttcaagtt tcttctaatg ttctggactg tgctaacgat aactggtggt gctctttact
301 ggatttagac acttctgact gggaaccact aactcatact aacagactaa tggcaatata
361 cttaagcagt gtggcttcta agcttgactt tactgggggg ccactagcag ggtgcttgta
421 ctttttcaa gtagaatgta acaaatttga agaaggctat catattcatg tggttattgg
481 ggggccaggg ttaaacccca gaaacctcac agtgtgtgta gaggggttat ttaataatgt
541 actttatcac cttgtaactg aaaatctgaa gctaaaattt ttgccaggaa tgactacaaa
601 aggcaaatac tttagagatg gagagcagtt tatagaaaac tatttaatga aaaaaatacc
661 tttaaatgtt gtatggtgtg ttactaatat tgatggacat atagatacct gtatttctgc
721 tacttttaga aagggagctt gccatgccaa gaaaccccgc atcaccacag ccataaatga
781 tactagtact gatgctgggg agtctagcgg cacaggggca gaggttgtgc catttaatgg
841 gaagggaact aaggctagca taaagtttca aactatggta aactggttgt gtgaaaacag
901 agtgtttaca gaggataagt ggaaactagt tgactttaac cagtacactt tactaagcag
961 tagtcacagt ggaagttttc aaattcaaag tgcactaaaa ctagcaattt ataaagcaac
1021 taatttagtg cctactagca catttttatt gcatacagac tttgagcaag ttatgtgtat
1081 taaagacaat aaaattgtta aattgttact ttgtcaaaac tatgaccccc tattagtggg
1141 gcagcatgtg ttaaagtgga ttgataaaaa atgtggcaag aaaaacacac tgtggtttta
1201 tggaccgcca agtacaggga aaacaaactt ggcaatggcc attgctaaaa gtgttccagt
1261 atatggcatg gttaactgga ataatgaaaa ctttccattt aatgatgtag caggaaaaag
1321 cttggtggtc tgggatgaag gtattattaa gtctacaatt gtagaagctg caaaagccat
1381 tttaggcggg caacccacca gggtagatca aaaaatgcgt ggaagtgtag ctgtgcctgg
1441 agtacccgtg gttataacca gcaatggtga cattactttt gttgtaagcg ggaacactac
1501 aacaactgta catgctaaag ccttaaaaga gcgcatggta aagttaaact ttactgtaag
1561 atgcagccct gacatggggt tactaacaga ggctgatgta caacagtggc ttacatggtg
1621 taatgcacaa agctgggacc actatgaaaa ctgggcaata aactacactt ttgatttccc
1681 tggaattaat gcagatgccc tccacccaga cctccaaacc accccaattg tcacagacac
1741 cagtatcagc agcagtggtg gtgaaagctc tgaagaactc agtgaaagca gcttttttaa
1801 cctcatcacc ccaggcgcct ggaacactga aaccccgcgc tctagtacgc ccatccccgg
1861 gaccagttca ggagaatcat ctgtcggaag cccagtttcc tccgaagttg tagctgcatc
1921 gtgggaagaa gccttctaca cacctttggc agaccagttt cgtgaactgt tagttggggt
1981 tgattatgtg tgggacggtg taaggggttt acctgtctgt tgtgtgcaac atattaacaa
2041 tagtggggga ggcttgggac tttgtcccca ttgcattaat gtaggggctt ggtataatgg

FIG. 4A

```
2101 atggaaattt cgagaattta ccccagattt ggtgcgatgt agctgccatg tgggagcttc
2161 taatcccttt tctgtgctaa cctgcaaaaa atgtgcttac ctgtctggat tgcaaagctt
2221 tgtagattat gagtaaagaa agtggcaaat ggtgggaaag tgatgataaa tttgctaaag
2281 ctgtgtatca gcaatttgtg gaattttatg aaaaggttac tggaacagac ttagagctta
2341 ttcaaatatt aaaagatcat tataatattt ctttagataa tcccctagaa aacccatcct
2401 ctttgtttga cttagttgct cgtattaaaa ataaccttaa aaactctcca gacttatata
2461 gtcatcattt tcaaagtcat ggacagttat ctgaccaccc ccatgcctta tcatccagta
2521 gcagtcatgc agaacctaga ggagaagatg cagtattatc tagtgaagac ttacacaagc
2581 ctgggcaagt tagcgtacaa ctacccggta ctaactatgt tgggcctggc aatgagctac
2641 aagctgggcc cccgcaaagt gctgttgaca gtgctgcaag gattcatgac tttaggtata
2701 gccaactggc taagttggga ataaatccat atactcattg gactgtagca gatgaagagc
2761 ttttaaaaaa tataaaaaat gaaactgggt ttcaagcaca agtagtaaaa gactacttta
2821 ctttaaaagg tgcagctgcc cctgtggccc attttcaagg aagtttgccg gaagttcccg
2881 cttacaacgc ctcagaaaaa tacccaagca tgacttcagt taattctgca gaagccagca
2941 ctggtgcagg aggggggggc agtaatcctg tgaaaagcat gtggagtgag ggggccactt
3001 ttagtgccaa ctctgtaact tgtacatttt ccagacaatt tttaattcca tatgacccag
3061 agcaccatta taaggtgttt tctcccgcag caagtagctg ccacaatgcc agtggaaagg
3121 aggcaaaggt ttgcaccatt agtcccataa tgggatactc aaccccatgg agatatttag
3181 attttaatgc tttaaattta tttttttcac ctttagagtt tcagcactta attgaaaatt
3241 atggaagtat agctcctgat gctttaactg taaccatatc agaaattgct gttaaggatg
3301 ttacaaacaa aactggaggg ggggtgcagg ttactgacag cactacaggg cgcctatgca
3361 tgttagtaga ccatgaatat aagtacccat atgtgttagg gcaaggtcaa gatactttag
3421 ccccagaact tcctatttgg gtatactttc cccctcaata cgcttactta acagtaggag
3481 atgttaacac acaaggaatt tctggagaca gcaaaaaatt ggcaagtgaa gaatcagcat
3541 tttatgtttt ggaacacagt tcttttcagc ttttaggtac aggaggtaca gcaactatgt
3601 cttataagtt tcctccagtg cccccagaaa atttagaggg ctgcagtcaa cacttttatg
3661 aaatgtacaa ccccttatac ggatcccgct taggggttcc tgacacatta ggaggtgacc
3721 caaaatttag atctttaaca catgaagacc atgcaattca gccccaaaac ttcatgccag
3781 ggccactagt aaactcagtg tctacaaagg agggagacag ctctagtact ggagctggaa
3841 aagccttaac aggccttagc acaggtacct ctcaaaacac tagaatatcc ttacgccctg
3901 ggccagtgtc tcagccgtac caccactggg acacagataa atatgtcaca ggaataaatg
3961 ccatttctca tggtcagacc acttatggta acgctgaaga caaagagtat cagcaaggag
4021 tgggtagatt tccaaatgaa aaagaacagc taaaacagtt acagggttta aacatgcaca
4081 cctactttcc caataaagga acccagcaat atacagatca aattgagcgc cccctaatgg
4141 tgggttctgt atggaacaga gagcccttc actatgaaag ccagctgtgg agtaaaattc
4201 caaatttaga tgacagtttt aaaactcagt ttgcagcctt aggaggatgg ggtttgcatc
4261 agccacctcc tcaaatattt ttaaaaatat taccacaaag tgggccaatt ggaggtatta
```

FIG. 4B 4321 aatcaatggg aattactacc ttagttcagt atgccgtggg aattatgaca gtaaccatga
4381 catttaaatt ggggccccgt aaagctacgg gacggtggaa tcctcaacct ggagtgtatc
4441 ccccgcacgc agcaggtcat ttaccatatg tactatatga ccccacagct acagatgcaa
4501 aacaacacca cagacatgga tatgaaaagc ctgaagaatt gtggacagcc aaaagccgtg
4561 tgcacccatt gtaaacactc cccaccgtgc cctcagccag gatgtgtaac taaacgccca
4621 ccagtaccac ccagactgta cctgccccct cctataccta taagacagcc taacacaa

FIG. 4C

Clone B1-NS1 single stranded DNA sequence:

atactcttcgaacaaaacaaaatggagctatttagaggggtgcttcaagtttcttctaatgttctggactgtgctaacgataactggtggtgctctt
tactggatttagacacttctgactgggaaccactaactcatactaacagactaatggcaatatacttaagcagtgtggcttctaagcttgacttta
ctggggggccactagcagggtgcttgtactttttcaagtagaatgtaacaaatttgaagaaggctatcatattcatgtggttattgggggcca
gggttaaaccccagaaacctcacagtgtgtgtagaggggttatttaataatgtactttatcaccttgtaactgaaaatctgaagctaaaatttttgc
caggaatgactacaaaaggcaaatactttagagatggagagcagtttatagaaaactatttaatgaaaaaaatacctttaaatgttgtatggtgt
gttactaatattgatggacatatagatacctgtatttctgctacttttagaaagggagcttgccatgccaagaaaccccgcatcaccacagccat
aaatgatactagtactgatgctggggagtctagcggcacaggggcagaggttgtgccatttaatgggaagggaactaaggctagcataaag
tttcaaactatggtaaactggttgtgtgaaaacagagtgtttacagaggataagtggaaactagttgactttaaccagtacactttactaagcagt
agtcacagtggaagttttcaaattcaaagtgcactaaaactagcaatttataaagcaactaatttagtgcctactagcacatttttattgcatacag
actttgagcaagttatgtgtattaaaaacaataaaattgttaaattgttactttgtcaaaactatgacccccctattagtggggcagcatgtgttaaag
tggattgataaaaaatgtggcaagaaaaacacactgtggttttatgggccgccaagtacagggaaaacaaacttggcaatggccattgctaa
aagtgttccagtatatggcatggttaactggaataatgaaaactttccatttaatgatgtagcaggaaaaagcttggtggtctgggatgaag
gtattattaagtctacaattgtagaagctgcaaaagccattttaggcgggcaacccaccagggtagatcaaaaaatgcgtggaagtgtagctg
tgcctggagtacctgtggttataaccagcaatggtgacattacttttgttgtaagcgggaacactacaacaactgtacatgctaaagccttaaaa
gagcgcatggtaaagttaaactttactgtaagatgcagccctgacatggggttactaacagaggctgatgtacaacagtggcttacatggtgt
aatgcacaaagctgggaccactatgaaaactgggcaataaactacacttttgatttccctggaattaatgcagatgccctccacccagacctcc
aaaccaccccaattgtcacagacaccagtatcagcagcagtggtggtgaaagctctgaagaactcagtgaaagcagctttttttaacctcatca
ccccaggcgcctggaacactgaaaccccgcgctctagtacgcccatccccgggaccagttcaggagaatcatctgtcggaagcccagtttc
ctccgaagttgtagctgcatcgtgggaagaagccttctacacacctttggcagaccagtttcgtgaactgttagttggggttgattatgtgtggg
acggtgtaaggggtttacctgtctgttgtgtgcaacatattaacaatagtgggggaggcttgggactttgtccccattgcattaatgtaggggct
tggtataatggatggaaatttcgagaatttaccccagatttggtgcgatgtagctgccatgtgggagcttctaatcccttttctgtgctaacctgca
aaaaatgtgcttacctgtctggattgcaaagctttgtagattatgagtaagtcgacatactc

FIG. 5A

Clone B1 NS1 amino acid sequence:

MELFRGVLQVSSNVLDCANDNWWCSLLDLDTSDWEPLTHTNRLMAIYLSSVAS
KLDFTGGPLAGCLYFFQVECNKFEEGYHIHVVIGGPGLNPRNLTVCVEGLFNNVLYHLVT
ENLKLKFLPGMTTKGKYFRDGEQFIENYLMKKIPLNVVWCVTNIDGHIDTCISATFRKGA
CHAKKPRITTAINDTSTDAGESSGTGAEVVPFNGKGTKASIKFQTMVNWLCENRVFTEDK
WKLVDFNQYTLLSSSHSGSFQIQSALKLAIYKATNLVPTSTFLLHTDFEQVMCIKNNKIV
KLLLCQNYDPLLVGQHVLKWIDKKCGKKNTLWFYGPPSTGKTNLAMAIAKSVPVYGMVNW
NNENFPFNDVAGKSLVVWDEGIIKSTIVEAAKAILGGQPTRVDQKMRGSVAVPGVPVVIT
SNGDITFVVSGNTTTTVHAKALKERMVKLNFTVRCSPDMGLLTEADVQQWLTWCNAQSWD
HYENWAINYTFDFPGINADALHPDLQTTPIVTDTSISSSGGESSEELSESSFFNLITPGA
WNTETPRSSTPIPGTSSGESSVGSPVSSEVVAASWEEAFYTPLADQFRELLVGVDYVWDG
VRGLPVCCVQHINNSGGGLGLCPHCINVGAWYNGWKFREFTPDLVRCSCHVGASNPFSVL
TCKKCAYLSGLQSFVDYE

FIG. 5B

B1 VP1 single stranded DNA sequence:

atactcaagcttacaaaacaaaatgagtaaagaaagtggcaaatggtgggaaagtgatgataaatttgctaaagctgtgtatcagcaatttgtg
gaattttatgaaaaggttactggaacagacttagagcttattcaaatattaaaagatcattataatatttctttagataatcccctagaaaacccatc
ctctttgtttgacttagttgctcgtattaaaaataaccttaaaaactctccagacttatatagtcatcattttcaaagtcatggacagttatctgaccac
ccccatgccttatcatccagtagcagtcatgcagaacctagaggagaagatgcagtattatctagtgaagacttacacaagcctgggcaagtt
agcgtacaactacccggtactaactatgttgggcctggcaatgagctacaagctgggcccccgcaaagtgctgttgacagtgctgcaaggat
tcatgactttaggtatagccaactggctaagttgggaataaatccatatactcattggactgtagcagatgaagagcttttaaaaaatataaaaaa
tgaaactgggtttcaagcacaagtagtaaaagactactttactttaaaaggtgcagctgcccctgtggcccattttcaaggaagtttgccggaag
ttcccgcttacaacgcctcagaaaaatacccaagcatgacttcagttaattctgcagaagccagcactggtgcaggagggggggcagtaat
cctgtgaaaagcatgtggagtgagggggccacttttagtgccaactctgtaacttgtacattttccagacaatttttaattccatatgacccagag
caccattataaggtgttttctcccgcagcaagtagctgccacaatgccagtggaaaggaggcaaaggtttgcaccattagtcccataatgggat
actcaaccccatggagatatttagattttaatgctttaaatttattttttcacctttagagtttcagcacttaattgaaaattatggaagtatagctcct
gatgctttaactgtaaccatatcagaaattgctgttaaggatgttacggacaaaactggagggggggtgcaggttactgacagcactacag
ggcgcctatgcatgttagtagaccatgaatataagtacccatatgtgttagggcaaggtcaagatactttagccccagaacttcctatttgggtat
actttccccctcaatacgcttacttaacagtaggagatgttaacacacaaggaatttctggagacagcaaaaaattggcaagtgaagaatcagc
attttatgttttggaacacagttcttttcagcttttaggtacaggaggtacagcaactatgtcttataagtttcctccagtgcccccagaaaatttaga
gggctgcagtcaacacttttatgaaatgtacaaccccttatacggatcccgcttaggggttcctgacacattaggaggtgacccaaaatttagat
ctttaacacatgaagaccatgcaattcagccccaaaacttcatgccagggccactagtaaactcagtgtctacaaaggagggagacagctcta
gtactggagctggaaaagccttaacaggccttagcacaggtacctctcaaaacactagaatatccttacgccctgggccagtgtctcagccgt
accaccactgggacacagataaatatgtcacaggaataaatgccatttctcatggtcagaccacttatggtaacgctgaagacaaagagtatc
agcaaggagtgggtagatttccaaatgaaaaagaacagctaaaacagttacagggtttaaacatgcacacctactttcccaataaaggaaccc
agcaatatacagatcaaattgagcgcccccctaatggtgggttctgtatggaacagaagagcccttcactatgaaagccagctgtggagtaaaa
ttccaaatttagatgacagttttaaaactcagtttgcagccttaggaggatggggtttgcatcagccacctcctcaaatatttttaaaaatattacca
caaagtgggccaattggaggtattaaatcaatgggaattactaccttagttcagtatgccgtgggaattatgacagtaaccatgacatttaaattg
gggccccgtaaagctacgggacggtggaatcctcaacctggagtgtatcccccgcacgcagcaggtcatttaccatatgtactatatgaccc
cacagctacagatgcaaaacaacaccacagacatggatatgaaaagcctgaagaattgtggacagccaaaagccgtgtgcacccattgtaa
gtcgacatactc

FIG. 6A

B1 VP1 amino acid sequence:

MSKESGKWWESDDKFAKAVYQQFVEFYEKVTGTDLELIQILKDHYNISLDNPL
ENPSSLFDLVARIKNNLKNSPDLYSHHFQSHGQLSDHPHALSSSSSHAEPRGEDAVLSSE
DLHKPGQVSVQLPGTNYVGPGNELQAGPPQSAVDSAARIHDFRYSQLAKLGINPYTHWTV
ADEELLKNIKNETGFQAQVVKDYFTLKGAAAPVAHFQGSLPEVPAYNASEKYPSMTSVNS
AEASTGAGGGGSNPVKSMWSEGATFSANSVTCTFSRQFLIPYDPEHHYKVFSPAASSCHN
ASGKEAKVCTISPIMGYSTPWRYLDFNALNLFFSPLEFQHLIENYGSIAPDALTVTISEI
AVKDVTDKTGGGVQVTDSTTGRLCMLVDHEYKYPYVLGQGQDTLAPELPIWVYFPPQYAY
LTVGDVNTQGISGDSKKLASEESAFYVLEHSSFQLLGTGGTATMSYKFPPVPPENLEGCS
QHFYEMYNPLYGSRLGVPDTLGGDPKFRSLTHEDHAIQPQNFMPGPLVNSVSTKEGDSSS
TGAGKALTGLSTGTSQNTRISLRPGPVSQPYHHWDTDKYVTGINAISHGQTTYGNAEDKE
YQQGVGRFPNEKEQLKQLQGLNMHTYFPNKGTQQYTDQIERPLMVGSVWNRRALHYESQL
WSKIPNLDDSFKTQFAALGGWGLHQPPPQIFLKILPQSGPIGGIKSMGITTLVQYAVGIM
TVTMTFKLGPRKATGRWNPQPGVYPPHAAGHLPYVLYDPTATDAKQHHRHGYEKPEELWT
AKSRVHPL

FIG. 6B

B1 VP2 single stranded DNA sequence:

atactcaagcttacaaaacaaaatgacttcagttaattctgcagaagccagcactggtgcaggagggggggcagtaatcctgtgaaaagca
tgtggagtgagggggccacttttagtgccaactctgtaacttgtacattttccagacaatttttaattccatatgacccagagcaccattataaggt
gttttctcccgcagcaagtagctgccacaatgccagtggaaaggaggcaaaggtttgcaccattagtcccataatgggatactcaaccccatg
gagatatttagattttaatgctttaaatttattttttcacctttagagtttcagcacttaattgaaaattatggaagtatagctcctgatgctttaactgta
accatatcagaaattgctgttaaggatgttacggacaaaactggagggggggtgcaggttactgacagcactacagggcgcctatgcatgtta
gtagaccatgaatataagtacccatatgtgttagggcaaggtcaagatactttagccccagaacttcctatttgggtatactttccccctcaatac
gcttacttaacagtaggagatgttaacacacaaggaatttctggagacagcaaaaaattggcaagtgaagaatcagcattttatgttttggaaca
cagttcttttcagcttttaggtacaggaggtacagcaactatgtcttataagtttcctccagtgcccccagaaaatttagagggctgcagtcaaca
cttttatgaaatgtacaaccccttatacggatcccgcttaggggttcctgacacattaggaggtgacccaaaatttagatctttaacacatgaaga
ccatgcaattcagccccaaaacttcatgccagggccactagtaaactcagtgtctacaaaggagggagacagctctagtactggagctggaa
aagccttaacaggccttagcacaggtacctctcaaaacactagaatatccttacgccctgggccagtgtctcagccgtaccaccactgggaca
cagataaatatgtcacaggaataaatgccatttctcatggtcagaccacttatggtaacgctgaagacaaagagtatcagcaaggagtgggta
gatttccaaatgaaaaagaacagctaaaacagttacagggtttaaacatgcacacctactttcccaataaaggaacccagcaatatacagatca
aattgagcgcccccctaatggtgggttctgtatggaacagaagagcccttcactatgaaagccagctgtggagtaaaattccaaatttagatgac
agttttaaaactcagtttgcagccttaggaggatggggtttgcatcagccacctcctcaaatatttttaaaaatattaccacaaagtgggccaattg
gaggtattaaatcaatgggaattactaccttagttcagtatgccgtgggaattatgacagtaaccatgacatttaaattggggccccgtaaagct
acgggacggtggaatcctcaacctggagtgtatcccccgcacgcagcaggtcatttaccatatgtactatatgaccccacagctacagatgca
aaacaacaccacagacatggatatgaaaagcctgaagaattgtggacagccaaaagccgtgtgcacccattgtaagtcgacatactc

FIG. 7A

B1 VP2 amino acid sequence:

MTSVNSAEASTGAGGGGSNPVKSMWSEGATFSANSVTCTFSRQFLIPYDPEHH
YKVFSPAASSCHNASGKEAKVCTISPIMGYSTPWRYLDFNALNLFFSPLEFQHLIENYGS
IAPDALTVTISEIAVKDVTDKTGGGVQVTDSTTGRLCMLVDHEYKYPYVLGQGQDTLAPE
LPIWVYFPPQYAYLTVGDVNTQGISGDSKKLASEESAFYVLEHSSFQLLGTGGTATMSYK
FPPVPPENLEGCSQHFYEMYNPLYGSRLGVPDTLGGDPKFRSLTHEDHAIQPQNFMPGPL
VNSVSTKEGDSSSTGAGKALTGLSTGTSQNTRISLRPGPVSQPYHHWDTDKYVTGINAIS
HGQTTYGNAEDKEYQQGVGRFPNEKEQLKQLQGLNMHTYFPNKGTQQYTDQIERPLMVGS
VWNRRALHYESQLWSKIPNLDDSFKTQFAALGGWGLHQPPPQIFLKILPQSGPIGGIKSM
GITTLVQYAVGIMTVTMTFKLGPRKATGRWNPQPGVYPPHAAGHLPYVLYDPTATDAKQH
HRHGYEKPEELWTAKSRVHPL

FIG. 7B

B6 NS1 single stranded DNA sequence:

atactcttcgaacaaaacaaaatggagctatttagaggggtgcttcaagtttcttctaatgttctggactgtgctaacgataactggtggtgctcttt
actggatttagacacttctgactgggaaccactaactcatactaacagactaatggcaatatacttaagcagtgtggcttctaagcttgactttact
ggggggccactagcagggtgcttgtactttttcaagtagaatgtaacaaatttgaagaaggctatcatattcatgtggttattggggggccagg
gttaaaccccagaaacctcacagtgtgtgtagaggggttatttaataatgtactttatcaccttgtaactgaaaatctgaagctaaaatttttgcca
ggaatgactacaaaaggcaaatactttagagatggagagcagtttatagaaaactatttaatgaaaaaaatacctttaaatgttgtatggtgtgtt
actaatattgatggacatatagatacctgtatttctgctacttttagaaagggagcttgccatgccaagaaaccccgcatcaccacagccataaa
tgatactagtactgatgctggggagtctagcggcacaggggcagaggttgtgccatttaatgggaagggaactaaggctagcataaagtttca
aactatggtaaactggttgtgtgaaaacagagtgtttacagaggataagtggaaactagttgactttaaccagtacactttactaagcagtagtc
acagtggaagttttcaaattcaaagtgcactaaaactagcaatttataaagcaactaatttagtgcctactagcacatttttattgcatacagacttt
gagcaagttatgtgtattaaagacaataaaattgttaaattgttactttgtcaaaactatgacccccctattagtggggcagcatgtgttaaagtgga
ttgataaaaaatgtggcaagaaaaacacactgtggttttatggaccgccaagtacagggaaaacaaacttggcaatggccattgctaaaagtg
ttccagtatatggcatggttaactggaataatgaaaactttccatttaatgatgtagcaggaaaaagcttggtggtctgggatgaaggtattattaa
gtctacaattgtagaagctgcaaaagccattttaggcgggcaacccaccagggtagatcaaaaaatgcgtggaagtgtagctgtgcctggag
tacccgtggttataaccagcaatggtgacattacttttgttgtaagcgggaacactacaacaactgtacatgctaaagccttaaaagagcgcatg
gtaaagttaaactttactgtaagatgcagccctgacatggggttactaacagaggctgatgtacaacagtggcttacatggtgtaatgcacaaa
gctgggaccactatgaaaactgggcaataaactacacttttgatttccctggaattaatgcagatgccctccacccagacctccaaaccacccc
aattgtcacagacaccagtatcagcagcagtggtggtgaaagctctgaagaactcagtgaaagcagctttttttaacctcatcaccccaggcgc
ctggaacactgaaaccccgcgctctagtacgcccatccccgggaccagttcaggagaatcatctgtcggaagcccagtttcc
tccgaagttgtagctgcatcgtgggaagaagccttctacacacctttggcagaccagtttcgtgaactgttagttggggttgattatgtgtggga
cggtgtaaggggtttacctgtctgttgtgtgcaacatattaacaatagtgggggaggcttgggactttgtccccattgcattaatgtaggggcttg
gtataatggatggaaatttcgagaatttaccccagatttggtgcgatgtagctgccatgtgggagcttctaatccctttttctgtgctaacctgcaaa
aaatgtgcttacctgtctggattgcaaagctttgtagattatgagtaagtcgacatactc

FIG. 8A

B6 NS1 amino acid sequence:

MELFRGVLQVSSNVLDCANDNWWCSLLDLDTSDWEPLTHTNRLMAIYLSSVAS
KLDFTGGPLAGCLYFFQVECNKFEEGYHIHVVIGGPGLNPRNLTVCVEGLFNNVLYHLVT
ENLKLKFLPGMTTKGKYFRDGEQFIENYLMKKIPLNVVWCVTNIDGHIDTCISATFRKGA
CHAKKPRITTAINDTSTDAGESSGTGAEVVPFNGKGTKASIKFQTMVNWLCENRVFTEDK
WKLVDFNQYTLLSSSHSGSFQIQSALKLAIYKATNLVPTSTFLLHTDFEQVMCIKDNKIV
KLLLCQNYDPLLVGQHVLKWIDKKCGKKNTLWFYGPPSTGKTNLAMAIAKSVPVYGMVNW
NNENFPFNDVAGKSLVVWDEGIIKSTIVEAAKAILGGQPTRVDQKMRGSVAVPGVPVVIT
SNGDITFVVSGNTTTTVHAKALKERMVKLNFTVRCSPDMGLLTEADVQQWLTWCNAQSWD
HYENWAINYTFDFPGINADALHPDLQTTPIVTDTSISSSGGESSEELSESSFFNLITPGA
WNTETPRSSTPIPGTSSGESSVGSPVSSEVVAASWEEAFYTPLADQFRELLVGVDYVWDG
VRGLPVCCVQHINNSGGGLGLCPHCINVGAWYNGWKFREFTPDLVRCSCHVGASNPFSVL
TCKKCAYLSGLQSFVDYE

FIG. 8B

B6 VP I single stranded DNA sequence:

atactcaagcttacaaaacaaaatgagtaaagaaagtggcaaatggtgggaaagtgatgataaatttgctaaagctgtgtatcagcaatttgtg
gaatttatgaaaaggttactggaacagacttagagcttattcaaatattaaaagatcattataatatttctttagataatcccctagaaaacccatc
ctctttgtttgacttagttgctcgtattaaaaataaccttaaaaactctccagacttatatagtcatcattttcaaagtcatggacagttatctgaccac
ccccatgccttatcatccagtagcagtcatgcagaacctagaggagaagatgcagtattatctagtgaagacttacacaagcctgggcaagtt
agcgtacaactacccggtactaactatgttgggcctggcaatgagctacaagctgggcccccgcaaagtgctgttgacagtgctgcaaggat
tcatgactttaggtatagccaactggctaagttgggaataaatccatatactcattggactgtagcagatgaagagcttttaaaaaatataaaaaa
tgaaactgggtttcaagcacaagtagtaaaagactactttactttaaaaggtgcagctgcccctgtggcccattttcaaggaagtttgccggaa
gttcccgcttacaacgcctcagaaaaatacccaagcatgacttcagttaattctgcagaagccagcactggtgcaggagggggggggcagta
atcctgtgaaaagcatgtggagtgagggggccacttttagtgccaactctgtaacttgtacattttccagacaatttttaattccatatgacccag
agcaccattataaggtgttttctcccgcagcaagtagctgccacaatgccagtggaaaggaggcaaaggtttgcaccattagtcccataatgg
gatactcaaccccatggagatatttagattttaatgctttaaatttattttttcacctttagagtttcagcacttaattgaaaattatggaagtatagct
cctgatgctttaactgtaaccatatcagaaattgctgttaaggatgttacaaacaaaactggagggggggtgcaggttactgacagcactaca
gggcgcctatgcatgttagtagaccatgaatataagtacccatatgtgttagggcaaggtcaagatactttagccccagaacttcctatttgggt
atactttccccctcaatacgcttacttaacagtaggagatgttaacacacaaggaatttctggagacagcaaaaaattggcaagtgaagaatca
gcattttatgttttggaacacagttcttttcagcttttaggtacaggaggtacagcaactatgtcttataagtttcctccagtgcccccagaaaattt
agagggctgcagtcaacacttttatgaaatgtacaaccccttatacggatcccgcttaggggttcctgacacattaggaggtgacccaaaattt
agatctttaacacatgaagaccatgcaattcagccccaaaacttcatgccagggccactagtaaactcagtgtctacaaaggagggagacag
ctctagtactggagctggaaaagccttaacaggccttagcacaggtacctctcaaaacactagaatatccttacgccctgggccagtgtctca
gccgtaccaccactgggacacagataaatatgtcacaggaataaatgccatttctcatggtcagaccacttatggtaacgctgaagacaaag
agtatcagcaaggagtgggtagatttccaaatgaaaaagaacagctaaaacagttacagggtttaaacatgcacacctactttcccaataaag
gaacccagcaatatacagatcaaattgagcgcccccctaatggtgggttctgtatggaacagaagagcccttcactatgaaagccagctgtgg
agtaaaattccaaatttagatgacagttttaaaactcagtttgcagccttaggaggatggggtttgcatcagccacctcctcaaatattCttaaaa
atattaccacaaagtgggccaa ttggaggtattaaatcaatgggaattactaccttagttcagtatgccgtgggaattatgacagtaaccatga
catttaaa ttggggccccgtaaagctacgggacggtggaatcctcaacctggagtgtatcccccgcacgcagcaggtcatttaccata tgta
ctatatgaccccacagctacagatgcaaaacaacaccacagacatggatatgaaaagcctgaagaattgtggacagccaaaagccgt gtg
cacccattgtaagtcgacatactc

FIG. 9A

B6 VPI amino acid sequence:

MSKESGKWWESDDKFAKAVYQQFVEFYEKVTGTDLELIQILKDHYNISLDNPL
ENPSSLFDLVARIKNNLKNSPDLYSHHFQSHGQLSDHPHALSSSSSHAEPRGEDAVLSSE
DLHKPGQVSVQLPGTNYVGPGNELQAGPPQSAVDSAARIHDFRYSQLAKLGINPYTHWTV
ADEELLKNIKNETGFQAQVVKDYFTLKGAAAPVAHFQGSLPEVPAYNASEKYPSMTSVNS
AEASTGAGGGGSNPVKSMWSEGATFSANSVTCTFSRQFLIPYDPEHHYKVFSPAASSCHN
ASGKEAKVCTISPIMGYSTPWRYLDFNALNLFESPLEFQHLIENYGSIAPDALTVTISEI
AVKDVTNKTGGGVQVTDSTTGRLCMLVDHEYKYPYVLGQGQDTLAPELPIWVYFPPQYAY
LTVGDVNTQGISGDSKKLASEESAFYVLEHSSFQLLGTGGTATMSYKFPPVPPENLEGCS
QHFYEMYNPLYGSRLGVPDTLGGDPKFRSLTHEDHAIQPQNFMPGPLVNSVSTKEGDSSS
TGAGKALTGLSTGTSQNTRISLRPGPVSQPYHHWDTDKYVTGINAISHGQTTYGNAEDKE
YQQGVGRFPNEKEQLKQLQGLNMHTYFPNKGTQQYTDQIERPLMVGSVWNRRALHYESQL
WSKIPNLDDSFKTQFAALGGWGLHQPPPQIFLKILPQSGPIGGIKSMGITTLVQYAVGIM
TVTMTFKLGPRKATGRWNPQPGVYPPHAAGHLPYVLYDPTATDAKQHHRHGYEKPEELWT
AKSRVHPL

FIG. 9B

B6 VP2 single stranded DNA sequence:

atactcaagcttacaaaacaaaatgacttcagttaattctgcagaagccagcactggtgcaggaggggggggcagtaatcctgtgaaaagca
tgtggagtgagggggccacttttagtgccaactctgtaacttgtacattttccagacaatttttaattccatatgacccagagcaccattataaggt
gttttctcccgcagcaagtagctgccacaatgccagtggaaaggaggcaaaggtttgcaccattagtcccataatgggatactcaaccccatg
gagatatttagattttaatgctttaaatttattttttcacctttagagtttcagcacttaattgaaaattatggaagtatagctcctgatgctttaactgta
accatatcagaaattgctgttaaggatgttacaaacaaaactggagggggggtgcaggttactgacagcactacagggcgcctatgcatgtta
gtagaccatgaatataagtacccatatgtgttagggcaaggtcaagatactttagccccagaacttcctatttgggtatactttccccctcaatac
gcttacttaacagtaggagatgttaacacacaaggaatttctggagacagcaaaaaattggcaagtgaagaatcagcattttatgttttggaaca
cagttcttttcagcttttaggtacaggaggtacagcaactatgtcttataagtttcctccagtgcccccagaaaatttagagggctgcagtcaaca
cttttatgaaatgtacaaccccttatacggatcccgcttaggggttcctgacacattaggaggtgacccaaaatttagatctttaacacatgaaga
ccatgcaattcagccccaaaacttcatgccagggccactagtaaactcagtgtctacaaaggagggagacagctctagtactggagctggaa
aagccttaacaggccttagcacaggtacctctcaaaacactagaatatccttacgccctgggccagtgtctcagccgtaccaccactgggaca
cagataaatatgtcacaggaataaatgccatttctcatggtcagaccacttatggtaacgctgaagacaaagagtatcagcaaggagtgggta
gatttccaaatgaaaaagaacagctaaaacagttacagggtttaaacatgcacacctactttcccaataaaggaacccagcaatatacagatca
aattgagcgcccccctaatggtgggttctgtatggaacagaagagcccttcactatgaaagccagctgtggagtaaaattccaaatttagatgac
agttttaaaactcagtttgcagccttaggaggatggggtttgcatcagccacctcctcaaatatttttaaaaatattaccacaaagtgggccaattg
gaggtattaaatcaatgggaattactaccttagttcagtatgccgtgggaattatgacagtaaccatgacatttaaattggggccccgtaaagct
acgggacggtggaatcctcaacctggagtgtatcccccgcacgcagcaggtcatttaccatatgtactatatgaccccacagctacagatgca
aaacaacaccacagacatggatatgaaaagcctgaagaattgtggacagccaaaagccgtgtgcacccattgtaagtcgacatactc

FIG. 10A

B6 VP2 amino acid sequence:

MTSVNSAEASTGAGGGGSNPVKSMWSEGATFSANSVTCTFSRQFLIPYDPEHH
YKVFSPAASSCHNASGKEAKVCTISPIMGYSTPWRYLDFNALNLFFSPLEFQHLIENYGS
IAPDALTVTISEIAVKDVTNKTGGGVQVTDSTTGRLCMLVDHEYKYPYVLGQGQDTLAPE
LPIWVYFPPQYAYLTVGDVNTQGISGDSKKLASEESAFYVLEHSSFQLLGTGGTATMSYK
FPPVPPENLEGCSQHFYEMYNPLYGSRLGVPDTLGGDPKFRSLTHEDHAIQPQNFMPGPL
VNSVSTKEGDSSSTGAGKALTGLSTGTSQNTRISLRPGPVSQPYHHWDTDKYVTGINAIS
HGQTTYGNAEDKEYQQGVGRFPNEKEQLKQLQGLNMHTYFPNKGTQQYTDQIERPLMVGS
VWNRRALHYESQLWSKIPNLDDSFKTQFAALGGWGLHQPPPQIFLKILPQSGPIGGIKSM
GITTLVQYAVGIMTVTMTFKLGPRKATGRWNPQPGVYPPHAAGHLPYVLYDPTATDAKQH
HRHGYEKPEELWTAKSRVHPL

FIG. 10B

CH80-1 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgttaaaagcatgtggagtgagggggccacttttagtgccaact
ctgtaacttgtacattttccagacagtttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttgtttttttcacctttagagtttcagcatttaattgaaaact
atggaagtatagctcctgatgctttaactgtaaccatatcagaaattgctgttaaggatgttacagacaaaactg
gagggggagtacaagttactgacagcactaccgggcgcctatgcatgttagtagaccatgaatacaagtac
ccatatgtgttagggcaaggtcaggatactttag

FIG. 11A

CH81-3 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgttaaaagcatgtggagtgagggggccacttttagtgccaact
ctgtaacttgtacattttccagacagtttttaattccatatgacccagagcaccattataaggtgttttcgcccgca
gcaagtagctgccacaatgccagtggaaaggaggcaaaggtttgcaccattagtcccataatgggatactc
aaccccatggagatacttagattttaatgctttaaatttatttttttcacctttagagtttcagcacttaattgaaaatt
atggaagtatagctcctgatgctttaactgtaaccatatcagaaattgctgttaaggatgttacggacaaaactg
gaggggggtgcaggttactgacagcactacagggcgcctatgcatgttagtagaccatgaatacaagtac
ccatatgtgttagggcaaggtcaggatactttag

FIG. 11B

B19SCL1-4 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacggacaaaactg
gaggggggggtgcaggttactgacagcactacagggcgcctatgcatgttagtagaccatgaatataagtac
ccatatgtgttagggcaaggtcaggatactttag

FIG. 11C

B19SCL2-1 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacggacaaaactg
gaggggggggtgcaggttactgacagcactacagggcgcctatgcatgttagtagaccatgaatataagtac
ccatatgtgttagggcaaggtcaggatactttag

FIG. 11D

B19SCL3-1 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacggacaaaactg
gaggggggggtgcaggttactgacagcactacagggcgcctatgcatgttagtagaccatgaatataagtac
ccatatgtgttagggcaaggtcaggatactttag

FIG. 11E

B19SCL4-3 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggaggggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttattttttcacctttagagtttcagcacttaattgaaaatt
atggaagtatagctcctgatgctttaactgtaaccatatcagaaattgctgttaaggatgttacggacaaaactg
gaggggggggtgcaggttactgacagcactacagggcgcctatgcatgttagtagaccatgaatataagtac
ccatatgtgttagggcaaggtcaggatactttag

FIG. 11F

B19SCL5-2 ataaatccatatactcattggactgtagcagatgaagagcttttaaaaaatataaaaaatgaaactgggtttcaa
gcacaagtagtaaaagactactttactttaaaaggtgcagctgcccctgtggcccattttcaaggaagtttgcc
ggaagttcccgcttacaacgcctcagaaaaatacccaagcatgacttcagttaattctgcagaagccagcac
tggtgcaggagggggggcagtaatcctgtgaaaagcatgtggagtgagggggccacttttagtgccaac
tctgtaacttgtacattttccagacaatttttaattccatatgacccagagcaccattataaggtgttttctcccgca
gcaagtagctgccacaatgccagtggaaaggaggcaaaggtttgcaccattagtcccataatgggatactc
aaccccatggagatatttagattttaatgctttaaatttatttttttcacctttagagtttcagcacttaattgaaaatt
atggaagtatagctcctgatgctttaactgtaaccatatcagaaattgctgttaaggatgttacggacaaaactg
gagggggggtgcaggttactgacagcactacagggcgcctatgcatgttagtagaccatgaatataagtac
ccatatgtgttagggcaaggtcaggatactttag

FIG. 11G

B19SCL6-2 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggagggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttatttttttcacctttagagtttcagcacttaattgaaaat
tatggaagtatagctcctgatgctttaactgtaaccatatcagaaattgctgttaaggatgttacggacaaaact
ggagggggggtgcaggttactgacagcactacagggcgcctatgcatgttagtagaccatgaatataagta
cccatatgtgttagggcaaggtcaggatactttag

FIG. 11H

B19SCL7-3 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11I

B19SCL8-2 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttaggttttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11J

B19SCL9-1 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcaattaattctgcagaagccagca
ctggtgcaggagggggggcagtaatcctgtcaaaagcatgtggagtgagggggccacttttagtgccaa
ctctgtaacttgtacattttccagacagtttttaattccatatgacccagagcaccattataaggtgttttctcccg
cagccagtagctgccacaatgccagtggaaaggaggcaaaggtttgcaccattagtcccataatgggatac
tcaaccccatggagatatttagattttaatgctttaaatttattttttcacctttagagtttcagcacttaattgaaaa
ttatggaagtatagctcctgatgctttaactgtaaccatatcagaaattgctgttaaggatgttacggacaaaac
tggagggggggtgcaggttactgacagcactacagggcgcctatgcatgttagtagaccatgaatataagt
acccatatgtgttagggcaaggtcaggatactttag

FIG. 11K

B19SCL9-9 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggagggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggagggggggtgcaggttactgacagcactacagggcgcctatgcatgttagtagaccatgaatataagta
cccatatgtgttagggcaaggtcaggatactttag

FIG. 11L

B19SCL10-2 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11M

B19SCL11-1 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttat

FIG. 11N

B19SCL12-1 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtcaaaagcatgtggagtgagggggccacttttagtgccaa
ctctgtgacttgtacattttccagacagtttttaattccatatgacccagagcaccattataaggtgttttctcccg
cagcaagtagctgccacaatgccagtggaaaggaggcaaaggtttgcaccattagtccgataatgggatac
tcaaccccatggagatatttagattttaatgctttaaatttattttttcacctttagagtttcagcacttaattgaaaa
ttatggaagtatagctcctgatgctttaactgtaaccatatcagaaattgctgttaaggatgttacagacaaaact
ggaggggggtgcaagttactgacagcagtacagggcgcctatgcatgttagtagaccatgaatacaagta
cccatatgtgttagggcaaggtcaggatactttag

FIG. 11O

B19SCL13-3 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtgcattttccagacaatttttaattccatatgacccagagcaccattataaggtgttttctcccg
cagcaagtagctgccacaatgccagtggaaaggaggcaaaggtttgcaccattagtcccataatgggatac
tcaaccccatggagatatttagattttaatgctttaaatttattttttcacctttagagtttcagcacttaattgaaaa
ttatggaagtatagctcctgatgctttaactgtaaccatatcagaaattgctgttaaggatgttacggacaaaac
tggaggggggtgcaggttactgacagcactacagggcgcctatgcatgttagtagaccatgaatataagt
acccatatgtgttagggcaaggtcaggatactttag

FIG. 11P

B19SCL14-1 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttatttttttcacctttagagtttcagcacttaattgaaaat
tatggaagtatagctcctgatgctttaactgtaaccatatcagaaattgctgttaaggatgttacggacaaaact
ggagggggggtgcaggttactgacagcactacagggcgcctatgcatgttagtagaccatgaatataagta
cccatatgtgttagggcaaggtcaggatactttag

FIG. 11Q

B19SCL15-3 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttatttttttcacctttagagtttcagcacttaattgaaaat
tatggaagtatagctcctgatgctttaactgtaaccatatcagaaattgctgttaaggatgttacggacaaaact
ggagggggggtgcaggttactgacagcactacagggcgcctatgcatgttagtagaccatgaatataagta
cccatatgtgttagggcaaggtcaggatactttag

FIG. 11R

B19SCL16-2 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgaggggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttat

FIG. 11S

B19SCL17-1 ataaatccatatacttattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgaggggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11T

B19SCL18-1 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggtgcaggttactgacagcactacagggcgcctatgcatgttagtagaccatgaatataagta
cccatatgtgttagggcaaggtcaggatactttag

FIG. 11U

B19SCL19-1 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggtgcaggttactgacagcactacagggcgcctatgcatgttagtagaccatgaatataagta
cccatatgtgttagggcaaggtcaggatactttag

FIG. 11V

B19SCL20-3 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11W

B19SCL21-3 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttattttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11X

B19SCL22-11 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcgggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatttagattttaatgctttaaatttatttttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11Y

B19SCL2-14 ataaatccatatactcattggactgtagcagatgaagagcttttaaaaaatataaaaaatgaaactgggtttca
agcacaagtagtaaaagactactttactttaaaaggtgcagctgcccctgtggcccattttcaaggaagtttgc
cggaagttcccgcttacaacgcctcagaaaaatacccaagcatgacttcagttaattctgcagaagccagca
ctggtgcaggaggggggggcagtaatcctgtgaaaagcatgtggagtgagggggccacttttagtgccaa
ctctgtaacttgtacattttccagacaatttttaattccatatgacccagagcaccattataaggtgttttctcccgc
agcaagtagctgccacaatgccagtggaaaggaggcaaaggtttgcaccattagtcccataatgggatact
caaccccatggagatatctagattttaatgctttaaatttatttttttcacctttagagtttcagcacttaattgaaaat
tatggaagtatagctcctgatgctttaactgtaaccatatcagaaattgctgttaaggatgttacggacaaaact
ggaggggggggtgcaggttactgacagcactacagggcgcctatgcatgttagtagaccatgaatataagta
cccatatgtgttagggcaaggtcaggatactttag

FIG. 11Z

GAATTCACTTGTACATTTTCCAGACAATTTTTAATTCCATATGACCCAGAGCACCATT
ATACAGTGACATGCAGGTCTAGCTCTGCCACAATGCCAGTGGAAAGGAGGCAAAGG
TTTGCACCATTAGTCCCATAATGGGATACTCAACCCCATGGAGATATTTAGATTTTA
ATGCTTTAAATTTATTTTTTTCACCTTTAGAGTTTCAGCACTTAATTGAAAATTATGG
AAGTATAGCTCCTGATGCTTTAACTGTAACCATATCAGAAATTGCTGTTAAGGATGT
TACGGACAAAACTGGAGGGGGGGTGCAGGTTACTGACAGCACTACAGGGCGCCTAT
GCATGTTAGTAGACCATGAATATAAGTACCCATATGTGTTAGGGCAAGGTCAAGATA
CTTTAGCCCCAGAACTTCCTATTTGGGTATACTTTCCCCCTCAATACGCTTACTTAAC
AGTAGGAGATGTTAACACACAAGGAATTTCTGGAGACAGCAAAAAATTGGCAAGTG
AAGAATCAGCATTTTATGTTTTGGAACACAGTTCTTTTCAGCTTTTAGGTACAGGAG
GTACAGCAACTATGTCTTATAAGTTTCCTCCAGTGCCCCCAGAAAATTTAGAGGGCT
GCAGTCAACACTTTTATGAAATGTACAACCCCTTATACGGATCCCGCTGTCGAC.

FIG. 12

DIAGNOSTIC ASSAYS FOR PARVOVIRUS B19

CROSS-REFERENCE TO RELATED APPLICATIONS

This application is related to provisional patent application Ser. Nos. 60/302,077, filed Jun. 28, 2001; 60/365,956, filed Mar. 19, 2002; and 60/369,224, filed Mar. 29, 2002, from which applications priority is claimed under 35 USC § 119(e)(1) and which applications are incorporated herein by reference in their entireties.

TECHNICAL FIELD

The present invention pertains generally to viral diagnostics. In particular, the invention relates to nucleic acid-based assays for accurately diagnosing parvovirus B19 infection and to primers and probes for use in these assays.

BACKGROUND OF THE INVENTION

Human parvovirus B19 is a member of the family Parvoviridae, genus Erythrovirus and is a small 22-nm icosahedral nonenveloped virus with a linear single-stranded DNA molecule of approximately 5,600 nucleotides. The viral genome encodes three major proteins, VP1, VP2 and NS1. See, Shade et al., *J. Virol.* (1986) 58:921–936 and FIG. 1 herein. VP1 (83 kDa) and VP2 (58 kDa) are the structural proteins of the capsid. The two proteins are encoded in overlapping reading frames from about nucleotides 2444 to 4789 and about 3125 to 4789, respectively. VP2 constitutes 95% of the capsid and the larger VP1 protein only 5% of the capsid. VP1 is required for the mature conformation of the virus. NS1 (77 kDa), is a nonstructural protein and is present only in the nuclear fraction of infected cells and absent from the cytoplasm and intact virions in sera.

Parvovirus B19 was first discovered in the sera of normal blood donors and is the only member of the family Parvoviridae known to be pathogenic in humans. The virus is associated with a wide range of disease manifestations. Human parvovirus B19 normally causes an asymptomatic or mild self-limiting infection in children. In adults, parvovirus B19 may cause a rash, transient symmetrical polyarthralgia and arthritis. Parvovirus B19 has been associated with transient aplastic crisis (TAC) in patients with underlying hemolytic disorders. Chronic B19 infection and persistent anemia have been reported in immunocompromised patients with acute leukemia, congenital immunodeficiencies, AIDS, and following bone marrow transplantation. Parvovirus B19 has also been associated with fetal death in pregnant women.

In most countries, B19 virus infection generally occurs during childhood, with approximately 50% of children having anti-B19 antibodies by the age of 15 years. B19 antibody prevalence may further increase during lifetime and reaches values higher than 90% in elderly individuals.

In human parvovirus B19 infection, initial viral replication is believed to occur in the respiratory tract. The virus then targets cells in the bone marrow. This leads to large-scale viral replication with reported viremia of between $10^2$ to $10^{14}$ particles/ml, occurring 7–10 days after infection but prior to the onset of symptoms. Cessation of viremia coincides with the detection of specific IgM antibodies that remain elevated for two to three months. Anti-B19 IgG antibodies are detected a few days after IgM antibodies appear and persist lifelong.

The absence of a lipid envelope and limited DNA content make parvovirus B19 extremely resistant to physicochemical inactivation. Parvovirus B19, especially at high concentration, can withstand conventional heat treatment of blood products and transmission of B19 through the administration of solvent-detergent-treated factor VIII and steam- or dry-heated factor VIII and IX preparations has been documented.

Human parvovirus B19 cannot be grown in conventional cell cultures making laboratory detection and isolation of the virus extremely difficult. Thus, for many years, the only source of antigen consisted of sera from viremic patients. Recombinant antigens have been produced for use in serological assays in an attempt to circumvent these problems. See, e.g., Sisk and Berman, *Biotechnology* (1987) 5:1077–1080; U.S. Pat. No. 6,204,044. Immunoenzymatic IgM capture assays have been used to detect anti-B19 IgM, as well as to diagnose recent B19 infection. The diagnostic performance of a number of commercially available tests, however, is not homogenous. In addition, IgM-based diagnostic tests cannot detect the virus during the viremic stage of infection and once IgM antibodies are synthesized, they can remain in circulation for several months after the end of viremia.

The high prevalence of B19 antibodies in the normal population together with the fact that high viremia usually persists for only one week, make the use of serological based tests impractical. In addition, in immunocompromised patients, serological diagnosis may be unreliable.

Nucleic acid-based hybridization assays, such as dot blot and in situ hybridization have been used for B19 detection. These assays generally have detection limits of 1 to 0.1 pg viral DNA (~$10^4$–$10^5$ viral particles). PCR has greater sensitivity (~100 genome copies). However, DNA hybridization techniques are time consuming and limited in use and PCR is impractical for screening large numbers of samples.

Therefore, there remains a need for the development of reliable diagnostic tests to detect parvovirus B19 in viremic samples, in order to prevent transmission of the virus through blood and plasma derivatives or by close personal contact.

SUMMARY OF THE INVENTION

The present invention is based on the discovery of unique primers and probes for use in nucleic acid-based assays, as well as on the development of a sensitive, reliable nucleic acid-based diagnostic test for the detection of parvovirus B19 DNA in biological samples from potentially infected individuals. The techniques described herein utilize extracted sample DNA as a template for amplification of conserved genomic regions of the B19 sequence using transcription-mediated amplification (TMA), as well as in a 5' nuclease assay, such as the TaqMan™ technique. The methods allow for the detection of B19 DNA in viremic samples having viral titers as low as $10^3$ virus particles/ml.

Accordingly, infected samples can be identified and excluded from transfusion, as well as from the preparation of blood derivatives. The probes and primers described herein are also useful in, for example, standard hybridization methods, as well as in PCR-based techniques, nucleic acid sequence-based amplification (NASBA) and in assays that utilize branched DNA molecules.

Accordingly, in one embodiment, the subject invention is directed to a method of detecting human parvovirus B19 infection in a biological sample. The method comprises:

(a) isolating nucleic acid from a biological sample suspected of containing human parvovirus B19 DNA, wherein the nucleic acid comprises an RNA target sequence;

(b) reacting the isolated parvovirus B19 nucleic acid with a first oligonucleotide which comprises a first primer comprising a complexing sequence sufficiently complementary to the 3'-terminal portion of the RNA target sequence to complex therewith, wherein the first primer further comprises a promoter for a DNA-dependent RNA polymerase 5' and operably linked to the complexing sequence, wherein the reacting is done under conditions that provide for the formation of an oligonucleotide/target sequence complex and initiation of DNA synthesis;

(c) extending the first primer in an extension reaction using the RNA target sequence as a template to give a first DNA primer extension product complementary to the RNA target sequence;

(d) separating the first DNA primer extension product from the RNA target sequence using an enzyme which selectively degrades the RNA target sequence;

(e) treating the DNA primer extension product with a second oligonucleotide which comprises a second primer comprising a complexing sequence sufficiently complementary to the 3'-terminal portion of the DNA primer extension product to complex therewith under conditions that provide for the formation of an oligonucleotide/target sequence complex and initiation of DNA synthesis;

(f) extending the 3'-terminus of the second primer in a DNA extension reaction to give a second DNA primer extension product, thereby producing a template for the DNA-dependent RNA polymerase;

(g) using the template to produce multiple RNA copies of the target sequence using a DNA-dependent RNA polymerase which recognizes the promoter sequence; and (h) using the RNA copies of step (g), autocatalytically repeating steps (b) to (g) to amplify the target sequence.

In certain embodiments, the method further comprises the steps of:

(i) adding a labeled oligonucleotide probe to the product of step (h), wherein the oligonucleotide probe is complementary to a portion of the target sequence, under conditions that provide for the hybridization of the probe with the target sequence to form a probe:target complex; and (j) detecting the presence or absence of label as an indication of the presence or absence of the target sequence.

In additional embodiments, the label is an acridinium ester.

In yet further embodiments, the first and second primers, and the probe used in the methods above are derived from the VP1 region of the human parvovirus B19 genome, such as from the polynucleotide sequence depicted in any one of FIGS. 2A–2U or 11A–11Z.

In another embodiment, the invention is directed to a method of detecting human parvovirus B19 infection in a biological sample. The method comprises:

(a) isolating nucleic acid from a biological sample suspected of containing human parvovirus B19 DNA, wherein the nucleic acid comprises an RNA target sequence;

(b) reacting the isolated parvovirus B19 nucleic acid with a first oligonucleotide which comprises a first primer comprising a complexing sequence sufficiently complementary to the 3'-terminal portion of the RNA target sequence to complex therewith, wherein the first primer further comprises a promoter for a DNA-dependent RNA polymerase 5' and operably linked to the complexing sequence, wherein the first primer comprises a sequence derived from the polynucleotide sequence depicted in any one of FIGS. 2A–2U or FIGS. 11A–11Z and the reacting is done under conditions that provide for the formation of an oligonucleotide/target sequence complex and initiation of DNA synthesis;

(c) extending the first primer in an extension reaction using the RNA target sequence as a template to give a first DNA primer extension product complementary to the RNA target sequence;

(d) separating the first DNA primer extension product from the RNA target sequence using an enzyme which selectively degrades the RNA target sequence;

(e) treating the DNA primer extension product with a second oligonucleotide which comprises a second primer comprising a complexing sequence sufficiently complementary to the 3'-terminal portion of the DNA primer extension product to complex therewith, wherein the second primer is derived from the polynucleotide sequence depicted in any one of FIGS. 2A–2U or FIGS. 11A–11Z and the treating is done under conditions that provide for the formation of an oligonucleotide/target sequence complex and initiation of DNA synthesis;

(f) extending the 3'-terminus of the second primer in a DNA extension reaction to give a second DNA primer extension product, thereby producing a template for the DNA-dependent RNA polymerase;

(g) using the template to produce multiple RNA copies of the target sequence using a DNA-dependent RNA polymerase which recognizes the promoter sequence; and (h) using the RNA copies of step (g), autocatalytically repeating steps (b) to (g) to amplify the target sequence;

(i) adding an acridinium ester-labeled oligonucleotide probe to the product of step (h), wherein the oligonucleotide probe is complementary to a portion of said target sequence and the probe is derived from the polynucleotide sequence depicted in any one of FIGS. 2A–2U, wherein the probe is added under conditions that provide for the hybridization of the probe with the target sequence to form a probe:target complex; and (j) detecting the presence or absence of label as an indication of the presence or absence of the target sequence.

In yet another embodiment, the invention is directed to a method for amplifying a target parvovirus B19 nucleotide sequence. The method comprises:

(a) isolating nucleic acid from a biological sample suspected of containing human parvovirus B19 DNA, wherein the nucleic acid comprises an RNA target sequence;

(b) adding one or more primers capable of hybridizing to the RNA target sequence, wherein the one or more primers are derived from the polynucleotide sequences depicted in any one of FIGS. 2A–2U and FIGS. 11A–11Z;

(c) adding an oligonucleotide probe capable of hybridizing to the RNA target sequence 3' relative to the one or more primers;

(d) extending the one or more primers using a polymerase.

In certain embodiments, the RNA target sequence of step (a) is reverse transcribed to provide cDNA and the method can further comprise amplifying the cDNA using polymerase chain reaction (RT-PCR) or asymmetric gap ligase chain reaction (RT-AGLCR). In other embodiments, the polymerase is a thermostable polymerase, such as but not limited to Taq polymerase or Vent polymerase. In additional embodiments, the polymerase is *E. coli* DNA polymerase I, Klenow fragment of *E. coli* DNA polymerase I, or T4 DNA polymerase.

In certain embodiments of the various methods described above, an internal control is provided. The internal control can be derived from the sequence of FIG. 12 (SEQ ID NO:92). In additional embodiments, the internal control comprises SEQ ID NO:90.

In additional embodiments, the invention is directed to a method for detecting human parvovirus B19 infection in a biological sample. The method comprises:

(a) isolating nucleic acid from a biological sample suspected of containing human parvovirus B19 DNA, wherein the nucleic acid comprises a target sequence;

(b) reacting the isolated parvovirus B19 nucleic acid with a detectably labeled probe sufficiently complementary to and capable of hybridizing with the target sequence, wherein the probe is derived from the polynucleotide sequences depicted in any one of FIGS. 2A–2U and FIGS. 11A–11Z, and further wherein the reacting is done under conditions that provide for the formation of a probe/target sequence complex; and (c) detecting the presence or absence of label as an indication of the presence or absence of the target sequence.

In further embodiments, the invention is directed to a polynucleotide comprising a nucleotide sequence comprising any one of the nucleotide sequences depicted in FIGS. 2A–2U or FIGS. 11A–11Z.

In additional embodiments, the invention is directed to a polynucleotide, as above, wherein the nucleotide sequence consists of the nucleotide sequence depicted in FIGS. 2A, 2B, 2C, 2D, 2E, 2F, 2G, 2H, 2I, 2J, 2K, 2L, 2M, 2N, 2O, 2P, 2Q, 2R, 2S, 2T, 2U, 11A, 11B, 11C, 11D, 11E, 11F, 11G, 11H, 11I, 11J, 11K, 11L, 11M, 11N, 11O, 11P, 11Q, 11R, 11S, 11T, 11U, 11V, 11W, 11X, 11Y or 11Z.

In still further embodiments, the subject invention is directed to a polynucleotide comprising a nucleotide sequence comprising any one of the nucleotide sequences depicted in FIGS. 3A–3C or 4A–4C.

In additional embodiments, the invention is directed to a polynucleotide as above, wherein the nucleotide sequence consists of the nucleotide sequence depicted in FIGS. 3A–3C or in FIGS. 4A–4C.

In another embodiment, the invention is directed to an oligonucleotide primer consisting of a promoter region recognized by a DNA-dependent RNA polymerase operably linked to a human parvovirus B19-specific complexing sequence of about 10 to about 75 nucleotides. In certain embodiments, the promoter region is the T7 promoter and said polymerase is T7 RNA polymerase. Additionally, the human parvovirus B19-specific sequence may be from the VP1 region of the human parvovirus B19 genome, such as from the polynucleotide sequence depicted in any one of FIGS. 2A–2U or FIGS. 11A–11Z.

In yet further embodiments, the invention is directed an oligonucleotide primer consisting of a T7 promoter operably linked to a human parvovirus B19-specific complexing sequence of about 10 to about 75 nucleotides, wherein the human parvovirus B19-specific complexing sequence is derived from the polynucleotide sequence depicted in any one of FIGS. 2A–2U or 11A–11Z.

In another embodiment, the invention is directed to an oligonucleotide probe comprising a parvovirus B19-specific hybridizing sequence of about 10 to about 50 nucleotides linked to an acridinium ester label. In certain embodiments, the human parvovirus B19-specific hybridizing sequence is from the VP1 region of the human parvovirus B19 genome, such as from the polynucleotide sequence depicted in any one of FIGS. 2A–2U or FIGS. 11A–11Z.

In yet an additional embodiment, the invention is directed to a diagnostic test kit comprising one or more oligonucleotide primers described herein, and instructions for conducting the diagnostic test. In certain embodiments, the test kit further comprises an oligonucleotide probe comprising a parvovirus B19-specific hybridizing sequence of about 10 to about 50 nucleotides linked to an acridinium ester label.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE FIGURES

FIGS. 2A through 2U (SEQ ID NOS:1–21) depict DNA sequences from various parvovirus B19 isolates which include sequences corresponding to nucleotide positions 2936–3635 of the parvovirus B19 genome described in Shade et al., *J. Virol.* (1986) 58:921–936 (the 700 bp fragment from FIG. 1). FIG. 2A (SEQ ID NO:1) is the corresponding sequence from isolate CH47-26; FIG. 2B (SEQ ID NO:2) is the corresponding sequence from isolate CH48-29; FIG. 2C (SEQ ID NO:3) is the corresponding sequence from isolate CH33-2; FIG. 2D (SEQ ID NO:4) is the corresponding sequence from isolate CH33-3; FIG. 2E (SEQ ID NO:5) is the corresponding sequence from isolate CH33-4; FIG. 2F (SEQ ID NO:6) is the corresponding sequence from isolate CH42-7; FIG. 2G (SEQ ID NO:7) is the corresponding sequence from isolate CH42-18; FIG. 2H (SEQ ID NO:8) is the corresponding sequence from isolate CH42-19; FIG. 2I (SEQ ID NO:9) is the corresponding sequence from isolate CH46-23; FIG. 2J (SEQ ID NO:10) is the corresponding sequence from isolate CH1-1; FIG. 2K (SEQ ID NO:11) is the corresponding sequence from isolate CH1-6; FIG. 2L (SEQ ID NO:12) is the corresponding sequence from isolate CH2-8; FIG. 2M (SEQ ID NO:13) is the corresponding sequence from isolate CH2-10; FIG. 2N (SEQ ID NO:14) is the corresponding sequence from isolate CH2-11C; FIG. 2O (SEQ ID NO:15) is the corresponding sequence from isolate CH5-13; FIG. 2P (SEQ ID NO: 16) is the corresponding sequence from isolate CH7-22; FIG. 2Q (SEQ ID NO:17) is the corresponding sequence from isolate CH13-27; FIG. 2R (SEQ ID NO:18) is the corresponding sequence from isolate CH14-33; FIG. 2S (SEQ ID NO:19) is the corresponding sequence from isolate CH62-2; FIG. 2T (SEQ ID NO:20) is the corresponding sequence from isolate CH64-2; and FIG. 2U (SEQ ID NO:21) is the corresponding sequence from isolate CH67-2.

FIGS. 3A–3C (SEQ ID NO:22) show a sequence for the approximately 4.7 kbp PCR fragment shown in FIG. 1 from parvovirus B19 clone 2-B1. The sequence is a 4677 nucleotide fragment corresponding to nucleotide positions 217–4893 of Shade et al., *J. Virol.* (1986) 58:921–936. The sequence depicted contains the parvovirus B19 full-length open reading frame which encodes NS1, VP1 and VP2, plus additional 5' and 3' untranslated sequences.

FIGS. 4A–4C (SEQ ID NO:23) show a sequence for the approximately 4.7 kbp PCR fragment shown in FIG. 1 from parvovirus B19 clone 2-B6. The sequence is a 4677 nucleotide fragment corresponding to nucleotide positions 217–4893 of Shade et al., *J. Virol.* (1986) 58:921–936. The sequence depicted contains the parvovirus B19 full-length open reading frame which encodes NS1, VP1 and VP2, plus additional 5' and 3' untranslated sequences.

FIGS. 5A (SEQ ID NO:24) and 5B (SEQ ID NO:25) show the NS1 nucleotide and protein sequences, respectively, from parvovirus B19 clone 2-B1.

FIGS. 6A (SEQ ID NO:26) and 6B (SEQ ID NO:27) show the VP1 nucleotide and protein sequences, respectively, from parvovirus B19 clone 2-B1.

FIGS. 7A (SEQ ID NO:28) and 7B (SEQ ID NO:29) show the VP2 nucleotide and protein sequences, respectively, from parvovirus B19 clone 2-B1.

FIGS. 8A (SEQ ID NO:30) and 8B (SEQ ID NO:31) show the NS1 nucleotide and protein sequences, respectively, from parvovirus B19 clone 2-B6.

FIGS. 9A (SEQ ID NO:32) and 9B (SEQ ID NO:33) show the VP1 nucleotide and protein sequences, respectively, from parvovirus B19 clone 2-B6.

FIGS. 10A (SEQ ID NO:34) and 10B (SEQ ID NO:35) show the VP2 nucleotide and protein sequences, respectively, from parvovirus B19 clone 2-B6.

FIGS. 11A through 11Z (SEQ ID NOS:62–87) depict DNA sequences from various parvovirus B19 isolates which include sequences corresponding to nucleotide positions 2936–3635 of the parvovirus B19 genome described in Shade et al., *J. Virol.* (1986) 58:921–936 (the 700 bp fragment from FIG. 1). FIG. 11A (SEQ ID NO:62) is the corresponding sequence from isolate CH80-1; FIG. 11B (SEQ ID NO:63) is the corresponding sequence from isolate CH81-3; FIG. 11C (SEQ ID NO:64) is the corresponding sequence from isolate B19SCL1-4; FIG. 11D (SEQ ID NO:65) is the corresponding sequence from isolate B19SCL2-1; FIG. 11E (SEQ ID NO:66) is the corresponding sequence from isolate B19SCL3-1; FIG. 11F (SEQ ID NO:67) is the corresponding sequence from isolate B19SCL4-3; FIG. 11G (SEQ ID NO:68) is the corresponding sequence from isolate B19SCL5-2; FIG. 11H (SEQ ID NO:69) is the corresponding sequence from isolate B19SCL6-2; FIG. 11I (SEQ ID NO:70) is the corresponding sequence from isolate B19SCL7-3; FIG. 11J (SEQ ID NO:71) is the corresponding sequence from isolate B19SCL8-2; FIG. 11K (SEQ ID NO:72) is the corresponding sequence from isolate B19SCL9-1; FIG. 11L (SEQ ID NO:73) is the corresponding sequence from isolate B19SCL9-9; FIG. 11M (SEQ ID NO:74) is the corresponding sequence from isolate B19SCL10-2; FIG. 11N (SEQ ID NO:75) is the corresponding sequence from isolate B19SCL11-1; FIG. 11O (SEQ ID NO:76) is the corresponding sequence from isolate B19SCL12-1; FIG. 11P (SEQ ID NO:77) is the corresponding sequence from isolate B19SCL13-3; FIG. 11Q (SEQ ID NO:78) is the corresponding sequence from isolate B19SCL14-1; FIG. 11R (SEQ ID NO:79) is the corresponding sequence from isolate B19SCL15-3; FIG. 11S (SEQ ID NO:80) is the corresponding sequence from isolate B19SCL16-2; FIG. 11T (SEQ ID NO:81) is the corresponding sequence from isolate B19SCL17-1; FIG. 11U (SEQ ID NO:82) is the corresponding sequence from isolate B19SCL18-1; FIG. 11V (SEQ ID NO:83) is the corresponding sequence from isolate B19SCL19-1; FIG. 11W (SEQ ID NO:84) is the corresponding sequence from isolate B19SCL20-3; FIG. 11X (SEQ ID NO:85) is the corresponding sequence from isolate B19SCL21-3; FIG. 11Y (SEQ ID NO:86) is the corresponding sequence from isolate B19SCL22-11; FIG. 11Z (SEQ ID NO:87) is the corresponding sequence from isolate B19SCL2-14.

FIG. 12 (SEQ ID NO:92) depicts an exemplary sequence from which an internal control (IC) can be derived for target capture and amplification.

DETAILED DESCRIPTION OF THE INVENTION

Figure 1:
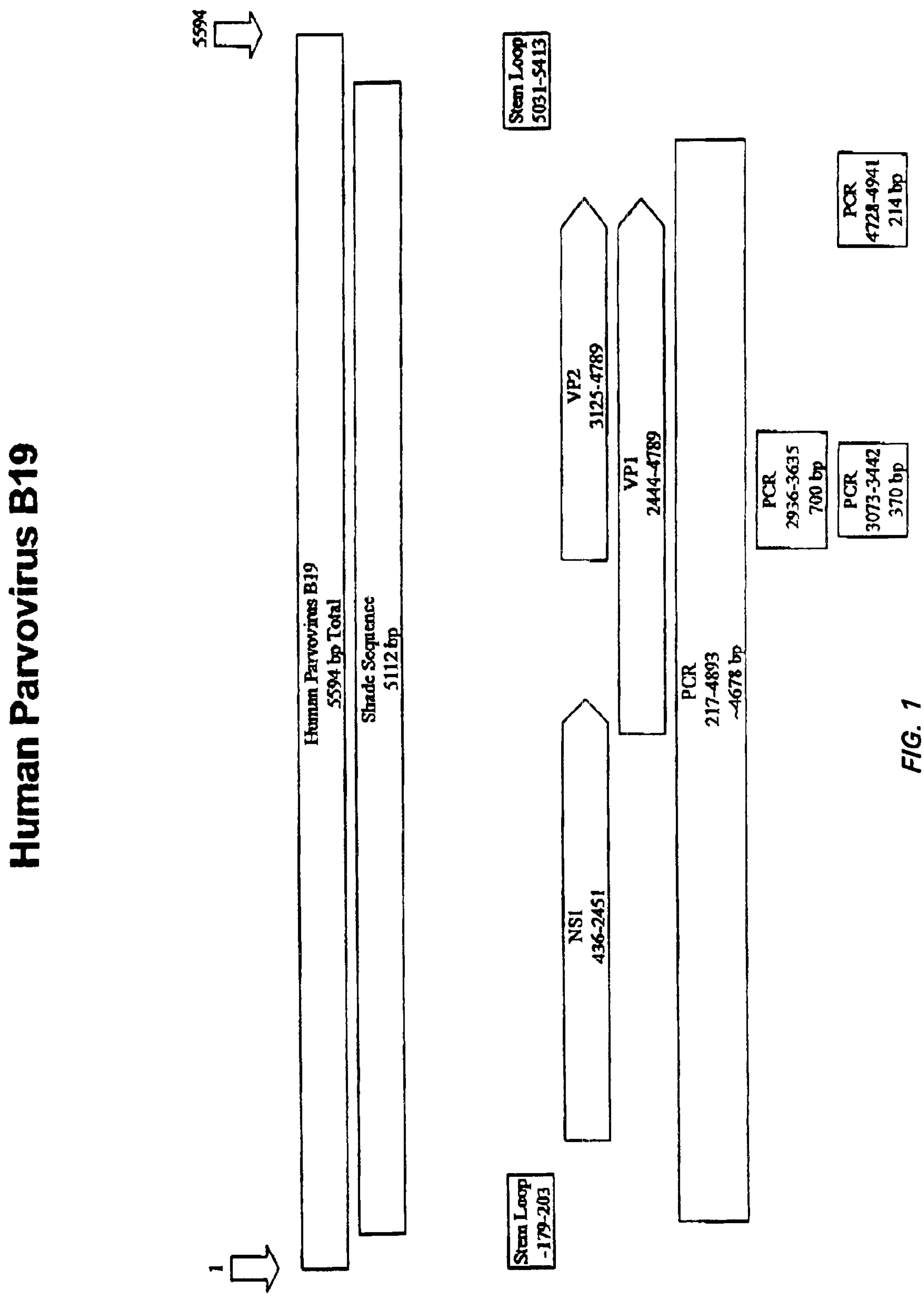
FIG. 1 is a diagrammatic representation of the human parvovirus B19 genome, depicting the various coding regions of the virus. Three PCR fragments are depicted, one with approximately 700 bp, corresponding to nucleotide positions 2936–3635 of the parvovirus B19 genome described in Shade et al., *J. Virol.* (1986) 58:921–936; one with approximately 370 bp within the 700 bp fragment, corresponding to nucleotide positions 3073–3442 of the parvovirus B19 genome described in Shade et al., *J. Virol.* (1986) 58:921–936; and one with approximately 214 bp corresponding to nucleotide positions 4728–4941 of the parvovirus B19 genome described in Shade et al., *J. Virol.* (1986) 58:921–936.

The practice of the present invention will employ, unless otherwise indicated, conventional methods of chemistry, biochemistry, recombinant DNA techniques and virology, within the skill of the art. Such techniques are explained fully in the literature. See, e.g., *Fundamental Virology*, 2nd Edition, vol. I & II (B. N. Fields and D. M. Knipe, eds.); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.);

*Oligonucleotide Synthesis* (N. Gait, ed., 1984); *A Practical Guide to Molecular Cloning* (1984).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

A parvovirus B19 polypeptide is a polypeptide, as defined above, derived from a protein encoded by the B19 genome, such as from the nonstructural proteins, NS1 and NS2, as well as from the proteins which form the viral capsid, VP1 (approximately 781 amino acids in length) or VP2 (approximately 554 amino acids in length). Representative NS1, VP1 and VP2 sequences are depicted in FIGS. 5–10 herein. The polypeptide need not be physically derived from parvovirus B19, but may be synthetically or recombinantly produced. Moreover, the polypeptide may be derived from any of the various parvovirus B19 strains and isolates. A number of conserved and variable regions are known between these strains and isolates and, in general, the amino acid sequences of, for example, epitopes derived from these regions will have a high degree of sequence homology, e.g., amino acid sequence homology of more than 30%, preferably more than 40%, when the two sequences are aligned. Thus, for example, the term "VP1" polypeptide refers to native VP1 from any of the various parvovirus B19 strains and isolates. The complete genotypes and sequences for the above proteins of many parvovirus B19 strains and isolates are known. See, e.g., Shade et al., *J. Virol.* (1986) 58:921–936; Gallinella et al., *J. Virol. Methods* (1993) 41:203–211. Moreover, epitopes from parvovirus B19 derived from these regions are also known. See, e.g., U.S. Pat. No. 5,436,127; and International Publication No. WO 91/12269.

The terms "analog" and "mutein" refer to biologically active derivatives of the reference molecule, or fragments of such derivatives, that retain desired activity, such as immunoreactivity in diagnostic assays. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

A polynucleotide "derived from" or "specific for" a designated sequence refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Operably linked" refers to an arrangement of elements wherein the components so described are configured so as to perform their desired function. Thus, a given promoter operably linked to a nucleic acid sequence is capable of effecting the transcription, and in the case of a coding sequence, the expression of the coding sequence when the proper transcription factors, etc., are present. The promoter need not be contiguous with the nucleic acid sequence, so long as it functions to direct the transcription and/or expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a regulatory region capable of binding a polymerase and initiating transcription of a downstream (3' direction) nucleotide sequence operably linked thereto. For purposes of the present invention, a promoter sequence includes the minimum number of bases or elements necessary to initiate transcription of a sequence of interest at levels detectable above background. Within the promoter sequence is a transcription initiation site, as well as protein binding domains (consensus sequences) responsible for the binding of RNA or DNA polymerase. For example, promoter may be a nucleic acid sequence that is recognized by a DNA-dependent RNA polymerase ("transcriptase") as a signal to bind to the nucleic acid and begin the transcription of RNA at a specific site. For binding, such transcriptases generally require DNA which is double-stranded in the portion comprising the promoter sequence and its complement; the template portion (sequence to be transcribed) need not be double-stranded. Individual DNA-dependent RNA polymerases recognize a variety of different promoter sequences which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

A control sequence "directs the transcription" of a nucleotide sequence when RNA or DNA polymerase will bind the promoter sequence and transcribe the adjacent sequence.

A "DNA-dependent DNA polymerase" is an enzyme that synthesizes a complementary DNA copy from a DNA template. Examples are DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. The degradation may result in separation of RNA from a RNA:DNA complex. Alternatively, the RNAse H may simply cut the RNA at various locations such that portions of the RNA melt off or permit enzymes to unwind portions of the RNA.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands.

The term "primer" or "oligonucleotide primer" as used herein, refers to an oligonucleotide which acts to initiate synthesis of a complementary DNA strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer is first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the term "probe" or "oligonucleotide probe" refers to a structure comprised of a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. When an "oligonucleotide probe" is to be used in a 5' nuclease assay, such as the TaqMan™ technique, the probe will contain at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, a DNA molecule will bind to a substantially complementary sequence and not to unrelated sequences.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25° C. below the $T_m$. The $T_m$ may be estimated using the following relationship: $T_m$=69.3+0.41(GC) % (Marmur et al. (1962) *J. Mol. Biol.* 5:109–118).

As used herein, a "biological sample" refers to a sample of tissue or fluid isolated from a subject, that commonly includes antibodies produced by the subject. Typical samples that include such antibodies are known in the art and include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel primers and probes and diagnostic methods for accurately detecting parvovirus B19 infection in a biological sample. The methods rely on sensitive nucleic acid-based detection techniques that allow identification of parvovirus B19 target nucleic acid sequences in samples containing small amounts of virus.

In particular, the inventors herein have characterized regions within the parvovirus B19 genome which are desirable targets for diagnostic tests. Primers and probes derived from these regions are extremely useful for detection of parvovirus B19 infection in biological samples.

Parvovirus B19 primers and probes described above are used in nucleic acid-based assays for the detection of human parvovirus B19 infection in biological samples. In particular, primers and probes for use in these assays are preferably derived from the approximately 4.7 kb fragment of the parvovirus B19 genome corresponding to nucleotide positions 217–4678 of Shade et al., *J. Virol.* (1986) 58:921–936. The nucleotide sequences of this region from two different parvovirus B19 isolates are depicted in FIGS. 3A–3C and 4A–4C herein. As explained above, this fragment contains the NS1, VP1 and VP2 coding regions.

Particularly preferred primers and probes for use with the present assays are designed from highly conserved regions of the parvovirus B19 genome to allow detection of parvovirus B19 infection caused by a variety of isolates. As described herein, a highly conserved region of the parvovirus B19 genome is found within the 700 bp region spanning nucleotide positions 2936–3635, numbered relative to the parvovirus B19 genome described in Shade et al., *J. Virol.* (1986) 58:921–936. This region is found within the VP1 region of the genome. The sequence of this region from 21 different parvovirus B19 isolates is shown herein in FIGS. 2A–2U. The sequences from an additional 26 isolates are shown in FIGS. 11A–11Z herein. A comparison of the sequences shows that this region displays from about 98% to 99.5% sequence homology from isolate to isolate, making it a highly desirable target sequence. Also desirable for the design of primers and probes is the 370 bp region found within VP1 which spans approximately nucleotide positions 3073–3442, numbered relative to Shade et al., *J. Virol.* (1986) 58:921–936, as well as the 214 bp fragment depicted in FIG. 1 which occurs within the 3' portion of the 4.7 kb fragment and spans nucleotide positions 4728–4941, numbered relative to Shade et al., *J. Virol.* (1986) 58:921–936.

The 4.7 kbp, 700 bp and 370 bp regions are readily obtained from additional isolates using portions of the parvovirus B19 sequence found within these particular regions as primers in PCR reactions such as those described herein, as well as in U.S. Pat. Nos. 4,683,195, 4,683,202 and 4,889,818, and based on the sequences provided herein. Another method of obtaining nucleotide sequences with the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) *Proc. Natl. Acad. Sci. USA* 88:4084–4088. Once the sequences have been prepared or isolated, they can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements. Recombinant clones are readily identified by restriction enzyme analysis and polyacryamide or agarose gel electrophresis, using techniques well known in the art, and described in the examples below.

Primers and probes for use in the assays herein are derived from these sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) *Tetrahedron* 48:2223–2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) *J. Am. Chem. Soc.* 113:6324–6326; U.S. Pat. No. 4,914,210 to Levenson et al.; Durand et al. (1990) *Nucleic Acids Res.* 18:6353–6359; and Horn et al. (1986) *Tet. Lett.* 27:4705–4708. Typically, the primer sequences are in the range of between 10–75 nucleotides in length, such as 15–60, 20–40 and so on, more typically in the range of between 18–40 nucleotides long, and any length between the stated ranges. The typical probe is in the range of between 10–50 nucleotides long, such as 15–40, 18–30, and so on, and any length between the stated ranges.

Moreover, the probes may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363–384 which discloses the use of ferritin-avidin-biotin labels; and Chollet et al. *Nucl. Acids Res.* (1985) 13:1529–1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) *Nucl. Acids Res.* 15:3131–3139, Gibson et al. (1987) *Nucl. Acids Res.* 15:6455–6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) *Nuc. Acids Res.* 13:4485–4502 and Spoat et al. (1987) *Nucl. Acids Res.* 15:4837–4848. A comprehensive review of methodologies for labeling DNA fragments is provided in Matthews et al., *Anal. Biochem.* (1988) 169:1–25.

For example, probes may be fluorescently labeled by linking a fluorescent molecule to the non-ligating terminus of the probe. Guidance for selecting appropriate fluorescent labels can be found in Smith et al., *Meth. Enzymol.* (1987) 155:260–301; Karger et al., *Nucl. Acids Res.* (1991) 19:4955–4962; Haugland (1989) *Handbook of Fluorescent Probes and Research Chemicals* (Molecular Probes, Inc., Eugene, Oreg.). Preferred fluorescent labels include fluorescein and derivatives thereof, such as disclosed in U.S. Pat. No. 4,318,846 and Lee et al., *Cytometry* (1989) 10:151–164, and 6-FAM, JOE, TAMRA, ROX, HEX-1, HEX-2, ZOE, TET-1 or NAN-2, and the like.

Additionally, probes can be labeled with an acridinium ester (AE) using the techniques described below. Current technologies allow the AE label to be placed at any location within the probe. See, e.g., Nelson et al. (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474–1479; Berry et al., *Clin. Chem.* (1988) 34:2087–2090. An AE molecule can be directly attached to the probe using non-nucleotide-based linker arm chemistry that allows placement of the label at any location within the probe. See, e.g., U.S. Pat. Nos. 5,585,481 and 5,185,439.

In certain embodiments, an internal control (IC) or an internal standard is added to serve as a control for target capture and amplification. Preferably, the IC includes a sequence that differs from the target sequence, is capable of hybridizing with the probe sequences used for separating the oligonucleotides specific for the organism from the sample, and is capable of amplification. The use of the IC permits the control of the separation process, the amplification process, and the detection system, and permits the monitoring of assay performance and quantification for the sample(s). A representative sequence from which the IC can be obtained is shown in FIG. 12. The IC can be included at any suitable point, for example, in the lysis buffer. In one embodiment, the IC comprises M13 ssDNA containing a nucleotide sequence from a parvovirus B19 and a unique sequence that hybridizes with the probe, for example, comprising sequences from the VP1 region, where the target sequence is modified by substituting or deleting 5–20 bases or more, preferably 5–15 bases, such as 5, 10 or 15, bases or any number within these ranges. The substituted or deleted bases preferably occur over the entire length of the target sequence such that only 2 or 3 consecutive sequences are replaced. Thus for example, if the target sequence is CTACTTGCT-GCGGGAGAAAAACACCT (SEQ ID NO:91), then the sequence may be substituted with, for example, AGCTA-GACCTGCATGTCACTG (SEQ ID NO:90) in the IC.

The solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies. Typically, the copy number of the IC which does not interfere with the target detection is determined by titrating the IC with a fixed IU of target, preferably at the lower end, and a standard curve is generated by diluting a sample of internationally accepted IU. For parvovirus B19 quantitation, an eight member panel of 8000 IU–125 IU can be used.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known standards.

The primers and probes described above may be used in polymerase chain reaction (PCR)-based techniques to detect parvovirus B19 infection in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation*, in *PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

RNAs may be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) *PCR Meth. App.* 4:80–84.

The fluorogenic 5' nuclease assay, known as the TaqMan™ assay (Perkin-Elmer), is a powerful and versatile PCR-based detection system for nucleic acid targets. Hence, primers and probes derived from regions of the parvovirus B19 genome described herein can be used in TaqMan™ analyses to detect the presence of infection in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers.

The fluorogenic 5' nuclease assay is conveniently performed using, for example, AmpliTaq Gold™ DNA polymerase, which has endogenous 5' nuclease activity, to digest an internal oligonucleotide probe labeled with both a fluorescent reporter dye and a quencher (see, Holland et al., *Proc. Natl. Acad. Sci. USA* (1991) 88:7276–7280; and Lee et al., *Nucl. Acids Res.* (1993) 21:3761–3766). Assay results are detected by measuring changes in fluorescence that occur during the amplification cycle as the fluorescent probe is digested, uncoupling the dye and quencher labels and causing an increase in the fluorescent signal that is proportional to the amplification of target DNA.

The amplification products can be detected in solution or using solid supports. In this method, the TaqMan™ probe is designed to hybridize to a target sequence within the desired PCR product. The 5' end of the TaqMan™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention relates to methods for amplifying a target parvovirus B19 nucleotide sequence using a nucleic acid polymerase having 5' to 3' nuclease activity, one or more primers capable of hybridizing to the target B19 sequence, and an oligonucleotide probe capable of hybridizing to the target B19 sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

While the length of the primers and probes can vary, the probe sequences are selected such that they have a lower melt temperature than the primer sequences. Hence, the primer sequences are generally longer than the probe sequences. Typically, the primer sequences are in the range of between 10–75 nucleotides long, more typically in the range of 20–45. The typical probe is in the range of between 10–50 nucleotides long, more typically 15–40 nucleotides in length.

If a solid support is used, the oligonucleotide probe may be attached to the solid support in a variety of manners. For example, the probe may be attached to the solid support by attachment of the 3' or 5' terminal nucleotide of the probe to the solid support. More preferably, the probe is attached to the solid support by a linker which serves to distance the probe from the solid support. The linker is usually at least 15–30 atoms in length, more preferably at least 15–50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred.

The linkages between the solid support, the linker and the probe are preferably not cleaved during removal of base protecting groups under basic conditions at high temperature. Examples of preferred linkages include carbamate and amide linkages.

Examples of preferred types of solid supports for immobilization of the oligonucleotide probe include controlled pore glass, glass plates, polystyrene, avidin-coated polystyrene beads, cellulose, nylon, acrylamide gel and activated dextran.

For a detailed description of the TaqMan™ assay, reagents and conditions for use therein, see, e.g., Holland et al., *Proc. Natl. Acad. Sci, U.S.A.* (1991) 88:7276–7280; U.S. Pat. Nos. 5,538,848, 5,723,591, and 5,876,930, all incorporated herein by reference in their entireties.

The parvovirus B19 sequences described herein may also be used as a basis for transcription-mediated amplification (TMA) assays. TMA provides a method of identifying target nucleic acid sequences present in very small amounts in a biological sample. Such sequences may be difficult or impossible to detect using direct assay methods. In particular, TMA is an isothemal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid, including RNA, from the biological sample of interest suspected of being infected with parvovirus B19; and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. It may, however, be preferable to add exogenous RNAse H, such as *E. coli* RNAse H, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Detection may be done using a wide variety of methods, including direct sequencing, hybridization with sequence-specific oligomers, gel electrophoresis and mass spectrometry. these methods can use heterogeneous or homogeneous formats, isotopic or nonisotopic labels, as well as no labels at all.

One preferable method of detection is the use of target sequence-specific oligonucleotide probes, derived from the 4.7 kbp, 700 bp, 370 bp and 214 bp fragments described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474–1479; Berry et al., *Clin. Chem.* (1988) 34:2087–2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70° C. Alternatively, a second differential hydrolysis step may be conducted at room temperature. This allows elevated pHs to be used, for example in the range of 10–11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing a parvovirus B19 target sequence, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

The oligonucleotide molecules of the present invention may also be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The parvovirus B19 sequences described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

In another aspect of the invention, two or more of the tests described above are performed to confirm the presence of the organism. For example, if the first test used the transcription mediated amplification (TMA) to amplify the nucleic acids for detection, then an alternative nucleic acid testing (NAT) assay is performed, for example, by using PCR amplification, RT PCR, and the like, as described herein. Thus, parvovirus B19 can be specifically and selectively detected even when the sample contains other organisms, such as HIV, and Hepatitis B virus, for example.

As is readily apparent, design of the assays described herein are subject to a great deal of variation, and many formats are known in the art. The above descriptions are merely provided as guidance and one of skill in the art can readily modify the described protocols, using techniques well known in the art.

The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

In the following examples, enzymes were purchased from commercial sources, and used according to the manufacturers' directions. Nitrocellulose filters and the like were also purchased from commercial sources.

In the isolation of DNA fragments, except where noted, all DNA manipulations were done according to standard procedures. See, Sambrook et al., supra. Restriction enzymes, $T_4$ DNA ligase, *E. coli*, DNA polymerase I, Klenow fragment, and other biological reagents can be purchased from commercial suppliers and used according to the manufacturers' directions. Double stranded DNA fragments were separated on agarose gels.

EXAMPLE 1

Parvovirus B19 Nucleic Acid Extraction for PCR

Human serum samples that had previously tested positive for human parvovirus B19 by either IgM or PCR tests were obtained from commercial sources and used to isolate DNA for subsequent PCR experiments. Samples were stored at −80° C. until used.

DNA was extracted from 0.2 mL of serum using the QIAamp DNA Blood Mini Kit (QIAGEN, Valencia, Calif.) following the manufacturer's specifications with the following considerations. Carrier DNA was added to the lysis buffer to enhance nucleic acid binding and yield. In particular, an amount of 5.6 $\mu$g per sample of poly-adenylic acid 5' (Sigma, St. Louis, Mo.) or poly-dA (Roche, Indianapolis, Ind.) was added. Additionally, parvovirus B19 DNA was eluted with 200 $\mu$L of buffer AE (Qiagen) instead of water.

EXAMPLE 2

Detection of Parvovirus B19 Nucleic Acid-positive Samples by PCR

Two different PCR procedures were used to amplify parvovirus B19 fragments. One method, described in detail below, was used to amplify fragments of approximately 700 bp, 370 bp and 214 bp (see, FIG. 1). High Fidelity Expand PCR (Roche) was used to amplify fragments of approximately 4.7 kb. The approximately 700 bp fragment corresponds to nucleotide positions 2936–3635 of the parvovirus B19 genome described in Shade et al., *J. Virol.* (1986) 58:921–936. The approximately 370 bp occurs within the 700 bp fragment at nucleotide positions 3073–3442. The approximately 4.7 kb fragment is a 4677 nucleotide fragment corresponding to nucleotide positions 217–4893 of Shade et al., *J. Virol.* (1986) 58:921–936.

In order to amplify the B19 fragments of approximately 700 bp, 370 bp and 214 bp, the primers shown in Table 1 were used.

TABLE 1

| Primer | Sequence | PCR product | Genomic region |
|---|---|---|---|
| VP-5 | AGGAAGTTTGCCGGAAGTTC (SEQ ID NO:36) | 370 bp | VP1 |
| VP-3 | GTGCTGAAACTCTAAAGGTG (SEQ ID NO:37) | 370 bp | VP1 |
| VP2-5 | GACATGGATATGAAAAGCCTGAAG (SEQ ID NO:38) | 214 bp | VP1/VP2 |
| VP2-3 | GTTGTTCATATCTGGTTAAGTACT (SEQ ID NO:39) | 214 bp | VP1/VP2 |
| K-1sp | ATAAATCCATATACTCATT (SEQ ID NO:40) | 700 bp | VP1/VP2 |
| K-2sp | CTAAAGTATCCTGACCTTG (SEQ ID NO:41) | 700 bp | VP1/VP2 |

For this experiment, PCR was performed in a final volume of 100 μL using 2 μL of purified parvovirus B19 DNA (purified as described above), 0.2 mM of each deoxy nucleotide triphosphate and 1.25 units of Pfu DNA polymerase (Stratagene, La Jolla, Calif.). The amplification profile involved denaturation at 94° C. for 2 min., primer annealing at 37° C. for 3 min. and extension at 72° C. for 3 min. for 35 cycles. A 3-min. preincubation at 94° C. to ensure initial denaturation and a final 7-min. incubation at 72° C. to ensure the full extension of fragments preceded and followed, respectively, the 35 PCR cycles. PCR products were electrophoresed on 7% polyacrylamide gels, stained with ethidium bromide and visualized under an UV source. Purification of amplified fragments was carried out using the QiaQuick PCR purification kit (QIAGEN). Nested PCR to amplify the 370 bp B19 fragment was performed when the 700 bp band was not visualized on the polyacrylamide gels. The 700 bp DNA material was used for the nested PCR using primers shown in Table 1.

High Fidelity Expand PCR (Roche) was used to amplify the parvovirus B19 fragment of 4.7 kb as follows. The High Fidelity Expand PCR kit (Roche) and primers Hicks-5 (5'CCCGCCTTATGCAAATGGGCAG3') (SEQ ID NO:42) and Hicks-3 (5'TTGTGTTAGGCTGTCTTATAGG3') (SEQ ID NO:43) were used following the vendor's recommendations. Amplification conditions were 94° C. for 1 min., 50° C. for 2 min. and 68° C. for 4 min. for 35 or 45 cycles. A pre-incubation at 94° C. for 2 min. and a post incubation at 75° C. for 7 min. were also included. The PCR products were separated on 1% agarose gels and purified using the PCR Purification kit (Promega, Madison, Wis.).

EXAMPLE 3

Cloning of Parvovirus B19 DNA Fragments

The PCR fragments were cloned into TOPO-TA vectors (Invitrogen, Carlsbad, Calif.). Cloning into these vectors is highly facilitated when the amplified DNA contains a single deoxyadenosine (A) at its 3' end. Accordingly, a catalytic reaction to add the 3' (A) overhead was used. The reaction mix contained 1.25 mM of dATP, 0.5 units of Taq polymerase (Perkin Elmer, Boston, Mass.) and proceeded at 72° C. for 15 min.

PCR fragments were cloned into the pCR2.1-TOPO vector using Invitrogen's TA cloning kit (TOPO™ TA Cloning$^R$ Kit with One Shot TOP10 Electrocompetent Cells) following the manufacturer's specifications. Bacterial cells were incubated at 37° C. on Luria Broth plates containing ampicillin at 100 μg/ml, 0.66 mM IPTG and 0.033% X-Gal. A number of white colonies were inoculated in 4 mL of Luria-Broth ampicillin (100 μg/ml ) and incubated overnight at 37° C. with shaking. Three mL of the overnight cultures were used to prepare plasmid DNA using the QIAprep Miniprep kit (QIAGEN). Recombinant clones were identified by restriction enzyme analysis with EcoRI (New England and Biolabs) and 7% polyacryamide or 1% agarose gel electrophresis as described above.

In order to determine the DNA sequences of the clones, large amounts of plasmids from recombinant clones were prepared as above and the DNA suspended in TE (10 mM Tris-HCl, pH 8.0, 1 mM EDTA) at 0.2 mg/ml. Nucleotide sequence determination of the parvovirus B19 fragments was performed using an Applied Biosystems Model 373 (or Model 377) DNA Sequencer system.

FIGS. 2A through 2U (SEQ ID NOS:1–21) depict DNA sequences from 21 parvovirus B19 isolates, purified, amplified and sequenced as described above, which correspond to nucleotide positions 2936–3635 of the parvovirus B19 genome described in Shade et al., *J. Virol.* (1986) 58:921–936 (the 700 bp fragment from FIG. 1 and described above). FIG. 2A (SEQ ID NO:1) is the sequence from isolate CH47-26; FIG. 2B (SEQ ID NO:2) is the sequence from isolate CH48-29; FIG. 2C (SEQ ID NO:3) is the sequence from isolate CH33-2; FIG. 2D (SEQ ID NO:4) is the sequence from isolate CH33-3; FIG. 2E (SEQ ID NO:5) is the sequence from isolate CH33-4; FIG. 2F (SEQ ID NO:6) is the sequence from isolate CH42-7; FIG. 2G (SEQ ID NO:7) is the sequence from isolate CH42-18; FIG. 2H (SEQ ID NO:8) is the sequence from isolate CH42-19; FIG. 2I (SEQ ID NO:9) is the sequence from isolate CH46-23; FIG. 2J (SEQ ID NO:10) is the sequence from isolate CH1-1; FIG. 2K (SEQ ID NO:11) is the sequence from isolate CH1-6; FIG. 2L (SEQ ID NO:12) is the sequence from isolate CH2-8; FIG. 2M (SEQ ID NO:13) is the sequence from isolate CH2-10; FIG. 2N (SEQ ID NO:14) is the sequence from isolate CH2-11C; FIG. 2O (SEQ ID NO:15) is the sequence from isolate CH5-13; FIG. 2P (SEQ ID NO:16) is the sequence from isolate CH7-22; FIG. 2Q (SEQ ID NO:17) is the sequence from isolate CH13-27; FIG. 2R (SEQ ID NO:18) is the sequence from isolate CH14-33; FIG. 2S (SEQ ID NO:19) is the sequence from isolate CH62-2; FIG. 2T (SEQ ID NO:20) is the sequence from isolate CH64-2; and FIG. 2U (SEQ ID NO:21) is the sequence from isolate CH67-2.

FIGS. 11A through 11Z (SEQ ID NOS:62–87) depict DNA sequences from an additional 26 parvovirus B19 isolates, purified, amplified and sequenced as described above, which correspond to nucleotide positions 2936–3635 of the parvovirus B19 genome described in Shade et al., *J. Virol.* (1986) 58:921–936 (the 700 bp fragment from FIG. 1 and described above). FIG. 11A (SEQ ID NO:62) is the sequence from isolate CH80-1; FIG. 11B (SEQ ID NO:63) is the sequence from isolate CH81-3; FIG. 11C (SEQ ID NO:64) is the sequence from isolate B19SCL1-4; FIG. 11D (SEQ ID NO:65) is the sequence from isolate B19SCL2-1; FIG. 11E (SEQ ID NO:66) is the sequence from isolate B19SCL3-1; FIG. 11F (SEQ ID NO:67) is the sequence from isolate B19SCL4-3; FIG. 11G (SEQ ID NO:68) is the sequence from isolate B19SCL5-2; FIG. 11H (SEQ ID NO:69) is the sequence from isolate B19SCL6-2; FIG. 11I (SEQ ID NO:70) is the sequence from isolate B19SCL7-3; FIG. 11J (SEQ ID NO:71) is the sequence from isolate B19SCL8-2; FIG. 11K (SEQ ID NO:72) is the sequence from isolate B19SCL9-1; FIG. 11L (SEQ ID NO:73) is the sequence from isolate B19SCL9-9; FIG. 11M (SEQ ID NO:74) is the sequence from isolate B19SCL10-2; FIG. 11N (SEQ ID NO:75) is the sequence from isolate B19SCL11-1; FIG. 11O (SEQ ID NO:76) is the sequence from isolate B19SCL12-1; FIG. 11P (SEQ ID NO:77) is the sequence from isolate B19SCL13-3; FIG. 11Q (SEQ ID NO:78) is the sequence from isolate B19SCL14-1; FIG. 11R (SEQ ID NO:79) is the sequence from isolate B19SCL15-3; FIG. 11S (SEQ ID NO:80) is the sequence from isolate B19SCL16-2; FIG. 11T (SEQ ID NO:81) is the sequence from isolate B19SCL17-1; FIG. 11U (SEQ ID NO:82) is the sequence from isolate B19SCL18-1; FIG. 11V (SEQ ID NO:83) is the sequence from isolate B19SCL19-1; FIG. 11W (SEQ ID NO:84) is the sequence from isolate B19SCL20-3; FIG. 11X (SEQ ID NO:85) is the sequence from isolate B19SCL21-3; FIG. 11Y (SEQ ID NO:86) is the sequence from isolate B19SCL22-11; FIG. 11Z (SEQ ID NO:87) is the sequence from isolate B19SCL2-14.

Sequence comparisons revealed approximately 98% to 99.5% sequence homology of this 700 bp sequence between the various isolates.

FIGS. 3A–3C (SEQ ID NO:22) show the sequence for the approximately 4.7 kbp PCR fragment shown in FIG. 1 and described above from parvovirus B19 clone 2-B1. The sequence depicted in the figures is a 4677 nucleotide fragment corresponding to nucleotide positions 217–4893 of Shade et al., *J. Virol.* (1986) 58:921–936. The sequence depicted contains the parvovirus B19 full-length open reading frame which encodes NS1, VP1 and VP2, plus additional 5' and 3' untranslated sequences. The fragment sequenced contained an additional nucleotide in the 5' non-coding region between nucleotide position 367 and 368 of the B19 sequence reported by Shade et al., *J. Virol.* (1986) 58:921–936.

FIGS. 4A–4C (SEQ ID NO:23) show the sequence for the approximately 4.7 kbp PCR fragment shown in FIG. 1 from parvovirus B19 clone 2-B6. The sequence is a 4677 nucleotide fragment corresponding to nucleotide positions 217–4893 of Shade et al., *J. Virol.* (1986) 58:921–936. The sequence depicted contains the parvovirus B19 full-length open reading frame which encodes NS1, VP1 and VP2, plus additional 5' and 3' untranslated sequences. The fragment sequenced contained an additional nucleotide in the 5' non-coding region between nucleotide position 367 and 368 of the B19 sequence reported by Shade et al., *J. Virol.* (1986) 58:921–936.

EXAMPLE 4

Cloning and Expression of Parvovirus B19 NS1, VP1 and VP2 Recombinant Proteins Fragments encoding NS1, VP1 and VP2 (see FIG. 1) were amplified using the 4.7 kb fragment of parvovirus B19 cloned in pCR2.1-TOPO (described above). In particular, PCR primers (see below) were designed to PCR out the NS1, VP1, and VP2 regions of parvovirus B19. To facilitate the cloning of these regions into yeast expression vectors, XbaI, HindIII and SalI restriction sites were introduced in the primers as required.

The primers used to clone and amplify parvovirus B19 fragments for yeast expression of NS1, VP1 and VP2 recombinant proteins were based on the sequences obtained above and were as follows:

```
NS1-5 (sense primer)
5'ATACTCTCTAGACAAAACAAAATGGAGCTATTTAGAGGGGTGCTTCAAGTTTCT3'    (SEQ ID NO:44)

NS1-3 (anti-sense primer)
5'GAGTATGTCGACTTACTCATAATCTACAAAGCTTTGCAATCCAGACAG3'          (SEQ ID NO:45)

VP1-5SN (sense primer)
5'ATACTCAAGCTTACAAAACAAAATGAGTAAAGAAAGTGGCAAATGGTGGGAAAGT3'   (SEQ ID NO:46)

VPALL-3 (anti-sense primer)
5'GAGTATGTCGACTTACAATGGGTGCACACGGCTTTTGGCTGTCCACAATTC3'       (SEQ ID NO:47)

VP2-5SN (sense primer)
5'ATACTCAAGCTTACAAAACAAAATGACTTCAGTTAATTCTGCAGAAGCCAGCACT3'.  (SEQ ID NO:48)
```

PCR primers were synthesized, purified and suspended in 300 $\mu$L of $dH_2O$ and their optical densities at 260 nm determined. The reaction mix contained 0.25 ng of template, 100 pmol of each primer, 10 $\mu$L of 1.25 mM of each dNTP and 1 unit of Taq polymerase (Perkin Elmer, Boston, Mass.) in a final volume of 50 $\mu$L. Amplification conditions were 94° C. for 1 min., 50° C. for 2 min. and 68° C. for 4 min. for 35 cycles. A 7-min. post-incubation at 75° C. was added to ensure the full extension of fragments. Aliquots of 5 $\mu$L were used to check PCR synthesis by electrophoresis on 1% agarose gels. The entire PCR product was then electrophoresed and fragments exhibiting the expected sizes were purified from the gels using the PCR Purification kit (Promega) following the vendor's recommendations. Approximately 0.8 $\mu$g of purified PCR DNA was digested with the appropriate restriction enzymes (Roche) for 3 h at 37° C. and the products were further purified using the Promega PCR Purification kit.

Plasmid pBS24.1 was used for heterologous expression of the parvovirus B19 recombinant proteins. This yeast expression vector contains 2$\mu$ sequences and inverted repeats (IR) for autonomous replication in yeast, the $\alpha$-factor terminator to ensure transcription termination, and the yeast leu2-d and URA3 for selection. The ColE1 origin of replication and the β-lactamase gene are also present for propagation and selection in *E. coli* (Pichuantes et al. (1996) "Expression of Heterologous Gene Products in Yeast." In: *Protein Engineering: A Guide to Design and Production*, Chapter 5. J. L. Cleland and C. Craik, eds., Wiley-Liss, Inc., New York, N.Y. pp. 129–161. Plasmid pBS24.1 was digested with BamHI/SalI and dephosphorylated with 10 units of calf intestine alkaline phosphatase (Boheringer Manheim, Indianapolis, Ind.) under the conditions recommended by the vendor. The digested and purified PCR fragments were mixed with BamHI/SalI digested pBS24.1 and with a DNA fragment containing the yeast hybrid promoter ADH2/GAPDH (Cousens et al., *Gene* (1987) 61:265–275) digested with either BamHI/SfuI or a BamHI/HindIII, depending on the restriction sites present in the PCR fragments to be cloned. Ligation was carried out with the Roche Rapid Ligation kit and protocol. The ligation mix was then used to transform *E. coli* HB101 competent cells and transformants were selected in Luria-Broth plates containing ampicillin at 100 μg/ml after an overnight incubation at 37° C. Several colonies of each transformation were picked and inoculated in 3 mL of Luria-Broth with ampicillin at 100 μg/ml and incubated at 37° C. with shaking overnight.

Plasmid DNA was prepared using 1.5 mL of cultures and the QIAprep Miniprep kit (QIAGEN). Recombinant clones were identified by analytical restriction enzyme analysis with BamHI-SalI. Large-scale preparations of recombinant plasmids were made to perform sequencing to confirm the nucleotide sequence of the cloned parvovirus B19 fragments.

Yeast expression plasmids exhibiting the expected sequence for NS1, VP1 and VP2 were used for yeast transformation as follows. Competent *Saccharomyces cerevisiae* AD3 cells [Mat a, trp1+, ura3-52, prb1-1122, pep4-3, prc1-407, [cir$^0$],::pDM15(pGAP/ADR1::G418$^R$)], leu2 (ΔAD)] were transformed with plasmid DNAs encoding for NS1, VP1 or VP2, cloned as described above. Selection of yeast recombinants was achieved by two rounds of uracil-deficient plates followed by one round of leucine-deficient plates after incubation at 30° C. for 48–72 hours. Cultures were then grown in leucine-deficient media and then in YEP supplemented with 2% glucose (Pichuantes et al., *Proteins: Struct. Funct. Genet*. (1989) 6:324–337) for 48 h before checking expression of the recombinant proteins.

The sequences for the various proteins from two different isolates are shown in FIGS. 5–10. In particular, FIGS. 5A (SEQ ID NO:24) and 5B (SEQ ID NO:25) show the NS1 nucleotide and protein sequences, respectively, from parvovirus B19 clone 2-B 1. FIGS. 6A (SEQ ID NO:26) and 6B (SEQ ID NO:27) show the VP1 nucleotide and protein sequences, respectively, from parvovirus B19 clone 2-B1. FIGS. 7A (SEQ ID NO:28) and 7B (SEQ ID NO:29) show the VP2 nucleotide and protein sequences, respectively, from parvovirus B19 clone 2-B1. FIGS. 8A (SEQ ID NO:30) and 8B (SEQ ID NO:31) show the NS1 nucleotide and protein sequences, respectively, from parvovirus B19 clone 2-B6. FIGS. 9A (SEQ ID NO:32) and 9B (SEQ ID NO:33) show the VP1 nucleotide and protein sequences, respectively, from parvovirus B19 clone 2-B6. FIGS. 10A (SEQ ID NO:34) and 10B (SEQ ID NO:35) show the VP2 nucleotide and protein sequences, respectively, from parvovirus B19 clone 2-B6.

EXAMPLE 5

Detection and Quantitation of Parvovirus B19 DNA by TaqMan™

A sensitive diagnostic method for the detection of parvovirus B19 infection was designed as follows. In particular, TaqMan™ PCR technology was used to detect and quantitate parvovirus B19 DNA. Quantitative PCR requires efficient extraction of nucleic acid. The volume of plasma/serum used for DNA extraction also influences the sensitivity of detection. Two approaches were used to isolate nucleic acid from 0.5 ml of plasma/serum. In particular, DNA was extracted by (a) binding to silica; and (b) annealing to target-specific oligonucleotides.

(a) Isolation of Nucleic Acid by Binding to Silica.

In the presence of high concentrations of chaotropic salt such as guanidinium isothiocyanate, nucleic acids bind to silica. Small sized nucleic acids bind more efficiently to silica under conditions of acidic pH. The bound nucleic acids are efficiently eluted in low salt, alkaline pH buffer at high temperatures. The substitution of magnetized silica for regular silica greatly facilitates washing and elution steps of nucleic acid isolation. A magnetic base was used to capture the nucleic acid-bound silica particles, thus eliminating centrifugations required to sediment regular silica particles. The lysis buffer used was from Organon-Teknika (Durham, N.C.). This lysis buffer contains guanidinium isothiocyanate to solubilize proteins and inactivate RNases and DNases. The detergent Triton X-100 further facilitates the process of solubilization and disintegration of cell structure and nuclear proteins, thus releasing nucleic acid. The lysis reagent was acidified to enhance nucleic acid binding, and 50 μl of alkaline elution buffer was used to elute the bound nucleic acid. Following nucleic acid isolation, the presence of parvovirus DNA was determined by performing TaqMan™ PCR, as described below.

(b) Isolation of Nucleic Acid by Annealing to Target-specific Oligonucleotides.

Although use of magnetized silica greatly facilitates rapid and easy handling during the washing and elution steps, isolation of nucleic acid is still laborious and time consuming. Therefore one-step capture of specific nucleic acid target from plasma or serum using magnetic beads was used. In order to make this applicable for a wide variety of viral nucleic acid capture tests, generic magnetic beads coupled with oligo dT were used. Sera-Mag magnetic oligo (dT) beads (Seradyn, Indianapolis, Ind.) with an oligo dT length of 14mers were used in combination with Capture oligonucleotides containing 20 poly A's at 3' end contiguous with the parvovirus-specific sequence used (designated at the end of the sequence specified below).

The antisense capture oligonucleotides used were derived from the 700 bp fragment and were as follows:

VSPC1- AAAAAAAAAAAAAAAAAAAAAATCCTTAACAGCAATTTCTGATA (nt 3492-3514) (*) (SEQ ID NO:49)

VSPC2- AAAAAAAAAAAAAAAAAAAAACGCCCTGTAGTGCTGTCAG (nt 3549-3568) (SEQ ID NO:50)

VSPC3- AAAAAAAAAAAAAAAAAAAAATATACCCAAATAGGAAGTTCTG (nt 3639-3660) (SEQ ID NO:51)

VSPC4- AAAAAAAAAAAAAAAAAAAAATAAAATGCTGATTCTTCACTTGC (nt 3737-3759) (SEQ ID NO:52)

VSPC5- AAAAAAAAAAAAAAAAAAAAATGCTGTACCTCCTGTACCTA (nt 3789-3808) (SEQ ID NO:53)

VSPC6- AAAAAAAAAAAAAAAAAAAAAAGCCCTCTAAATTTTCTGGG (nt 3838-3857) (SEQ ID NO:54)

VSPC7- AAAAAAAAAAAAAAAAAAAAACTCCTAATGTGTCAGGAACC (nt 3910-3929) (SEQ ID NO:55)

(*) Nucleotide numbers are according to Shade et al., J. Virol. (1986) 58:921-936.

The magnetic beads were suspended in Novagen lysis buffer (Madison, Wis.) and a series of seven capture oligonucleotides (VSPC1–VSPC7, described above) were tested individually or in combination, to capture parvovirus B19 DNA from a panel obtained from the FDA Center for Biologic Evaluation and Research, U.S. Department of Health and Human Services (FDA-CBER).

(c) Washing the Beads with a Wash Buffer.

Following capture, the beads were washed with a buffer containing 10 mM Hepes buffered to pH 7.5 in 0.3 M NaCl., and 0.5% NP-40. After treatment of serum with lysis buffer, hybridization, magnetic adsorption of beads, and removal of lysis buffer, 1.5 ml of the wash buffer was added to the beads. Following the usual vortexing, magnetic adsorption, and removal of the wash buffer, the beads were washed a second time in 0.5 ml of the same buffer, so that the magnetic beads can be compacted, for easy suspension in 100 ml of Universal PCR buffer containing all the reagents for the Taqman assay. The beads with the captured DNA were transferred to a TaqMan™ plate for detection by TaqMan™ PCR as described below. Several oligonucleotide combinations were efficient at capturing B19 as detected by TaqMan™ assay.

In particular, the TaqMan™ technology amplifies captured target nucleic acid as DNA amplicons. An alternative is amplifying the captured target as RNA. For this, amplification oligonucleotides consisted of a parvovirus B19-specific primer with a T7 promoter sequence, in order to generate RNA amplicons using T7 RNA polymerase. Three amplification primers (VSA1–A3, described below), derived from the 700 bp sequence corresponding to nucleotides 2936–3635 of the parvovirus B19 genome described in Shade et al., *J. Virol.* (1986) 58:921–936 were tested for their ability to amplify. The primers were as follows:

Sense strand amplification primers

VSA1- AATTCTAATACGACTCACTATAGGGAGAAGGCCATATACTCATTGGACTGT (nt 2942-2961) (SEQ ID NO:56)

VSA2- AATTCTAATACGACTCACTATAGGGAGAAGGCCAGAGCACCATTATAA (nt 3272-3288) (SEQ ID NO:57)

VSA3- AATTCTAATACGACTCACTATAGGGAGAAGGCACAATGCCAGTGGAAA (nt 3317-3333) (SEQ ID NO:58)

VSP2- GTGCTGAAACTCTAAAGGT (Anti-sense Primer-nt 3424-3442) (SEQ ID NO:59)

RNamplifire kit (Qiagen) reagents were used to examine amplification efficiency using 50 copies of the parvovirus DNA as target in a final volume of 20 mLs. The amplification primers were tested individually or in combination using VSP2 as the second primer. Following one hour incubation at 42° C. as recommended by the manufacturer, an aliquot of the amplified material was diluted 100 fold, for detection by the TaqMan™ assay to assess the efficiency of the amplification primers. A combination of two amplification primers, VSA2 and VSA3 with VSP2, was highly efficient at generating RNA amplicons.

The sensitivity of the TaqMan™ assay, the suitability of the PCR primers and the optimum reaction conditions were established using plasmid DNA containing the 4.7 kb fragment described above. This fragment includes the VP1 region, as well as the NS1 and VP2 regions (see, FIG. 1). PCR amplification primers derived from the VP1 region, as detailed below, were used. The numbering is relative to Shade et al., *J. Virol.* (1986) 58:921–936. X represents 5'-fluorescein phosphoramidite and Z represents DABCYL-dT, both obtained from Glen Research Corporation, Sterling, Va. The numbers designated to the right of the sequence refer to the nucleotides in the primers from the parvovirus B19 sequence.

VSP1- GGAGGCAAAGGTTTGCA (Sense Primer-nt 3334-3350) (SEQ ID NO:60)

VSP2- GTGCTGAAACTCTAAAGGT (Anti-sense Primer-nt 3424-3442) (SEQ ID NO:59)

VSPPR1- XCCCATGGAGATATTTAGATTZ (Probe-nt 3379-3398) (SEQ ID NO:61)

Vpara 8: TCCATATGACCCAGAGCACCA (nt 3262-3282) (SEQ ID NO 88)

Vpara 9: TTTCCACTGGCATTGTGGC (Anti-sense Primer-nt 3315-3333) (SEQ ID NO:89)

Vpara 10: X TAAGGTGTTTTCTCCCGCAGCGAGT Z, where X is Fam and Z is Tamra. (nt 3286-3310) (SEQ ID NO:93)

The plasmid DNA concentration was estimated spectrophotometrically, and serial dilution was performed to obtain 5,000–10 copies/20 μl. The reaction mix in a final volume of 50 μl contained 20 μl sample, 1× Gold Taq amplification buffer (Perkin Elmer) with 3.2 mM $MgCl_2$, 300 μM each of dNTPs, 1 pmol each of the amplification primers, 0.4 pmol of the probe, and 1 unit of AmpliTaq enzyme. The reaction conditions included 10 min at 95° C. to activate the enzyme followed by 45 cycles of 30 secs at 95° C., alternating with 60° C. in an ABI 7700 Sequence Detector.

Using the primer pair VSP1 and VSP2 which generated a 109 bp PCR product and the probe VSPPR1, as few as 10 copies/assay were detectable. Since the sample volume was 20 μL in a final volume of 50 μLs, this suggests that plasma samples containing as few as 50 copies/ml of parvovirus B19 DNA could be extracted and detected by TaqMan™ technology. Since parvovirus is a high titer virus, plasma/serum volumes of 50 μL could be extracted and used for analysis.

Using the FDA-CBER parvovirus B19 DNA positive sample ($10^6$ copies/ml) TaqMan™ technology detected as few as 50 copies per assay. In an attempt to correlate the nucleic acid and immunotiter, the viral DNA load was quantitated in several antibody-positive samples.

Accordingly, novel human parvovirus B19 sequences and detection assays using these sequences have been disclosed. From the foregoing, it will be appreciated that, although specific embodiments of the invention have been described herein for purposes of illustration, various modifications may be made without deviating from the spirit and scope thereof.

What is claimed is:

1. A method for detecting human parvovirus B19 in a biological sample, the method comprising:

isolating nucleic acids from a biological sample suspected of containing human parvovirus wherein the nucleic acids are isolated from the biological sample by a method comprising (i) contacting a solid support comprising magnetic beads that comprise capture nucleic acids associated therewith with the biological sample under hybridizing conditions wherein target nucleic acid strands, if present in the biological sample, hybridize with the capture nucleic acids, and (ii) separating the solid support from the sample;

amplifying the isolated nucleic acids using a sense and an antisense primer wherein (a) the sense primer consists of SEQ ID NO:88;

(b) the antisense primer consists of SEQ ID NO:89; and detecting the presence of the amplified nucleic acids as an indication of the presence of human parvovirus B19 in the sample, wherein amplifying uses a fluorogenic 5' nuclease assay using the sense primer and the antisense primer and detecting is done using at least one probe comprising a detectable label.

2. The method of claim 1, wherein the capture nucleic acids further comprise a homopolymer chain to link the capture nucleic acids to the solid support.

3. The method of claim 2, wherein the homopolymer chain is a polyA chain.

4. The method of claim 3, wherein the capture nucleic acids comprise the oligonucleotide of SEQ ID NO:55 or a nucleotide sequence having at least 90% sequence identity to SEQ ID NO:55.

5. The method of claim 1, wherein the detectable label is a fluorescent label selected from the group consisting of 6-carboxyfluorescein (6-FAM), tetramethyl rhodamine (TAMRA), and 2', 4', 5', 7',-tetrachloro-4-7-dichlorofluorescein (TET).

6. The method of claim 5, wherein the probe further comprises detectable labels at the 5'-end and at the 3'-end.

7. The method of claim 1, wherein an internal control sequence is present.

8. The method of claim 7, wherein the internal control sequence is derived from the nucleotide sequence of SEQ ID NO:92.

9. The method of claim 8, further comprising a detectably labeled probe sequence for the internal control sequence.

10. The method of claim 4, wherein the capture nucleic acids comprise the oligonucleotide of SEQ ID NQ:55.

11. The method of claim 10, wherein the capture nucleic acids comprise the oligonucleotide of SEQ ID NO:55 and one or more of the oligonucleotides of SEQ ID NOS:49–54.

12. The method of claim 11, wherein the capture nucleic acids comprise the oligonucleotides of SEQ ID NOS:49 and 55.

13. The method of claim 11, wherein the capture nucleic acids comprise the oligonucleotides of SEQ ID NOS:50 and 55.

14. The method of claim 11, wherein the capture nucleic acids comprise the oligonucleotides of SEQ ID NOS:51 and 55.

15. The method of claim 11, wherein the capture nucleic acids comprise the oligonucleotides of SEQ ID NOS:52 and 55.

16. The method of claim 11, wherein the capture nucleic acids comprise the oligonucleotides of SEQ ID NOS:53 and 55.

17. The method of claim 11, wherein the capture nucleic acids comprise the oligonucleotides of SEQ ID NOS:54 and 55.

18. The method of claim 11, wherein the capture nucleic acids comprise the oligonucleotides of SEQ ID NOS:49, 52, 53 and 55.

19. The method of claim 1, wherein the capture nucleic acids comprises the oligonucleotide of SEQ ID NO:55 and one or more of the oligonucleotides of SEQ ID NOS:49–54.

20. The method of claim 19, wherein the capture nucleic acids comprises the oligonucleotides of SEQ ID NOS:49, 52, 53 and 55.

* * * * *

SEQUENCE LISTING

<160> NUMBER OF SEQ ID NOS: 93

<210> SEQ ID NO 1
<211> LENGTH: 700
<212> TYPE: DNA
<213> ORGANISM: Artificial Sequence
<220> FEATURE:
<223> OTHER INFORMATION: Description of Artificial Sequence: isolate CH47-26

<400> SEQUENCE: 1

```
ataaatccat atactcattg gactgtagca gatgaagagc ttttaaaaaa tataaaaaat     60
gaaactgggt ttcaagcaca agtagtaaaa gactacttta ctttaaaagg tgcagctgcc    120
cctgtggccc attttcaagg aagtttgccg gaagttcccg cttacaacgc ctcagaaaaa    180
tacccaagca tgacttcagt taattctgca gaagccagca ctggtgcagg aggggggggc    240
agtaatcctg ttaaaagcat gtggagtgag gggcccactt ttagtgccaa ctctgtaact    300
tgtacatttt ccagacagtt tttaattcca tatgacccag agcaccatta taaggtgttt    360
tctcccgcag caagtagctg ccacaatgcc agtggaaagg aggcaaaggt ttgcaccatt    420
agtcccataa tgggatactc aaccccatgg agatatttag attttaatgc tttaaatttg    480
ttttttttcac ctttagagtt tcagcattta attgaaaact atggaagtat agctcctgat    540
gctttaactg taaccatatc agaaattgct gttaaggatg ttacagacaa aactggaggg    600
ggagtacaag ttactgacag cactaccggg cgcctatgca tgttagtaga ccatgaatac    660
aagtacccat atgtgttagg gcaaggtcag gatactttag                          700
```

-continued

<210> SEQ ID NO 2
<211> LENGTH: 700
<212> TYPE: DNA
<213> ORGANISM: Artificial Sequence
<220> FEATURE:
<223> OTHER INFORMATION: Description of Artificial Sequence: isolate
CH48-29

<400> SEQUENCE: 2
ataaatccat atactcattg gactgtagca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaacaa 180
tacccaagca tgacttcagt taattctgca gaagccagca ctggtgcagg agggggtggc 240
agtaatcctg ccaaaagcat gtggagtgag gggggccactt ttactgccaa ctctgtaact 300
tgtacatttt ccagacagtt tttaattcca tatgacccag agcaccatta taaggtgttt 360
tctcccgcag ctagtagctg ccacaatgcc agtggaaagg aggcaaaggt ttgcaccatt 420
agtcccataa tgggatactc aactccatgg agatatttag attttaatgc tttaaattta 480
tttttttcac ctttagagtt tcagcaccta attgaaaatt atggaagtat agctcctgat 540
gatttaactg taaccatatc agaaattgct gttaaggatg ttacagacaa aactggaggg 600
ggggtacagg ttactgacag cactacaggg cgcctatgcc tgttagtaga ccatgaatac 660
aagtacccat atgtgttagg gcaaggtcag gatactttag 700

<210> SEQ ID NO 3
<211> LENGTH: 700
<212> TYPE: DNA
<213> ORGANISM: Artificial Sequence
<220> FEATURE:
<223> OTHER INFORMATION: Description of Artificial Sequence: isolate
CH33-2

<400> SEQUENCE: 3
ataaatccat atactcattg gactgtagca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaacaa 180
tacccaagca tgacttcagt taattctgca gaagccagca ctggtgcagg agggggtggc 240
agtaatcctg ccaaaagcat gtggagtgag gggggccactt ttactgccaa ctctgtaact 300
tgtacatttt ccagacagtt tttaattcca tatgacccag agcaccatta taaggtgttt 360
tctcccgcag ctagtagctg ccacaatgcc agtggaaagg aggcaaaggt ttgcaccatt 420
agtcccataa tgggatactc aactccatgg agatatttag attttaatgc tttaaattta 480
tttttttcac ctttagagtt tcagcaccta attgaaaatt atggaagtat agctcctgat 540
gatttaactg taaccatatc agaaattgct gttaaggatg ttacagacaa aactggaggg 600
ggggtacagg ttactgacag cactacaggg cgcctatgct tgttagtaga ccatgaatac 660
aagtacccat atgtgttagg gcaaggtcag gatactttag 700

<210> SEQ ID NO 4
<211> LENGTH: 700
<212> TYPE: DNA
<213> ORGANISM: Artificial Sequence
<220> FEATURE:
<223> OTHER INFORMATION: Description of Artificial Sequence: isolate
CH33-3

<400> SEQUENCE: 4

-continued

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaca    180

tacccaagca tgacttcagt taattctgca gaagccagca ctggtgcagg agggggtggc    240

agtaatcctg ccaaaagcat gtggagtgag gggccactt ttactgccaa ctctgtaact    300

tgtacatttt ccagacagtt tttaattcca tatgacccag agcaccatta taaggtgttt    360

tctcccgcag ctagtagctg ccacaatgcc agtggaaagg aggcaaaggt ttgcaccatt    420

agtcccataa tgggatactc aactccatgg agatatttag attttaatgc tttaaattta    480

ttttttcac ctttagagtt tcagcaccta attgaaaatt atggaagtat agctcctgat    540

gatttaactg taaccatatc agaaattgct gttaaggatg ttacagacaa aactggaggg    600

ggggtacagg ttactgacag cactacaggg cgcctatgcc tgttagtaga ccatgaatac    660

aagtacccat atgtgttagg gcaaggtcag gatactttag                          700
```

```
<210> SEQ ID NO 5
<211> LENGTH: 700
<212> TYPE: DNA
<213> ORGANISM: Artificial Sequence
<220> FEATURE:
<223> OTHER INFORMATION: Description of Artificial Sequence: isolate
      CH33-4

<400> SEQUENCE: 5

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg agggggtggc    240

agtaatcctg ccaaaagcat gtggagtgag gggccactt ttactgccaa ctctgtaact    300

tgtacatttt ccagacagtt tttaattcca tatgacccag agcaccatta taaggtgttt    360

tctcccgcag ctagtagctg ccacaatgcc agtggaaagg aggcaaaggt ttgcaccatt    420

agtcccataa tgggatactc aactccatgg agatatttag attttaatgc tttaaattta    480

ttttttcac ctttagagtt tcagcaccta attgaaaatt atggaagtat agctcctgat    540

gatttaactg taaccatatc agaaattgct gttaaggatg ttacagacaa aactggaggg    600

ggggtacagg ttactgacag cactacaggg cgcctatgcc tgttagtaga ccatgaatac    660

aagtacccat atgtgttagg gcaaggtcag gatactttag                          700
```

```
<210> SEQ ID NO 6
<211> LENGTH: 700
<212> TYPE: DNA
<213> ORGANISM: Artificial Sequence
<220> FEATURE:
<223> OTHER INFORMATION: Description of Artificial Sequence: isolate
      CH42-7

<400> SEQUENCE: 6

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg agggggggc    240
```

-continued

```
agtaatcctg tcaaaagcat gtggagtgag ggggccactt ttagtgccaa ctctgtaact    300

tgtacatttt ccaggcagtt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacagacaa aactggaggg    600

ggggtacagg ttactgacag cactacaggg cgcctatgca tgttagtaga ccatgaatac    660

aagtacccat atgtgttagg gcaaggtcag gatactttag                         700
```

```
<210> SEQ ID NO 7
<211> LENGTH: 700
<212> TYPE: DNA
<213> ORGANISM: Artificial Sequence
<220> FEATURE:
<223> OTHER INFORMATION: Description of Artificial Sequence: isolate
      CH42-18

<400> SEQUENCE: 7

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tcaaaagcat gtggagtgag ggggccactt ttagtgccaa ctctgtaact    300

tgtacatttt ccagacagtt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacagacaa aactggaggg    600

ggggtgcagg ttactgacag cactacaggg cgcctatgca tgttagtaga ccatgaatac    660

aagtacccat atgtgttagg gcaaggtcag gatactttag                         700


<210> SEQ ID NO 8
<211> LENGTH: 700
<212> TYPE: DNA
<213> ORGANISM: Artificial Sequence
<220> FEATURE:
<223> OTHER INFORMATION: Description of Artificial Sequence: isolate
      CH42-19

<400> SEQUENCE: 8

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tcaaaagcat gtggagtgag ggggccactt ttagtgccaa ctctgtaact    300

tgtacatttt ccagacagtt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540
```

-continued gctttaactg taaccatatc agaaattgct gttaaggatg ttacagacaa aactggaggg 600
ggggtacagg ttactgacag cactacaggg cgcctatgca tgttagtaga ccatgaatac 660
aagtacccat atgtgttagg gcaaggtcag gatactttag 700

<210> SEQ ID NO 9
<211> LENGTH: 700
<212> TYPE: DNA
<213> ORGANISM: Artificial Sequence
<220> FEATURE:
<221> NAME/KEY: misc_feature
<222> LOCATION: (76)
<223> OTHER INFORMATION: where 'n' is A, T, C or G
<220> FEATURE:
<223> OTHER INFORMATION: Description of Artificial Sequence: isolate CH46-23

<400> SEQUENCE: 9
attaatccat atactcattg gactgtagca gatgaagagc ttttaaaaaa tataaaaaat 60
gaaactgggt ttcaancaca agtagtaaaa gactacttta ctttaaaagg tgcagctgcc 120
cctgtggccc attttcaagg aagtttgccg gaagttcccg cttacaacgc ctcagaaaaa 180
tacccaagca tgacttcagt taattctgca gaagccagca ctggtgcagg aggggggggc 240
agtaatcctg tcaaaagcat gtggagtgag gggccactt ttagtgccaa ctctgtaact 300
tgtacatttt ccaggcagtt tttaattcca tatgacccag agcaccatta taaggtgttt 360
tctcccgcag caagtagctg ccacaatgcc agtggaaagg aggcaaaggt ttgcaccatt 420
agtcccataa tgggatactc aaccccatgg agatatttag attttaatgc tttaaattta 480
tttttttcac ctttagagtt tcagcactta attgaaaatt atggaagtat agctcctgat 540
gctttaactg taaccatatc agaaattgct gttaaggatg ttacagacaa aactggaggg 600
ggggtacagg ttactgacag cactacaggg cgcctatgca tgttagtaga ccatgaatac 660
aagtacccat atgtgttagg gcaaggtcag gatactttag 700

<210> SEQ ID NO 10
<211> LENGTH: 700
<212> TYPE: DNA
<213> ORGANISM: Artificial Sequence
<220> FEATURE:
<223> OTHER INFORMATION: Description of Artificial Sequence: isolate CH1-1

<400> SEQUENCE: 10
ataaatccat atactcattg gactgtagca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaaaaa 180
tacccaagca tgacttcagt taattctgca gaagccagca ctggtgcagg aggggggggc 240
agtaatcctg tcaaaagcat gtggagtgag gggccactt ttagtgccaa ctctgtaact 300
tgtacatttt ccagacagtt tttaattcca tatgacccag agcaccatta taaggtgttt 360
tctcccgcag caagtagctg ccacaatgcc agtggaaagg aggcaaaggt ttgcaccatt 420
agtcccataa tgggatactc aaccccatgg agatatttag attttaatgc tttaaattta 480
tttttttcac ctttagagtt tcagcactta attgaaaatt atggaagtat agctcctgat 540
gctttaactg taaccatatc agaaattgct gttaaggatg ttacagacaa aactggaggg 600
ggggtacagg ttactgacag cactacaggg cgcctatgca tgttagtaga ccatgaatac 660

-continued

```
aagtacccat atgtgttagg gcaaggtcag gatactttag                        700


<210> SEQ ID NO 11
<211> LENGTH: 700
<212> TYPE: DNA
<213> ORGANISM: Artificial Sequence
<220> FEATURE:
<223> OTHER INFORMATION: Description of Artificial Sequence: isolate
      CH1-6

<400> SEQUENCE: 11

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tcaaaagcat gtggagtgag gggccactt ttagtgccaa ctctgtaact     300

tgtacatttt ccagacagtt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacagacaa aactggaggg    600

ggggtacagg ttactgacag cactacaggg cgcctatgca tgttagtaga ccatgaatac    660

aagtacccat atgtgttagg gcaaggtcag gatactttag                        700


<210> SEQ ID NO 12
<211> LENGTH: 700
<212> TYPE: DNA
<213> ORGANISM: Artificial Sequence
<220> FEATURE:
<223> OTHER INFORMATION: Description of Artificial Sequence: isolate
      CH2-8

<400> SEQUENCE: 12

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact     300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacagacaa aactggaggg    600

ggggtgcagg ttactgacag cactacaggg cgcctatgca tgttagtaga ccatgaatat    660

aagtacccat atgtgttagg gcaaggtcag gatactttag                        700


<210> SEQ ID NO 13
<211> LENGTH: 700
<212> TYPE: DNA
<213> ORGANISM: Artificial Sequence
<220> FEATURE:
<223> OTHER INFORMATION: Description of Artificial Sequence: isolate
```

CH2-10

<400> SEQUENCE: 13

| | | | | | |
|---|---|---|---|---|---|
| ataaatccat | atactcattg | gactgtagca | gatgaagagc | ttttaaaaaa | tataaaaaat | 60 |
| gaaactgggt | ttcaagcaca | agtagtaaaa | gactacttta | ctttaaaagg | tgcagctgcc | 120 |
| cctgtggccc | attttcaagg | aagtttgccg | gaagttcccg | cttacaacgc | ctcagaaaaa | 180 |
| tacccaagca | tgacttcagt | taattctgca | gaagccagca | ctggtgcagg | agggggggc | 240 |
| agtaatcctg | tgaaaagcat | gtggagtgag | ggggccactt | ttagtgccaa | ctctgtaact | 300 |
| tgtacatttt | ccagacaatt | tttaattcca | tatgacccag | agcaccatta | taaggtgttt | 360 |
| tctcccgcag | caagtagctg | ccacaatgcc | agtggaaagg | aggcaaaggt | ttgcaccatt | 420 |
| agtcccataa | tgggatactc | aaccccatgg | agatatttag | attttaatgc | tttaaattta | 480 |
| ttttttcac | ctttagagtt | tcagcactta | attgaaaatt | atggaagtat | agctcctgat | 540 |
| gctttaactg | taaccatatc | agaaattgct | gttaaggatg | ttacagacag | aactggaggg | 600 |
| ggggtgcagg | ttactgacag | cactacaggg | cgcctatgca | tgttagtaga | ccatgaatat | 660 |
| aagtacccat | atgtgttagg | gcaaggtcag | gatactttag | | | 700 |

<210> SEQ ID NO 14
<211> LENGTH: 700
<212> TYPE: DNA
<213> ORGANISM: Artificial Sequence
<220> FEATURE:
<223> OTHER INFORMATION: Description of Artificial Sequence: isolate CH2-11C

<400> SEQUENCE: 14

| | | | | | |
|---|---|---|---|---|---|
| ataaatccat | atactcattg | gactgtagca | gatgaagagc | ttttaaaaaa | tataaaaaat | 60 |
| gaaactgggt | ttcaagcaca | agtagtaaaa | gactactttA | ctttaaaagg | tgcagctgcc | 120 |
| cctgtggccc | attttcaagg | aagtttgccg | gaagttcccg | cttacaacgc | ctcagaaaaa | 180 |
| tacccaagca | tgacttcagt | taattctgca | gaagccagca | ctggtgcagg | agggggggc | 240 |
| agtaatcctg | tgaaaagcat | gtggagtgag | ggggccactt | ttagtgccaa | ctctgtaact | 300 |
| tgtacatttt | ccagacaatt | tttaattcca | tatgacccag | agcaccatta | taaggtgttt | 360 |
| tctcccgcag | caagtagctg | ccacaatgcc | agtggaaagg | aggcaaaggt | ttgcaccatt | 420 |
| agtcccataa | tgggatactc | aaccccatgg | agatatttag | attttaatgc | tttaaattta | 480 |
| ttttttcac | ctttagagtt | tcagcactta | attgaaaatt | atggaagtat | agctcctgat | 540 |
| gctttaactg | taaccatatc | agaaattgct | gttaaggatg | ttacagacaa | aactggaggg | 600 |
| ggggtgcagg | ttactgacag | cactacaggg | cgcctatgca | tgttagtaga | ccatgaatat | 660 |
| aagtacccat | atgtgttagg | gcaaggtcag | gatactttag | | | 700 |

<210> SEQ ID NO 15
<211> LENGTH: 699
<212> TYPE: DNA
<213> ORGANISM: Artificial Sequence
<220> FEATURE:
<223> OTHER INFORMATION: Description of Artificial Sequence: isolate CH5-13

<400> SEQUENCE: 15

| | | | | | |
|---|---|---|---|---|---|
| ctaaatccat | atactcattg | gactgtagca | gatgaagagc | ttttaaaaaa | tataaaaaat | 60 |
| gaaactgggt | ttcaagcaca | agtagtaaaa | gactactttA | ctttaaaagg | tgcagctgcc | 120 |
| cctgtggccc | attttcaagg | aagtttgccg | gaagttcccg | cttacaacgc | ctcagaaaaa | 180 |

-continued

```
tacccaagca tgacttcagt taattctgca gaagccagca ctggtgcagg aggggggggc    240

agtaatcctg ttaaaagcat gtggagtgag ggggccactt ttagtgccaa ctctgtaact    300

tgtacatttt ccagacagtt tttaattcca tatgacccag agcaccatta taaggtgttt    360

tctcccgcag caagtagctg ccacaatgcc agtggaaaag aggcaaaggt ttgcactatt    420

agtcccataa tgggatactc aaccccatgg agatatttag attttaatgc tttaaattta    480

tttttttcac ctttagagtt tcagcactta attgaaaatt atggcagtat agctcctgat    540

gctttaactg taaccatatc agaaattgct gttaaggatg ttacagacaa aactggaggg    600

ggggtacagg ttactgacag cactacaggg cgcctatgca tgttagtaga ccatgaatac    660

aagtacccaa tgtgttaggg caaggtcagg atactttag                           699
```

<210> SEQ ID NO 16
<211> LENGTH: 700
<212> TYPE: DNA
<213> ORGANISM: Artificial Sequence
<220> FEATURE:
<223> OTHER INFORMATION: Description of Artificial Sequence: isolate CH7-22

<400> SEQUENCE: 16

```
ataaatccat gtactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg ttaaaagcat gtggagtgag ggggccactt ttagtgccaa ctctgtaact    300

tgtacatttt ccagacagtt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaatttg    480

tttttttcac ctttagagtt tcagcattta attgaaaact atggaagtat agctcctgat    540

gctttaactg taaccatatc agaaattgct gttaaggatg ttacagacaa aactggaggg    600

ggagtacaag ttactgacag cactaccggg cgcctatgca tgttagtaga ccatgaatac    660

aagtacccat atgtgttagg gcaaggtcag gatactttag                         700
```

<210> SEQ ID NO 17
<211> LENGTH: 700
<212> TYPE: DNA
<213> ORGANISM: Artificial Sequence
<220> FEATURE:
<223> OTHER INFORMATION: Description of Artificial Sequence: isolate CH13-27

<400> SEQUENCE: 17

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaattctg tcaaaagcat gtggagtgag ggggccactt ttagtgctaa ctctgtaact    300

tgtacatttt ccagacagtt tttaattcca tatgacccag agcaccatta taaggtgttt    360

tctcccgcag cgagtagctg ccacaatgcc agtggaaagg aggcaaaggt ttgcaccatc    420
```

-continued

```
agtcccataa tgggatactc aaccccatgg agatatttag attttaatgc tttaaattta    480

ttttttttcac ctttagagtt tcagcactta attgaaaatt atggaagtat agctcctgat    540

gctttaactg taaccatatc agaaattgct gttaaggatg ttacagacaa aactggaggg    600

ggggtacagg ttactgacag cactacaggg cgcctatgca tgttagtaga ccatgaatac    660

aagtacccat atgtgttagg gcaaggtcag gatactttag                         700
```

<210> SEQ ID NO 18
<211> LENGTH: 699
<212> TYPE: DNA
<213> ORGANISM: Artificial Sequence
<220> FEATURE:
<223> OTHER INFORMATION: Description of Artificial Sequence: isolate CH14-33

<400> SEQUENCE: 18

```
ataaatccat atactcattg gactgtggca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggga    240

gtaatcctgt taaaagcatg tggagtgagg gggccacttt tagtgccaac tctgtaactt    300

gtacattttc cagacagttt ttaattccat atgacccaga gcaccattat aaggtgtttt    360

ctcccgcagc aagtagctgc cacaatgcca gtggaaaaga ggcaaaggtt tgcaccatta    420

gtcccataat gggatactca accccatgga gatatttaga ttttaatgct ttaaatttat    480

tttttcacc tttagagttt cagcacttaa ttgaaaatta tggtagtata gctcctgatg    540

ctttaactgt aaccatatca gaaattgctg ttaaagatgt tacagacaaa actggagggg    600

gggtacaggt tactgacagc actacagggc gcctatgcat gttagtggac catgaataca    660

agtacccata tgtgttaggg caaggtcagg atactttag                          699
```

<210> SEQ ID NO 19
<211> LENGTH: 700
<212> TYPE: DNA
<213> ORGANISM: Artificial Sequence
<220> FEATURE:
<223> OTHER INFORMATION: Description of Artificial Sequence: isolate CH62-2

<400> SEQUENCE: 19

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcaat taattctgca gaagccagca ctggtgcagg aggggggggc    240

agtaatcctg tcaaaagcat gtggagtgag gggggccactt ttagtgccaa ctctgtaact    300

tgtacakttt ccagacagtt tttaattcca tatgacccag agcaccatta taaggtgttt    360

tctcccgcag ccagtagctg ccacaatgcc agtggaaagg aggcaaaggt ttgcaccatt    420

agtcccataa tgggatactc aaccccatgg agatatttag attttaatgc tttaaattta    480

ttttttttcac ctttagagtt tcagcactta attgaaaatt atggaagtat agctcctgat    540

gctttaactg taaccatatc agaaattgct gttaaggatg ttacagacaa aactggaggg    600

ggggtacagg ttactgacag cactacaggc cgcctatgca tgttagtaga ccatgaatac    660

aagtacccat atgtgttagg gcaaggtcag gatactttag                         700
```

-continued

<210> SEQ ID NO 20
<211> LENGTH: 700
<212> TYPE: DNA
<213> ORGANISM: Artificial Sequence
<220> FEATURE:
<223> OTHER INFORMATION: Description of Artificial Sequence: isolate CH64-2

<400> SEQUENCE: 20
ataaatccat atactcattg gactgtagca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaaaaa 180
tacccaagca tgacttcagt taattctgca gaagccagca ctggtgcagg aggggggggc 240
agtaatcctg ttaaaagcat gtggagtgag gggccactt ttagtgccaa ctctgtaact 300
tgtacatttt ccagacagtt tttaattcca tatgacccag agcaccatta taaggtgttt 360
tcgcccgcag caagtagctg ccacaatgcc agtggaaagg aggcaaaggt ttgcaccatt 420
agtcccataa tgggatactc aaccccatgg agatacttag attttaatgc tttaaattta 480 ttttttcac ctttagagtt tcagcactta attgaaaatt atggaagtat agctcctgat 540
gctttaactg taaccatatc agaaattgct gttaaggatg ttacggacaa aactggaggg 600
ggggtgcagg ttactgacag cactacaggg cgcctatgca tgttagtaga ccatgaatac 660
aagtacccat atgtgttagg gcaaggtcag gatactttag 700

<210> SEQ ID NO 21
<211> LENGTH: 700
<212> TYPE: DNA
<213> ORGANISM: Artificial Sequence
<220> FEATURE:
<223> OTHER INFORMATION: Description of Artificial Sequence: isolate CH67-2

<400> SEQUENCE: 21
ataaatccat atactcattg gactgtggca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaaaaa 180
tacccaagca tgacttcagt taattctgca gaagccagca ctggtgcagg aggggggggg 240
agtaatcctg ttaaaagcat gtggagtgag gggccactt ttagtgccaa ctctgtaact 300
tgtacatttt ccagacagtt tttaattcca tatgacccag agcaccatta taaggtgttt 360
tctcccgcag caagtagctg ccacaatgcc agtggaaaag aggcaaaggt ttgcaccatt 420
agtcccataa tgggatactc aaccccatgg agatatttag attttaatgc tttaaattta 480 ttttttcac ctttagagtt tcagcactta attgaaaatt atggaagtat agctcctgat 540
gctttaactg taaccatatc agaaattgct gttaaagatg ttacagacaa aactggaggg 600
ggggtacagg ttactgacag cactacaggg cgcctatgca tgttagtgga ccatgaatac 660
aagtacccat atgtgttagg gcaaggtcag gatactttag 700

<210> SEQ ID NO 22
<211> LENGTH: 4678
<212> TYPE: DNA
<213> ORGANISM: Artificial Sequence
<220> FEATURE:
<223> OTHER INFORMATION: Description of Artificial Sequence: 4.7 kbp PCR fragment from parvovirus B19 clone 2-B1

-continued

<400> SEQUENCE: 22
cccgccttat gcaaatgggc agccatctta agtgttttac tataatttta ttggtcagtt 60
ttgtaacggt taaaatgggc ggagcgtagg caaggactac agtatatata gcacagcact 120
gccgcagctc tttctttctg ggctgctttt ttcctggact tacttgctgt tttttgtgag 180
ctaactaaca ggtatttata ctacttgtta acatactaac atggagctat ttagaggggt 240
gcttcaagtt tcttctaatg ttctggactg tgctaacgat aactggtggt gctctttact 300
ggatttagac acttctgact gggaaccact aactcatact aacagactaa tggcaatata 360
cttaagcagt gtggcttcta agcttgactt tactgggggg ccactagcag ggtgcttgta 420
ctttttttcaa gtagaatgta acaaatttga agaaggctat catattcatg tggttattgg 480
ggggccaggg ttaaacccca gaaacctcac agtgtgtgta gaggggttat ttaataatgt 540
actttatcac cttgtaactg aaaatctgaa gctaaaattt ttgccaggaa tgactacaaa 600
aggcaaatac tttagagatg gagagcagtt tatagaaaac tatttaatga aaaaaatacc 660
tttaaatgtt gtatggtgtg ttactaatat tgatggacat atagatacct gtatttctgc 720
tacttttaga aagggagctt gccatgccaa gaaaccccgc atcaccacag ccataaatga 780
tactagtact gatgctgggg agtctagcgg cacaggggca gaggttgtgc catttaatgg 840
gaagggaact aaggctagca taaagtttca aactatggta aactggttgt gtgaaaacag 900
agtgtttaca gaggataagt ggaaactagt tgactttaac cagtacactt tactaagcag 960
tagtcacagt ggaagttttc aaattcaaag tgcactaaaa ctagcaattt ataaagcaac 1020
taatttagtg cctactagca catttttatt gcatacagac tttgagcaag ttatgtgtat 1080
taaaaacaat aaaattgtta aattgttact ttgtcaaaac tatgaccccc tattagtggg 1140
gcagcatgtg ttaaagtgga ttgataaaaa atgtggcaag aaaaacacac tgtggtttta 1200
tgggccgcca agtacaggga aaacaaactt ggcaatggcc attgctaaaa gtgttccagt 1260
atatggcatg gttaactgga ataatgaaaa ctttccattt aatgatgtag caggaaaaag 1320
cttggtggtc tgggatgaag gtattattaa gtctacaatt gtagaagctg caaaagccat 1380
tttaggcggg caacccacca gggtagatca aaaaatgcgt ggaagtgtag ctgtgcctgg 1440
agtacctgtg gttataacca gcaatggtga cattactttt gttgtaagcg ggaacactac 1500
aacaactgta catgctaaag ccttaaaaga gcgcatggta aagttaaact ttactgtaag 1560
atgcagccct gacatggggt tactaacaga ggctgatgta caacagtggc ttacatggtg 1620
taatgcacaa agctgggacc actatgaaaa ctgggcaata aactacactt ttgatttccc 1680
tggaattaat gcagatgccc tccacccaga cctccaaacc accccaattg tcacagacac 1740
cagtatcagc agcagtggtg gtgaaagctc tgaagaactc agtgaaagca gctttttttaa 1800
cctcatcacc ccaggcgcct ggaacactga aaccccgcgc tctagtacgc ccatccccgg 1860
gaccagttca ggagaatcat ctgtcggaag cccagtttcc tccgaagttg tagctgcatc 1920
gtgggaagaa gccttctaca cacctttggc agaccagttt cgtgaactgt tagttggggt 1980
tgattatgtg tgggacggtg taaggggttt acctgtctgt tgtgtgcaac atattaacaa 2040
tagtggggga ggcttgggac tttgtcccca ttgcattaat gtaggggctt ggtataatgg 2100
atggaaattt cgagaattta ccccagattt ggtgcgatgt agctgccatg tgggagcttc 2160
taatcccttt tctgtgctaa cctgcaaaaa atgtgcttac ctgtctggat tgcaaagctt 2220
tgtagattat gagtaaagaa agtggcaaat ggtgggaaag tgatgataaa tttgctaaag 2280

-continued

```
ctgtgtatca gcaatttgtg gaattttatg aaaaggttac tggaacagac ttagagctta   2340
ttcaaatatt aaaagatcat tataatattt ctttagataa tcccctagaa aacccatcct   2400
ctttgtttga cttagttgct cgtattaaaa ataaccttaa aaactctcca gacttatata   2460
gtcatcattt tcaaagtcat ggacagttat ctgaccaccc ccatgcctta tcatccagta   2520
gcagtcatgc agaacctaga ggagaagatg cagtattatc tagtgaagac ttacacaagc   2580
ctgggcaagt tagcgtacaa ctacccggta ctaactatgt tgggcctggc aatgagctac   2640
aagctgggcc cccgcaaagt gctgttgaca gtgctgcaag gattcatgac tttaggtata   2700
gccaactggc taagttggga ataaatccat atactcattg gactgtagca gatgaagagc   2760
ttttaaaaaa tataaaaaat gaaactgggt ttcaagcaca agtagtaaaa gactacttta   2820
ctttaaaagg tgcagctgcc cctgtggccc attttcaagg aagtttgccg gaagttcccg   2880
cttacaacgc ctcagaaaaa tacccaagca tgacttcagt taattctgca gaagccagca   2940
ctggtgcagg agggggggc agtaatcctg tgaaaagcat gtggagtgag gggccactt   3000
ttagtgccaa ctctgtaact tgtacatttt ccagacaatt tttaattcca tatgacccag   3060
agcaccatta taaggtgttt tctcccgcag caagtagctg ccacaatgcc agtggaaagg   3120
aggcaaaggt ttgcaccatt agtcccataa tgggatactc aaccccatgg agatatttag   3180
attttaatgc tttaaattta ttttttcac ctttagagtt tcagcactta attgaaaatt   3240
atggaagtat agctcctgat gctttaactg taaccatatc agaaattgct gttaaggatg   3300
ttacggacaa aactggaggg ggggtgcagg ttactgacag cactacaggg cgcctatgca   3360
tgttagtaga ccatgaatat aagtacccat atgtgttagg gcaaggtcaa gatactttag   3420
ccccagaact tcctatttgg gtatactttc cccctcaata cgcttactta acagtaggag   3480
atgttaacac acaaggaatt tctggagaca gcaaaaaatt ggcaagtgaa gaatcagcat   3540
tttatgtttt ggaacacagt tcttttcagc ttttaggtac aggaggtaca gcaactatgt   3600
cttataagtt tcctccagtg cccccagaaa atttagaggg ctgcagtcaa cacttttatg   3660
aaatgtacaa cccccttatac ggatcccgct taggggttcc tgacacatta ggaggtgacc   3720
caaaatttag atctttaaca catgaagacc atgcaattca gccccaaaac ttcatgccag   3780
ggccactagt aaactcagtg tctacaaagg agggagacag ctctagtact ggagctggaa   3840
aagccttaac aggccttagc acaggtacct ctcaaaacac tagaatatcc ttacgccctg   3900
ggccagtgtc tcagccgtac caccactggg acacagataa atatgtcaca ggaataaatg   3960
ccatttctca tggtcagacc acttatggta acgctgaaga caaagagtat cagcaaggag   4020
tgggtagatt tccaaatgaa aaagaacagc taaaacagtt acagggttta aacatgcaca   4080
cctactttcc caataaagga acccagcaat atacagatca aattgagcgc cccctaatgg   4140
tgggttctgt atggaacaga agagcccttc actatgaaag ccagctgtgg agtaaaattc   4200
caaatttaga tgacagtttt aaaactcagt ttgcagcctt aggaggatgg ggtttgcatc   4260
agccacctcc tcaaatattt ttaaaaatat taccacaaag tgggccaatt ggaggtatta   4320
aatcaatggg aattactacc ttagttcagt atgccgtggg aattatgaca gtaaccatga   4380
catttaaatt ggggccccgt aaagctacgg gacggtggaa tcctcaacct ggagtgtatc   4440
cccgcacgc agcaggtcat ttaccatatg tactatatga ccccacagct acagatgcaa   4500
aacaacacca cagacatgga tatgaaaagc ctgaagaatt gtggacagcc aaaagccgtg   4560
tgcacccatt gtaaacactc cccaccgtgc cctcagccag gatgtgtaac taaacgccca   4620
ccagtaccac ccagactgta cctgcccccct cctataccta taagacagcc taacacaa     4678
```

-continued

<210> SEQ ID NO 23
<211> LENGTH: 4678
<212> TYPE: DNA
<213> ORGANISM: Artificial Sequence
<220> FEATURE:
<223> OTHER INFORMATION: Description of Artificial Sequence: 4.7 kbp
PCR fragment from parvovirus B19 clone 2-B6

<400> SEQUENCE: 23

```
cccgccttat gcaaatgggc agccatctta agtgttttac tataatttta ttggtcagtt     60
ttgtaacggt taaaatgggc ggagcgtagg caaggactac agtatatata gcacagcact    120
gccgcagctc tttctttctg ggctgctttt ttcctggact tacttgctgt tttttgtgag    180
ctaactaaca ggtatttata ctacttgtta acatactaac atggagctat ttagaggggt    240
gcttcaagtt tcttctaatg ttctggactg tgctaacgat aactggtggt gctctttact    300
ggatttagac acttctgact gggaaccact aactcatact aacagactaa tggcaatata    360
cttaagcagt gtggcttcta agcttgactt tactgggggg ccactagcag ggtgcttgta    420
ctttttttcaa gtagaatgta acaaatttga agaaggctat catattcatg tggttattgg    480
ggggccaggg ttaaacccca gaaacctcac agtgtgtgta gaggggttat ttaataatgt    540
actttatcac cttgtaactg aaaatctgaa gctaaaattt ttgccaggaa tgactacaaa    600
aggcaaatac tttagagatg gagagcagtt tatagaaaac tatttaatga aaaaaatacc    660
tttaaatgtt gtatggtgtg ttactaatat tgatggacat atagatacct gtatttctgc    720
tacttttaga aagggagctt gccatgccaa gaaaccccgc atcaccacag ccataaatga    780
tactagtact gatgctgggg agtctagcgg cacaggggca gaggttgtgc catttaatgg    840
gaagggaact aaggctagca taaagtttca aactatggta aactggttgt gtgaaaacag    900
agtgtttaca gaggataagt ggaaactagt tgactttaac cagtacactt tactaagcag    960
tagtcacagt ggaagttttc aaattcaaag tgcactaaaa ctagcaattt ataaagcaac   1020
taatttagtg cctactagca catttttatt gcatacagac tttgagcaag ttatgtgtat   1080
taaagacaat aaaattgtta aattgttact ttgtcaaaac tatgaccccc tattagtggg   1140
gcagcatgtg ttaaagtgga ttgataaaaa atgtggcaag aaaaacacac tgtggtttta   1200
tggaccgcca agtacaggga aaacaaactt ggcaatggcc attgctaaaa gtgttccagt   1260
atatggcatg gttaactgga ataatgaaaa ctttccattt aatgatgtag caggaaaaag   1320
cttggtggtc tgggatgaag gtattattaa gtctacaatt gtagaagctg caaaagccat   1380
tttaggcggg caacccacca gggtagatca aaaaatgcgt ggaagtgtag ctgtgcctgg   1440
agtacccgtg gttataacca gcaatggtga cattactttt gttgtaagcg ggaacactac   1500
aacaactgta catgctaaag ccttaaaaga gcgcatggta aagttaaact ttactgtaag   1560
atgcagccct gacatggggt tactaacaga ggctgatgta caacagtggc ttacatggtg   1620
taatgcacaa agctgggacc actatgaaaa ctgggcaata aactacactt ttgatttccc   1680
tggaattaat gcagatgccc tccacccaga cctccaaacc accccaattg tcacagacac   1740
cagtatcagc agcagtggtg gtgaaagctc tgaagaactc agtgaaagca gctttttttaa   1800
cctcatcacc ccaggcgcct ggaacactga aaccccgcgc tctagtacgc ccatccccgg   1860
gaccagttca ggagaatcat ctgtcggaag cccagtttcc tccgaagttg tagctgcatc   1920
gtgggaagaa gccttctaca cacctttggc agaccagttt cgtgaactgt tagttggggt   1980
tgattatgtg tgggacggtg taaggggttt acctgtctgt tgtgtgcaac atattaacaa   2040
```

-continued

```
tagtggggga ggcttgggac tttgtcccca ttgcattaat gtaggggctt ggtataatgg   2100
atggaaattt cgagaattta ccccagattt ggtgcgatgt agctgccatg tgggagcttc   2160
taatcccttt tctgtgctaa cctgcaaaaa atgtgcttac ctgtctggat tgcaaagctt   2220
tgtagattat gagtaaagaa agtggcaaat ggtgggaaag tgatgataaa tttgctaaag   2280
ctgtgtatca gcaatttgtg gaattttatg aaaaggttac tggaacagac ttagagctta   2340
ttcaaatatt aaaagatcat tataatattt ctttagataa tcccctagaa aacccatcct   2400
ctttgtttga cttagttgct cgtattaaaa ataaccttaa aaactctcca gacttatata   2460
gtcatcattt tcaaagtcat ggacagttat ctgaccaccc ccatgcctta tcatccagta   2520
gcagtcatgc agaacctaga ggagaagatg cagtattatc tagtgaagac ttacacaagc   2580
ctgggcaagt tagcgtacaa ctacccggta ctaactatgt tgggcctggc aatgagctac   2640
aagctgggcc cccgcaaagt gctgttgaca gtgctgcaag gattcatgac tttaggtata   2700
gccaactggc taagttggga ataaatccat atactcattg gactgtagca gatgaagagc   2760
ttttaaaaaa tataaaaaat gaaactgggt ttcaagcaca agtagtaaaa gactacttta   2820
ctttaaaagg tgcagctgcc cctgtggccc attttcaagg aagtttgccg gaagttcccg   2880
cttacaacgc ctcagaaaaa tacccaagca tgacttcagt taattctgca gaagccagca   2940
ctggtgcagg agggggggc agtaatcctg tgaaaagcat gtggagtgag gggccactt   3000
ttagtgccaa ctctgtaact tgtacatttt ccagacaatt tttaattcca tatgacccag   3060
agcaccatta taaggtgttt tctcccgcag caagtagctg ccacaatgcc agtggaaagg   3120
aggcaaaggt ttgcaccatt agtcccataa tgggatactc aaccccatgg agatatttag   3180
attttaatgc tttaaattta ttttttcac ctttagagtt tcagcactta attgaaaatt   3240
atggaagtat agctcctgat gctttaactg taaccatatc agaaattgct gttaaggatg   3300
ttacaaacaa aactggaggg ggggtgcagg ttactgacag cactacaggg cgcctatgca   3360
tgttagtaga ccatgaatat aagtacccat atgtgttagg gcaaggtcaa gatactttag   3420
ccccagaact tcctatttgg gtatactttc cccctcaata cgcttactta acagtaggag   3480
atgttaacac acaaggaatt tctggagaca gcaaaaaatt ggcaagtgaa gaatcagcat   3540
tttatgtttt ggaacacagt tcttttcagc ttttaggtac aggaggtaca gcaactatgt   3600
cttataagtt tcctccagtg cccccagaaa atttagaggg ctgcagtcaa cacttttatg   3660
aaatgtacaa cccccttatac ggatcccgct taggggttcc tgacacatta ggaggtgacc   3720
caaaatttag atctttaaca catgaagacc atgcaattca gccccaaaac ttcatgccag   3780
ggccactagt aaactcagtg tctacaaagg agggagacag ctctagtact ggagctggaa   3840
aagccttaac aggccttagc acaggtacct ctcaaaacac tagaatatcc ttacgccctg   3900
ggccagtgtc tcagccgtac caccactggg acacagataa atatgtcaca ggaataaatg   3960
ccatttctca tggtcagacc acttatggta acgctgaaga caaagagtat cagcaaggag   4020
tgggtagatt tccaaatgaa aaagaacagc taaaacagtt acagggttta aacatgcaca   4080
cctactttcc caataaagga acccagcaat atacagatca aattgagcgc cccctaatgg   4140
tgggttctgt atggaacaga agagcccttc actatgaaag ccagctgtgg agtaaaattc   4200
caaatttaga tgacagtttt aaaactcagt ttgcagcctt aggaggatgg ggtttgcatc   4260
agccacctcc tcaaatattt ttaaaaatat taccacaaag tgggccaatt ggaggtatta   4320
aatcaatggg aattactacc ttagttcagt atgccgtggg aattatgaca gtaaccatga   4380
```

-continued

```
catttaaatt ggggccccgt aaagctacgg gacggtggaa tcctcaacct ggagtgtatc   4440

ccccgcacgc agcaggtcat ttaccatatg tactatatga ccccacagct acagatgcaa   4500

aacaacacca cagacatgga tatgaaaagc ctgaagaatt gtggacagcc aaaagccgtg   4560

tgcacccatt gtaaacactc cccaccgtgc cctcagccag gatgtgtaac taaacgccca   4620

ccagtaccac ccagactgta cctgccccct cctataccta taagacagcc taacacaa     4678
```

<210> SEQ ID NO 24
<211> LENGTH: 2049
<212> TYPE: DNA
<213> ORGANISM: Artificial Sequence
<220> FEATURE:
<223> OTHER INFORMATION: Description of Artificial Sequence: NS1 from parvovirus B19 clone 2-B1

<400> SEQUENCE: 24

```
atactcttcg aacaaaacaa aatggagcta tttagagggg tgcttcaagt ttcttctaat     60

gttctggact gtgctaacga taactggtgg tgctctttac tggatttaga cacttctgac    120

tgggaaccac taactcatac taacagacta atggcaatat acttaagcag tgtggcttct    180

aagcttgact ttactggggg gccactagca gggtgcttgt acttttttca agtagaatgt    240

aacaaatttg aagaaggcta tcatattcat gtggttattg gggggccagg gttaaacccc    300

agaaacctca cagtgtgtgt agaggggtta tttaataatg tactttatca ccttgtaact    360

gaaaatctga agctaaaatt tttgccagga atgactacaa aaggcaaata ctttagagat    420

ggagagcagt ttatagaaaa ctatttaatg aaaaaaatac ctttaaatgt tgtatggtgt    480

gttactaata ttgatggaca tatagatacc tgtatttctg ctacttttag aaagggagct    540

tgccatgcca agaaaccccg catcaccaca gccataaatg atactagtac tgatgctggg    600

gagtctagcg gcacaggggc agaggttgtg ccatttaatg ggaagggaac taaggctagc    660

ataaagtttc aaactatggt aaactggttg tgtgaaaaca gagtgtttac agaggataag    720

tggaaactag ttgactttaa ccagtacact ttactaagca gtagtcacag tggaagtttt    780

caaattcaaa gtgcactaaa actagcaatt tataaagcaa ctaatttagt gcctactagc    840

acatttttat tgcatacaga ctttgagcaa gttatgtgta ttaaaaacaa taaaattgtt    900

aaattgttac tttgtcaaaa ctatgacccc ctattagtgg ggcagcatgt gttaaagtgg    960

attgataaaa aatgtggcaa gaaaaacaca ctgtggtttt atgggccgcc aagtacaggg   1020

aaaacaaact tggcaatggc cattgctaaa agtgttccag tatatggcat ggttaactgg   1080

aataatgaaa actttccatt taatgatgta gcaggaaaaa gcttggtggt ctgggatgaa   1140

ggtattatta agtctacaat tgtagaagct gcaaaagcca ttttaggcgg gcaacccacc   1200

agggtagatc aaaaaatgcg tggaagtgta gctgtgcctg gagtacctgt ggttataacc   1260

agcaatggtg acattacttt tgttgtaagc gggaacacta caacaactgt acatgctaaa   1320

gccttaaaag agcgcatggt aaagttaaac tttactgtaa gatgcagccc tgacatgggg   1380

ttactaacag aggctgatgt acaacagtgg cttacatggt gtaatgcaca aagctgggac   1440

cactatgaaa actgggcaat aaactacact tttgatttcc ctggaattaa tgcagatgcc   1500

ctccacccag acctccaaac caccccaatt gtcacagaca ccagtatcag cagcagtggt   1560

ggtgaaagct ctgaagaact cagtgaaagc agctttttta acctcatcac cccaggcgcc   1620

tggaacactg aaaccccgcg ctctagtacg cccatccccg ggaccagttc aggagaatca   1680

tctgtcggaa gcccagtttc ctccgaagtt gtagctgcat cgtgggaaga agccttctac   1740
```

-continued

```
acacctttgg cagaccagtt tcgtgaactg ttagttgggg ttgattatgt gtgggacggt   1800

gtaaggggtt tacctgtctg ttgtgtgcaa catattaaca atagtggggg aggcttggga   1860

ctttgtcccc attgcattaa tgtaggggct tggtataatg gatggaaatt tcgagaattt   1920

accccagatt tggtgcgatg tagctgccat gtgggagctt ctaatccctt ttctgtgcta   1980

acctgcaaaa aatgtgctta cctgtctgga ttgcaaagct ttgtagatta tgagtaagtc   2040

gacatactc                                                           2049


<210> SEQ ID NO 25
<211> LENGTH: 671
<212> TYPE: PRT
<213> ORGANISM: Artificial Sequence
<220> FEATURE:
<223> OTHER INFORMATION: Description of Artificial Sequence: NS1 amino
      acid from parvovirus B19 clone 2-B1

<400> SEQUENCE: 25

Met Glu Leu Phe Arg Gly Val Leu Gln Val Ser Ser Asn Val Leu Asp
  1               5                  10                  15

Cys Ala Asn Asp Asn Trp Trp Cys Ser Leu Leu Asp Leu Asp Thr Ser
             20                  25                  30

Asp Trp Glu Pro Leu Thr His Thr Asn Arg Leu Met Ala Ile Tyr Leu
         35                  40                  45

Ser Ser Val Ala Ser Lys Leu Asp Phe Thr Gly Gly Pro Leu Ala Gly
     50                  55                  60

Cys Leu Tyr Phe Phe Gln Val Glu Cys Asn Lys Phe Glu Glu Gly Tyr
 65                  70                  75                  80

His Ile His Val Val Ile Gly Gly Pro Gly Leu Asn Pro Arg Asn Leu
                 85                  90                  95

Thr Val Cys Val Glu Gly Leu Phe Asn Asn Val Leu Tyr His Leu Val
            100                 105                 110

Thr Glu Asn Leu Lys Leu Lys Phe Leu Pro Gly Met Thr Thr Lys Gly
        115                 120                 125

Lys Tyr Phe Arg Asp Gly Glu Gln Phe Ile Glu Asn Tyr Leu Met Lys
    130                 135                 140

Lys Ile Pro Leu Asn Val Val Trp Cys Val Thr Asn Ile Asp Gly His
145                 150                 155                 160

Ile Asp Thr Cys Ile Ser Ala Thr Phe Arg Lys Gly Ala Cys His Ala
                165                 170                 175

Lys Lys Pro Arg Ile Thr Thr Ala Ile Asn Asp Thr Ser Thr Asp Ala
            180                 185                 190

Gly Glu Ser Ser Gly Thr Gly Ala Glu Val Val Pro Phe Asn Gly Lys
        195                 200                 205

Gly Thr Lys Ala Ser Ile Lys Phe Gln Thr Met Val Asn Trp Leu Cys
    210                 215                 220

Glu Asn Arg Val Phe Thr Glu Asp Lys Trp Lys Leu Val Asp Phe Asn
225                 230                 235                 240

Gln Tyr Thr Leu Leu Ser Ser Ser His Ser Gly Ser Phe Gln Ile Gln
                245                 250                 255

Ser Ala Leu Lys Leu Ala Ile Tyr Lys Ala Thr Asn Leu Val Pro Thr
            260                 265                 270

Ser Thr Phe Leu Leu His Thr Asp Phe Glu Gln Val Met Cys Ile Lys
        275                 280                 285

Asn Asn Lys Ile Val Lys Leu Leu Leu Cys Gln Asn Tyr Asp Pro Leu
    290                 295                 300
```

-continued

```
Leu Val Gly Gln His Val Leu Lys Trp Ile Asp Lys Lys Cys Gly Lys
305                 310                 315                 320

Lys Asn Thr Leu Trp Phe Tyr Gly Pro Pro Ser Thr Gly Lys Thr Asn
                325                 330                 335

Leu Ala Met Ala Ile Ala Lys Ser Val Pro Val Tyr Gly Met Val Asn
            340                 345                 350

Trp Asn Asn Glu Asn Phe Pro Phe Asn Asp Val Ala Gly Lys Ser Leu
        355                 360                 365

Val Val Trp Asp Glu Gly Ile Ile Lys Ser Thr Ile Val Glu Ala Ala
    370                 375                 380

Lys Ala Ile Leu Gly Gly Gln Pro Thr Arg Val Asp Gln Lys Met Arg
385                 390                 395                 400

Gly Ser Val Ala Val Pro Gly Val Pro Val Val Ile Thr Ser Asn Gly
                405                 410                 415

Asp Ile Thr Phe Val Val Ser Gly Asn Thr Thr Thr Thr Val His Ala
            420                 425                 430

Lys Ala Leu Lys Glu Arg Met Val Lys Leu Asn Phe Thr Val Arg Cys
        435                 440                 445

Ser Pro Asp Met Gly Leu Leu Thr Glu Ala Asp Val Gln Gln Trp Leu
    450                 455                 460

Thr Trp Cys Asn Ala Gln Ser Trp Asp His Tyr Glu Asn Trp Ala Ile
465                 470                 475                 480

Asn Tyr Thr Phe Asp Phe Pro Gly Ile Asn Ala Asp Ala Leu His Pro
                485                 490                 495

Asp Leu Gln Thr Thr Pro Ile Val Thr Asp Thr Ser Ile Ser Ser Ser
            500                 505                 510

Gly Gly Glu Ser Ser Glu Glu Leu Ser Glu Ser Ser Phe Phe Asn Leu
        515                 520                 525

Ile Thr Pro Gly Ala Trp Asn Thr Glu Thr Pro Arg Ser Ser Thr Pro
    530                 535                 540

Ile Pro Gly Thr Ser Ser Gly Glu Ser Ser Val Gly Ser Pro Val Ser
545                 550                 555                 560

Ser Glu Val Val Ala Ala Ser Trp Glu Glu Ala Phe Tyr Thr Pro Leu
                565                 570                 575

Ala Asp Gln Phe Arg Glu Leu Leu Val Gly Val Asp Tyr Val Trp Asp
            580                 585                 590

Gly Val Arg Gly Leu Pro Val Cys Cys Val Gln His Ile Asn Asn Ser
        595                 600                 605

Gly Gly Gly Leu Gly Leu Cys Pro His Cys Ile Asn Val Gly Ala Trp
    610                 615                 620

Tyr Asn Gly Trp Lys Phe Arg Glu Phe Thr Pro Asp Leu Val Arg Cys
625                 630                 635                 640

Ser Cys His Val Gly Ala Ser Asn Pro Phe Ser Val Leu Thr Cys Lys
                645                 650                 655

Lys Cys Ala Tyr Leu Ser Gly Leu Gln Ser Phe Val Asp Tyr Glu
            660                 665                 670
```

<210> SEQ ID NO 26
<211> LENGTH: 2380
<212> TYPE: DNA
<213> ORGANISM: Artificial Sequence
<220> FEATURE:
<223> OTHER INFORMATION: Description of Artificial Sequence: VP1 from
      parvovirus B19 clone 2-B1

-continued

<400> SEQUENCE: 26

```
atactcaagc ttacaaaaca aaatgagtaa agaaagtggc aaatggtggg aaagtgatga     60
taaatttgct aaagctgtgt atcagcaatt tgtggaattt tatgaaaagg ttactggaac    120
agacttagag cttattcaaa tattaaaaga tcattataat atttctttag ataatcccct    180
agaaaaccca tcctctttgt ttgacttagt tgctcgtatt aaaaataacc ttaaaaactc    240
tccagactta tatagtcatc attttcaaag tcatggacag ttatctgacc acccccatgc    300
cttatcatcc agtagcagtc atgcagaacc tagaggagaa gatgcagtat tatctagtga    360
agacttacac aagcctgggc aagttagcgt acaactaccc ggtactaact atgttgggcc    420
tggcaatgag ctacaagctg ggcccccgca aagtgctgtt gacagtgctg caaggattca    480
tgactttagg tatagccaac tggctaagtt gggaataaat ccatatactc attggactgt    540
agcagatgaa gagcttttaa aaaatataaa aaatgaaact gggtttcaag cacaagtagt    600
aaaagactac tttactttaa aaggtgcagc tgcccctgtg gcccattttc aaggaagttt    660
gccggaagtt cccgcttaca acgcctcaga aaaataccca agcatgactt cagttaattc    720
tgcagaagcc agcactggtg caggaggggg gggcagtaat cctgtgaaaa gcatgtggag    780
tgagggggcc acttttagtg ccaactctgt aacttgtaca ttttccagac aatttttaat    840
tccatatgac ccagagcacc attataaggt gttttctccc gcagcaagta gctgccacaa    900
tgccagtgga aaggaggcaa aggtttgcac cattagtccc ataatgggat actcaacccc    960
atggagatat ttagatttta atgctttaaa tttatttttt tcacctttag agtttcagca   1020
cttaattgaa aattatggaa gtatagctcc tgatgcttta actgtaacca tatcagaaat   1080
tgctgttaag gatgttacgg acaaaactgg agggggggtg caggttactg acagcactac   1140
agggcgccta tgcatgttag tagaccatga atataagtac ccatatgtgt tagggcaagg   1200
tcaagatact ttagccccag aacttcctat ttgggtatac tttcccccctc aatacgctta   1260
cttaacagta ggagatgtta acacacaagg aatttctgga gacagcaaaa aattggcaag   1320
tgaagaatca gcattttatg ttttggaaca cagttctttt cagcttttag gtacaggagg   1380
tacagcaact atgtcttata agtttcctcc agtgccccca gaaaatttag agggctgcag   1440
tcaacacttt tatgaaatgt acaacccctt atacggatcc cgcttagggg ttcctgacac   1500
attaggaggt gacccaaaat ttagatcttt aacacatgaa gaccatgcaa ttcagcccca   1560
aaacttcatg ccagggccac tagtaaactc agtgtctaca aaggagggag acagctctag   1620
tactggagct ggaaaagcct taacaggcct tagcacaggt acctctcaaa acactagaat   1680
atccttacgc cctgggccag tgtctcagcc gtaccaccac tgggacacag ataaatatgt   1740
cacaggaata aatgccattt ctcatggtca gaccacttat ggtaacgctg aagacaaaga   1800
gtatcagcaa ggagtgggta gatttccaaa tgaaaaagaa cagctaaaac agttacaggg   1860
tttaaacatg cacacctact ttcccaataa aggaacccag caatatacag atcaaattga   1920
gcgcccccta atggtgggtt ctgtatggaa cagaagagcc cttcactatg aaagccagct   1980
gtggagtaaa attccaaatt tagatgacag ttttaaaact cagtttgcag ccttaggagg   2040
atggggtttg catcagccac ctcctcaaat atttttaaaa atattaccac aaagtgggcc   2100
aattggaggt attaaatcaa tgggaattac taccttagtt cagtatgccg tgggaattat   2160
gacagtaacc atgacattta aattggggcc ccgtaaagct acgggacggt ggaatcctca   2220
acctggagtg tatcccccgc acgcagcagg tcatttacca tatgtactat atgaccccac   2280
agctacagat gcaaaacaac accacagaca tggatatgaa aagcctgaag aattgtggac   2340
```

-continued

```
agccaaaagc cgtgtgcacc cattgtaagt cgacatactc                     2380


<210> SEQ ID NO 27
<211> LENGTH: 781
<212> TYPE: PRT
<213> ORGANISM: Artificial Sequence
<220> FEATURE:
<223> OTHER INFORMATION: Description of Artificial Sequence: VP1
      amino acid from parvovirus B19 clone 2-B1

<400> SEQUENCE: 27

Met Ser Lys Glu Ser Gly Lys Trp Trp Glu Ser Asp Asp Lys Phe Ala
  1               5                  10                  15

Lys Ala Val Tyr Gln Gln Phe Val Glu Phe Tyr Glu Lys Val Thr Gly
             20                  25                  30

Thr Asp Leu Glu Leu Ile Gln Ile Leu Lys Asp His Tyr Asn Ile Ser
         35                  40                  45

Leu Asp Asn Pro Leu Glu Asn Pro Ser Ser Leu Phe Asp Leu Val Ala
     50                  55                  60

Arg Ile Lys Asn Asn Leu Lys Asn Ser Pro Asp Leu Tyr Ser His His
 65                  70                  75                  80

Phe Gln Ser His Gly Gln Leu Ser Asp His Pro His Ala Leu Ser Ser
                 85                  90                  95

Ser Ser Ser His Ala Glu Pro Arg Gly Glu Asp Ala Val Leu Ser Ser
            100                 105                 110

Glu Asp Leu His Lys Pro Gly Gln Val Ser Val Gln Leu Pro Gly Thr
        115                 120                 125

Asn Tyr Val Gly Pro Gly Asn Glu Leu Gln Ala Gly Pro Pro Gln Ser
    130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser Met Thr Ser Val Asn Ser Ala Glu Ala Ser Thr Gly Ala
225                 230                 235                 240

Gly Gly Gly Gly Ser Asn Pro Val Lys Ser Met Trp Ser Glu Gly Ala
                245                 250                 255

Thr Phe Ser Ala Asn Ser Val Thr Cys Thr Phe Ser Arg Gln Phe Leu
            260                 265                 270

Ile Pro Tyr Asp Pro Glu His His Tyr Lys Val Phe Ser Pro Ala Ala
        275                 280                 285

Ser Ser Cys His Asn Ala Ser Gly Lys Glu Ala Lys Val Cys Thr Ile
    290                 295                 300

Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350
```

-continued

```
Ile Ala Val Lys Asp Val Thr Asp Lys Thr Gly Gly Gly Val Gln Val
        355                 360                 365

Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Asp Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Gln Leu
        435                 440                 445

Leu Gly Thr Gly Gly Thr Ala Thr Met Ser Tyr Lys Phe Pro Pro Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Val Asn Ser Val Ser Thr Lys Glu
        515                 520                 525

Gly Asp Ser Ser Ser Thr Gly Ala Gly Lys Ala Leu Thr Gly Leu Ser
    530                 535                 540

Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575

Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Met His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
            660                 665                 670

Gly Trp Gly Leu His Gln Pro Pro Pro Gln Ile Phe Leu Lys Ile Leu
        675                 680                 685

Pro Gln Ser Gly Pro Ile Gly Gly Ile Lys Ser Met Gly Ile Thr Thr
    690                 695                 700

Leu Val Gln Tyr Ala Val Gly Ile Met Thr Val Thr Met Thr Phe Lys
705                 710                 715                 720

Leu Gly Pro Arg Lys Ala Thr Gly Arg Trp Asn Pro Gln Pro Gly Val
                725                 730                 735

Tyr Pro Pro His Ala Ala Gly His Leu Pro Tyr Val Leu Tyr Asp Pro
            740                 745                 750

Thr Ala Thr Asp Ala Lys Gln His His Arg His Gly Tyr Glu Lys Pro
        755                 760                 765
```

-continued

```
Glu Glu Leu Trp Thr Ala Lys Ser Arg Val His Pro Leu
    770                 775                 780
```

<210> SEQ ID NO 28
<211> LENGTH: 1699
<212> TYPE: DNA
<213> ORGANISM: Artificial Sequence
<220> FEATURE:
<223> OTHER INFORMATION: Description of Artificial Sequence: VP2 from parvovirus B19 clone 2-B1

<400> SEQUENCE: 28

```
atactcaagc ttacaaaaca aaatgacttc agttaattct gcagaagcca gcactggtgc     60

aggagggggg ggcagtaatc ctgtgaaaag catgtggagt gagggggcca cttttagtgc    120

caactctgta acttgtacat tttccagaca atttttaatt ccatatgacc cagagcacca    180

ttataaggtg ttttctcccg cagcaagtag ctgccacaat gccagtggaa aggaggcaaa    240

ggtttgcacc attagtccca taatgggata ctcaacccca tggagatatt tagattttaa    300

tgctttaaat ttattttttt cacctttaga gtttcagcac ttaattgaaa attatggaag    360

tatagctcct gatgctttaa ctgtaaccat atcagaaatt gctgttaagg atgttacgga    420

caaaactgga ggggggggtgc aggttactga cagcactaca gggcgcctat gcatgttagt    480

agaccatgaa tataagtacc catatgtgtt agggcaaggt caagatactt tagccccaga    540

acttcctatt tgggtatact ttccccctca atacgcttac ttaacagtag gagatgttaa    600

cacacaagga atttctggag acagcaaaaa attggcaagt gaagaatcag cattttatgt    660

tttggaacac agttcttttc agcttttagg tacaggaggt acagcaacta tgtcttataa    720

gtttcctcca gtgcccccag aaaatttaga gggctgcagt caacactttt atgaaatgta    780

caacccctta tacggatccc gcttaggggt tcctgacaca ttaggaggtg acccaaaatt    840

tagatcttta acacatgaag accatgcaat tcagccccaa aacttcatgc cagggccact    900

agtaaactca gtgtctacaa aggagggaga cagctctagt actggagctg gaaaagcctt    960

aacaggcctt agcacaggta cctctcaaaa cactagaata tccttacgcc ctgggccagt   1020

gtctcagccg taccaccact gggacacaga taaatatgtc acaggaataa atgccatttc   1080

tcatggtcag accacttatg gtaacgctga agacaaagag tatcagcaag gagtgggtag   1140

atttccaaat gaaaaagaac agctaaaaca gttacagggt ttaaacatgc acacctactt   1200

tcccaataaa ggaacccagc aatatacaga tcaaattgag cgcccccctaa tggtgggttc  1260

tgtatggaac agaagagccc ttcactatga aagccagctg tggagtaaaa ttccaaattt   1320

agatgacagt tttaaaactc agtttgcagc cttaggagga tggggtttgc atcagccacc   1380

tcctcaaata tttttaaaaa tattaccaca aagtgggcca attggaggta ttaaatcaat   1440

gggaattact accttagttc agtatgccgt gggaattatg acagtaacca tgacatttaa   1500

attggggccc cgtaaagcta cgggacggtg gaatcctcaa cctggagtgt atcccccgca   1560

cgcagcaggt catttaccat atgtactata tgaccccaca gctacagatg caaaacaaca   1620

ccacagacat ggatatgaaa agcctgaaga attgtggaca gccaaaagcc gtgtgcaccc   1680

attgtaagtc gacatactc                                                1699
```

<210> SEQ ID NO 29
<211> LENGTH: 554
<212> TYPE: PRT
<213> ORGANISM: Artificial Sequence
<220> FEATURE:
<223> OTHER INFORMATION: Description of Artificial Sequence: VP2 amino acid from parvovirus B19 clone 2-B1

<400> SEQUENCE: 29

```
Met Thr Ser Val Asn Ser Ala Glu Ala Ser Thr Gly Ala Gly Gly Gly
  1               5                  10                  15

Gly Ser Asn Pro Val Lys Ser Met Trp Ser Glu Gly Ala Thr Phe Ser
             20                  25                  30

Ala Asn Ser Val Thr Cys Thr Phe Ser Arg Gln Phe Leu Ile Pro Tyr
         35                  40                  45

Asp Pro Glu His His Tyr Lys Val Phe Ser Pro Ala Ala Ser Ser Cys
     50                  55                  60

His Asn Ala Ser Gly Lys Glu Ala Lys Val Cys Thr Ile Ser Pro Ile
 65                  70                  75                  80

Met Gly Tyr Ser Thr Pro Trp Arg Tyr Leu Asp Phe Asn Ala Leu Asn
                 85                  90                  95

Leu Phe Phe Ser Pro Leu Glu Phe Gln His Leu Ile Glu Asn Tyr Gly
            100                 105                 110

Ser Ile Ala Pro Asp Ala Leu Thr Val Thr Ile Ser Glu Ile Ala Val
        115                 120                 125

Lys Asp Val Thr Asp Lys Thr Gly Gly Gly Val Gln Val Thr Asp Ser
    130                 135                 140

Thr Thr Gly Arg Leu Cys Met Leu Val Asp His Glu Tyr Lys Tyr Pro
145                 150                 155                 160

Tyr Val Leu Gly Gln Gly Gln Asp Thr Leu Ala Pro Glu Leu Pro Ile
                165                 170                 175

Trp Val Tyr Phe Pro Pro Gln Tyr Ala Tyr Leu Thr Val Gly Asp Val
            180                 185                 190

Asn Thr Gln Gly Ile Ser Gly Asp Ser Lys Lys Leu Ala Ser Glu Glu
        195                 200                 205

Ser Ala Phe Tyr Val Leu Glu His Ser Ser Phe Gln Leu Leu Gly Thr
    210                 215                 220

Gly Gly Thr Ala Thr Met Ser Tyr Lys Phe Pro Pro Val Pro Pro Glu
225                 230                 235                 240

Asn Leu Glu Gly Cys Ser Gln His Phe Tyr Glu Met Tyr Asn Pro Leu
                245                 250                 255

Tyr Gly Ser Arg Leu Gly Val Pro Asp Thr Leu Gly Gly Asp Pro Lys
            260                 265                 270

Phe Arg Ser Leu Thr His Glu Asp His Ala Ile Gln Pro Gln Asn Phe
        275                 280                 285

Met Pro Gly Pro Leu Val Asn Ser Val Ser Thr Lys Glu Gly Asp Ser
    290                 295                 300

Ser Ser Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
    370                 375                 380

Gln Gly Leu Asn Met His Thr Tyr Phe Pro Asn Lys Gly Thr Gln Gln
385                 390                 395                 400
```

-continued

```
Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
        435                 440                 445

Leu His Gln Pro Pro Pro Gln Ile Phe Leu Lys Ile Leu Pro Gln Ser
    450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
        515                 520                 525

Asp Ala Lys Gln His His Arg His Gly Tyr Glu Lys Pro Glu Glu Leu
    530                 535                 540

Trp Thr Ala Lys Ser Arg Val His Pro Leu
545                 550
```

<210> SEQ ID NO 30
<211> LENGTH: 2049
<212> TYPE: DNA
<213> ORGANISM: Artificial Sequence
<220> FEATURE:
<223> OTHER INFORMATION: Description of Artificial Sequence: NS1 from parvovirus B19 clone 2-B6

<400> SEQUENCE: 30

```
atactcttcg aacaaaacaa aatggagcta tttagagggg tgcttcaagt ttcttctaat     60

gttctggact gtgctaacga taactggtgg tgctctttac tggatttaga cacttctgac    120

tgggaaccac taactcatac taacagacta atggcaatat acttaagcag tgtggcttct    180

aagcttgact ttactggggg gccactagca gggtgcttgt actttttca agtagaatgt     240

aacaaatttg aagaaggcta tcatattcat gtggttattg gggggccagg gttaaacccc    300

agaaacctca cagtgtgtgt agaggggtta tttaataatg tactttatca ccttgtaact    360

gaaaatctga agctaaaatt tttgccagga atgactacaa aaggcaaata ctttagagat    420

ggagagcagt ttatagaaaa ctatttaatg aaaaaaatac ctttaaatgt tgtatggtgt    480

gttactaata ttgatggaca tatagatacc tgtatttctg ctacttttag aaagggagct    540

tgccatgcca agaaaccccg catcaccaca gccataaatg atactagtac tgatgctggg    600

gagtctagcg gcacaggggc agaggttgtg ccatttaatg ggaagggaac taaggctagc    660

ataaagtttc aaactatggt aaactggttg tgtgaaaaca gagtgtttac agaggataag    720

tggaaactag ttgactttaa ccagtacact ttactaagca gtagtcacag tggaagtttt    780

caaattcaaa gtgcactaaa actagcaatt tataaagcaa ctaatttagt gcctactagc    840

acatttttat tgcatacaga ctttgagcaa gttatgtgta ttaaagacaa taaaattgtt    900

aaattgttac tttgtcaaaa ctatgacccc ctattagtgg ggcagcatgt gttaaagtgg    960

attgataaaa aatgtggcaa gaaaaacaca ctgtggtttt atggaccgcc aagtacaggg   1020

aaaacaaact tggcaatggc cattgctaaa agtgttccag tatatggcat ggttaactgg   1080

aataatgaaa actttccatt taatgatgta gcaggaaaaa gcttggtggt ctgggatgaa   1140
```

-continued

```
ggtattatta agtctacaat tgtagaagct gcaaaagcca ttttaggcgg gcaacccacc   1200

agggtagatc aaaaaatgcg tggaagtgta gctgtgcctg gagtacccgt ggttataacc   1260

agcaatggtg acattacttt tgttgtaagc gggaacacta caacaactgt acatgctaaa   1320

gccttaaaag agcgcatggt aaagttaaac tttactgtaa gatgcagccc tgacatgggg   1380

ttactaacag aggctgatgt acaacagtgg cttacatggt gtaatgcaca aagctgggac   1440

cactatgaaa actgggcaat aaactacact tttgatttcc ctggaattaa tgcagatgcc   1500

ctccacccag acctccaaac caccccaatt gtcacagaca ccagtatcag cagcagtggt   1560

ggtgaaagct ctgaagaact cagtgaaagc agctttttta acctcatcac cccaggcgcc   1620

tggaacactg aaaccccgcg ctctagtacg cccatccccg ggaccagttc aggagaatca   1680

tctgtcggaa gcccagtttc ctccgaagtt gtagctgcat cgtgggaaga agccttctac   1740

acacctttgg cagaccagtt tcgtgaactg ttagttgggg ttgattatgt gtgggacggt   1800

gtaaggggtt tacctgtctg ttgtgtgcaa catattaaca atagtggggg aggcttggga   1860

ctttgtcccc attgcattaa tgtaggggct tggtataatg gatggaaatt tcgagaattt   1920

accccagatt tggtgcgatg tagctgccat gtgggagctt ctaatccctt ttctgtgcta   1980

acctgcaaaa aatgtgctta cctgtctgga ttgcaaagct ttgtagatta tgagtaagtc   2040

gacatactc                                                           2049
```

<210> SEQ ID NO 31
<211> LENGTH: 671
<212> TYPE: PRT
<213> ORGANISM: Artificial Sequence
<220> FEATURE:
<223> OTHER INFORMATION: Description of Artificial Sequence: NS1 amino acid from parvovirus B19 clone 2-B6

<400> SEQUENCE: 31

```
Met Glu Leu Phe Arg Gly Val Leu Gln Val Ser Ser Asn Val Leu Asp
  1               5                  10                  15

Cys Ala Asn Asp Asn Trp Trp Cys Ser Leu Leu Asp Leu Asp Thr Ser
             20                  25                  30

Asp Trp Glu Pro Leu Thr His Thr Asn Arg Leu Met Ala Ile Tyr Leu
         35                  40                  45

Ser Ser Val Ala Ser Lys Leu Asp Phe Thr Gly Gly Pro Leu Ala Gly
     50                  55                  60

Cys Leu Tyr Phe Phe Gln Val Glu Cys Asn Lys Phe Glu Glu Gly Tyr
 65                  70                  75                  80

His Ile His Val Val Ile Gly Gly Pro Gly Leu Asn Pro Arg Asn Leu
                 85                  90                  95

Thr Val Cys Val Glu Gly Leu Phe Asn Asn Val Leu Tyr His Leu Val
            100                 105                 110

Thr Glu Asn Leu Lys Leu Lys Phe Leu Pro Gly Met Thr Thr Lys Gly
        115                 120                 125

Lys Tyr Phe Arg Asp Gly Glu Gln Phe Ile Glu Asn Tyr Leu Met Lys
    130                 135                 140

Lys Ile Pro Leu Asn Val Val Trp Cys Val Thr Asn Ile Asp Gly His
145                 150                 155                 160

Ile Asp Thr Cys Ile Ser Ala Thr Phe Arg Lys Gly Ala Cys His Ala
                165                 170                 175

Lys Lys Pro Arg Ile Thr Thr Ala Ile Asn Asp Thr Ser Thr Asp Ala
            180                 185                 190
```

-continued

```
Gly Glu Ser Ser Gly Thr Gly Ala Glu Val Val Pro Phe Asn Gly Lys
        195                 200                 205

Gly Thr Lys Ala Ser Ile Lys Phe Gln Thr Met Val Asn Trp Leu Cys
    210                 215                 220

Glu Asn Arg Val Phe Thr Glu Asp Lys Trp Lys Leu Val Asp Phe Asn
225                 230                 235                 240

Gln Tyr Thr Leu Leu Ser Ser Ser His Ser Gly Ser Phe Gln Ile Gln
                245                 250                 255

Ser Ala Leu Lys Leu Ala Ile Tyr Lys Ala Thr Asn Leu Val Pro Thr
            260                 265                 270

Ser Thr Phe Leu Leu His Thr Asp Phe Glu Gln Val Met Cys Ile Lys
        275                 280                 285

Asp Asn Lys Ile Val Lys Leu Leu Leu Cys Gln Asn Tyr Asp Pro Leu
    290                 295                 300

Leu Val Gly Gln His Val Leu Lys Trp Ile Asp Lys Lys Cys Gly Lys
305                 310                 315                 320

Lys Asn Thr Leu Trp Phe Tyr Gly Pro Pro Ser Thr Gly Lys Thr Asn
                325                 330                 335

Leu Ala Met Ala Ile Ala Lys Ser Val Pro Val Tyr Gly Met Val Asn
            340                 345                 350

Trp Asn Asn Glu Asn Phe Pro Phe Asn Asp Val Ala Gly Lys Ser Leu
        355                 360                 365

Val Val Trp Asp Glu Gly Ile Ile Lys Ser Thr Ile Val Glu Ala Ala
    370                 375                 380

Lys Ala Ile Leu Gly Gly Gln Pro Thr Arg Val Asp Gln Lys Met Arg
385                 390                 395                 400

Gly Ser Val Ala Val Pro Gly Val Pro Val Val Ile Thr Ser Asn Gly
                405                 410                 415

Asp Ile Thr Phe Val Val Ser Gly Asn Thr Thr Thr Thr Val His Ala
            420                 425                 430

Lys Ala Leu Lys Glu Arg Met Val Lys Leu Asn Phe Thr Val Arg Cys
        435                 440                 445

Ser Pro Asp Met Gly Leu Leu Thr Glu Ala Asp Val Gln Gln Trp Leu
    450                 455                 460

Thr Trp Cys Asn Ala Gln Ser Trp Asp His Tyr Glu Asn Trp Ala Ile
465                 470                 475                 480

Asn Tyr Thr Phe Asp Phe Pro Gly Ile Asn Ala Asp Ala Leu His Pro
                485                 490                 495

Asp Leu Gln Thr Thr Pro Ile Val Thr Asp Thr Ser Ile Ser Ser Ser
            500                 505                 510

Gly Gly Glu Ser Ser Glu Glu Leu Ser Glu Ser Ser Phe Phe Asn Leu
        515                 520                 525

Ile Thr Pro Gly Ala Trp Asn Thr Glu Thr Pro Arg Ser Ser Thr Pro
    530                 535                 540

Ile Pro Gly Thr Ser Ser Gly Glu Ser Ser Val Gly Ser Pro Val Ser
545                 550                 555                 560

Ser Glu Val Val Ala Ala Ser Trp Glu Glu Ala Phe Tyr Thr Pro Leu
                565                 570                 575

Ala Asp Gln Phe Arg Glu Leu Leu Val Gly Val Asp Tyr Val Trp Asp
            580                 585                 590

Gly Val Arg Gly Leu Pro Val Cys Cys Val Gln His Ile Asn Asn Ser
        595                 600                 605

Gly Gly Gly Leu Gly Leu Cys Pro His Cys Ile Asn Val Gly Ala Trp
```

-continued

```
    610                 615                 620

Tyr Asn Gly Trp Lys Phe Arg Glu Phe Thr Pro Asp Leu Val Arg Cys
625                 630                 635                 640

Ser Cys His Val Gly Ala Ser Asn Pro Phe Ser Val Leu Thr Cys Lys
                645                 650                 655

Lys Cys Ala Tyr Leu Ser Gly Leu Gln Ser Phe Val Asp Tyr Glu
            660                 665                 670
```

<210> SEQ ID NO 32
<211> LENGTH: 2380
<212> TYPE: DNA
<213> ORGANISM: Artificial Sequence
<220> FEATURE:
<223> OTHER INFORMATION: Description of Artificial Sequence: VP1 from parvovirus B19 clone 2-B6

<400> SEQUENCE: 32

```
atactcaagc ttacaaaaca aaatgagtaa agaaagtggc aaatggtggg aaagtgatga     60
taaatttgct aaagctgtgt atcagcaatt tgtggaattt tatgaaaagg ttactggaac    120
agacttagag cttattcaaa tattaaaaga tcattataat atttctttag ataatcccct    180
agaaaaccca tcctctttgt ttgacttagt tgctcgtatt aaaaataacc ttaaaaactc    240
tccagactta tatagtcatc attttcaaag tcatggacag ttatctgacc acccccatgc    300
cttatcatcc agtagcagtc atgcagaacc tagaggagaa gatgcagtat tatctagtga    360
agacttacac aagcctgggc aagttagcgt acaactaccc ggtactaact atgttgggcc    420
tggcaatgag ctacaagctg ggcccccgca aagtgctgtt gacagtgctg caaggattca    480
tgactttagg tatagccaac tggctaagtt gggaataaat ccatatactc attggactgt    540
agcagatgaa gagcttttaa aaaatataaa aaatgaaact gggtttcaag cacaagtagt    600
aaaagactac tttactttaa aaggtgcagc tgcccctgtg gcccattttc aaggaagttt    660
gccggaagtt cccgcttaca acgcctcaga aaaataccca agcatgactt cagttaattc    720
tgcagaagcc agcactggtg caggaggggg gggcagtaat cctgtgaaaa gcatgtggag    780
tgagggggcc acttttagtg ccaactctgt aacttgtaca ttttccagac aatttttaat    840
tccatatgac ccagagcacc attataaggt gttttctccc gcagcaagta gctgccacaa    900
tgccagtgga aaggaggcaa aggtttgcac cattagtccc ataatgggat actcaacccc    960
atggagatat ttagatttta atgctttaaa tttatttttt tcacctttag agtttcagca   1020
cttaattgaa aattatggaa gtatagctcc tgatgcttta actgtaacca tatcagaaat   1080
tgctgttaag gatgttacaa acaaaactgg agggggggtg caggttactg acagcactac   1140
agggcgccta tgcatgttag tagaccatga atataagtac ccatatgtgt tagggcaagg   1200
tcaagatact ttagccccag aacttcctat ttgggtatac tttcccccctc aatacgctta   1260
cttaacagta ggagatgtta acacacaagg aatttctgga gacagcaaaa aattggcaag   1320
tgaagaatca gcattttatg ttttggaaca cagttctttt cagcttttag gtacaggagg   1380
tacagcaact atgtcttata agtttcctcc agtgccccca gaaaatttag agggctgcag   1440
tcaacacttt tatgaaatgt acaacccctt atacggatcc cgcttagggg ttcctgacac   1500
attaggaggt gacccaaaat ttagatcttt aacacatgaa gaccatgcaa ttcagcccca   1560
aaacttcatg ccagggccac tagtaaactc agtgtctaca aaggagggag acagctctag   1620
tactggagct ggaaaagcct taacaggcct tagcacaggt acctctcaaa acactagaat   1680
atccttacgc cctgggccag tgtctcagcc gtaccaccac tgggacacag ataaatatgt   1740
```

-continued

```
cacaggaata aatgccattt ctcatggtca gaccacttat ggtaacgctg aagacaaaga   1800

gtatcagcaa ggagtgggta gatttccaaa tgaaaaagaa cagctaaaac agttacaggg   1860

tttaaacatg cacacctact ttcccaataa aggaacccag caatatacag atcaaattga   1920

gcgcccccta atggtgggtt ctgtatggaa cagaagagcc cttcactatg aaagccagct   1980

gtggagtaaa attccaaatt tagatgacag ttttaaaact cagtttgcag ccttaggagg   2040

atggggtttg catcagccac ctcctcaaat attcttaaaa atattaccac aaagtgggcc   2100

aattggaggt attaaatcaa tgggaattac taccttagtt cagtatgccg tgggaattat   2160

gacagtaacc atgacattta aattggggcc ccgtaaagct acgggacggt ggaatcctca   2220

acctggagtg tatcccccgc acgcagcagg tcatttacca tatgtactat atgaccccac   2280

agctacagat gcaaaacaac accacagaca tggatatgaa aagcctgaag aattgtggac   2340

agccaaaagc cgtgtgcacc cattgtaagt cgacatactc                         2380
```

<210> SEQ ID NO 33
<211> LENGTH: 781
<212> TYPE: PRT
<213> ORGANISM: Artificial Sequence
<220> FEATURE:
<223> OTHER INFORMATION: Description of Artificial Sequence: VP1
      amino acid from parvovirus B19 clone 2-B6

<400> SEQUENCE: 33

```
Met Ser Lys Glu Ser Gly Lys Trp Trp Glu Ser Asp Asp Lys Phe Ala
  1               5                  10                  15

Lys Ala Val Tyr Gln Gln Phe Val Glu Phe Tyr Glu Lys Val Thr Gly
             20                  25                  30

Thr Asp Leu Glu Leu Ile Gln Ile Leu Lys Asp His Tyr Asn Ile Ser
         35                  40                  45

Leu Asp Asn Pro Leu Glu Asn Pro Ser Ser Leu Phe Asp Leu Val Ala
     50                  55                  60

Arg Ile Lys Asn Asn Leu Lys Asn Ser Pro Asp Leu Tyr Ser His His
 65                  70                  75                  80

Phe Gln Ser His Gly Gln Leu Ser Asp His Pro His Ala Leu Ser Ser
                 85                  90                  95

Ser Ser Ser His Ala Glu Pro Arg Gly Glu Asp Ala Val Leu Ser Ser
            100                 105                 110

Glu Asp Leu His Lys Pro Gly Gln Val Ser Val Gln Leu Pro Gly Thr
        115                 120                 125

Asn Tyr Val Gly Pro Gly Asn Glu Leu Gln Ala Gly Pro Pro Gln Ser
    130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser Met Thr Ser Val Asn Ser Ala Glu Ala Ser Thr Gly Ala
225                 230                 235                 240
```

-continued

```
Gly Gly Gly Gly Ser Asn Pro Val Lys Ser Met Trp Ser Glu Gly Ala
                245                 250                 255

Thr Phe Ser Ala Asn Ser Val Thr Cys Thr Phe Ser Arg Gln Phe Leu
            260                 265                 270

Ile Pro Tyr Asp Pro Glu His His Tyr Lys Val Phe Ser Pro Ala Ala
        275                 280                 285

Ser Ser Cys His Asn Ala Ser Gly Lys Glu Ala Lys Val Cys Thr Ile
    290                 295                 300

Ser Pro Ile Met Gly Tyr Ser Thr Pro Trp Arg Tyr Leu Asp Phe Asn
305                 310                 315                 320

Ala Leu Asn Leu Phe Glu Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asn Lys Thr Gly Gly Gly Val Gln Val
        355                 360                 365

Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Asp Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Gln Leu
        435                 440                 445

Leu Gly Thr Gly Gly Thr Ala Thr Met Ser Tyr Lys Phe Pro Pro Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Val Asn Ser Val Ser Thr Lys Glu
        515                 520                 525

Gly Asp Ser Ser Ser Thr Gly Ala Gly Lys Ala Leu Thr Gly Leu Ser
    530                 535                 540

Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575

Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Met His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
```

-continued

```
            660                 665                 670

Gly Trp Gly Leu His Gln Pro Pro Pro Gln Ile Phe Leu Lys Ile Leu
        675                 680                 685

Pro Gln Ser Gly Pro Ile Gly Gly Ile Lys Ser Met Gly Ile Thr Thr
    690                 695                 700

Leu Val Gln Tyr Ala Val Gly Ile Met Thr Val Thr Met Thr Phe Lys
705                 710                 715                 720

Leu Gly Pro Arg Lys Ala Thr Gly Arg Trp Asn Pro Gln Pro Gly Val
                725                 730                 735

Tyr Pro Pro His Ala Ala Gly His Leu Pro Tyr Val Leu Tyr Asp Pro
            740                 745                 750

Thr Ala Thr Asp Ala Lys Gln His His Arg His Gly Tyr Glu Lys Pro
        755                 760                 765

Glu Glu Leu Trp Thr Ala Lys Ser Arg Val His Pro Leu
    770                 775                 780


<210> SEQ ID NO 34
<211> LENGTH: 1699
<212> TYPE: DNA
<213> ORGANISM: Artificial Sequence
<220> FEATURE:
<223> OTHER INFORMATION: Description of Artificial Sequence: VP2 from
      parvovirus B19 clone 2-B6

<400> SEQUENCE: 34

atactcaagc ttacaaaaca aaatgacttc agttaattct gcagaagcca gcactggtgc     60

aggagggggg ggcagtaatc ctgtgaaaag catgtggagt gagggggcca cttttagtgc    120

caactctgta acttgtacat tttccagaca atttttaatt ccatatgacc cagagcacca    180

ttataaggtg ttttctcccg cagcaagtag ctgccacaat gccagtggaa aggaggcaaa    240

ggtttgcacc attagtccca taatgggata ctcaacccca tggagatatt tagattttaa    300

tgctttaaat ttattttttt cacctttaga gtttcagcac ttaattgaaa attatggaag    360

tatagctcct gatgctttaa ctgtaaccat atcagaaatt gctgttaagg atgttacaaa    420

caaaactgga ggggggggtgc aggttactga cagcactaca gggcgcctat gcatgttagt    480

agaccatgaa tataagtacc catatgtgtt agggcaaggt caagatactt tagccccaga    540

acttcctatt tgggtatact ttccccctca atacgcttac ttaacagtag gagatgttaa    600

cacacaagga atttctggag acagcaaaaa attggcaagt gaagaatcag cattttatgt    660

tttggaacac agttcttttc agcttttagg tacaggaggt acagcaacta tgtcttataa    720

gtttcctcca gtgcccccag aaaatttaga gggctgcagt caacactttt atgaaatgta    780

caaccccta tacggatccc gcttaggggt tcctgacaca ttaggaggtg acccaaaatt    840

tagatcttta acacatgaag accatgcaat tcagccccaa aacttcatgc cagggccact    900

agtaaactca gtgtctacaa aggagggaga cagctctagt actggagctg gaaaagcctt    960

aacaggcctt agcacaggta cctctcaaaa cactagaata tccttacgcc ctgggccagt   1020

gtctcagccg taccaccact gggacacaga taaatatgtc acaggaataa atgccatttc   1080

tcatggtcag accacttatg gtaacgctga agacaaagag tatcagcaag gagtgggtag   1140

atttccaaat gaaaaagaac agctaaaaca gttacagggt ttaaacatgc acacctactt   1200

tcccaataaa ggaacccagc aatatacaga tcaaattgag cgccccctaa tggtgggttc   1260

tgtatggaac agaagagccc ttcactatga aagccagctg tggagtaaaa ttccaaattt   1320

agatgacagt tttaaaactc agtttgcagc cttaggagga tggggtttgc atcagccacc   1380
```

-continued

```
tcctcaaata tttttaaaaa tattaccaca aagtgggcca attggaggta ttaaatcaat   1440

gggaattact accttagttc agtatgccgt gggaattatg acagtaacca tgacatttaa   1500

attggggccc cgtaaagcta cgggacggtg gaatcctcaa cctggagtgt atccccccgca   1560

cgcagcaggt catttaccat atgtactata tgaccccaca gctacagatg caaaacaaca   1620

ccacagacat ggatatgaaa agcctgaaga attgtggaca gccaaaagcc gtgtgcaccc   1680

attgtaagtc gacatactc                                                 1699


<210> SEQ ID NO 35
<211> LENGTH: 554
<212> TYPE: PRT
<213> ORGANISM: Artificial Sequence
<220> FEATURE:
<223> OTHER INFORMATION: Description of Artificial Sequence: VP2 amino
      acid from parvovirus B19 clone 2-B6

<400> SEQUENCE: 35

Met Thr Ser Val Asn Ser Ala Glu Ala Ser Thr Gly Ala Gly Gly Gly
  1               5                  10                  15

Gly Ser Asn Pro Val Lys Ser Met Trp Ser Glu Gly Ala Thr Phe Ser
             20                  25                  30

Ala Asn Ser Val Thr Cys Thr Phe Ser Arg Gln Phe Leu Ile Pro Tyr
         35                  40                  45

Asp Pro Glu His His Tyr Lys Val Phe Ser Pro Ala Ala Ser Ser Cys
     50                  55                  60

His Asn Ala Ser Gly Lys Glu Ala Lys Val Cys Thr Ile Ser Pro Ile
 65                  70                  75                  80

Met Gly Tyr Ser Thr Pro Trp Arg Tyr Leu Asp Phe Asn Ala Leu Asn
                 85                  90                  95

Leu Phe Phe Ser Pro Leu Glu Phe Gln His Leu Ile Glu Asn Tyr Gly
            100                 105                 110

Ser Ile Ala Pro Asp Ala Leu Thr Val Thr Ile Ser Glu Ile Ala Val
        115                 120                 125

Lys Asp Val Thr Asn Lys Thr Gly Gly Gly Val Gln Val Thr Asp Ser
    130                 135                 140

Thr Thr Gly Arg Leu Cys Met Leu Val Asp His Glu Tyr Lys Tyr Pro
145                 150                 155                 160

Tyr Val Leu Gly Gln Gly Gln Asp Thr Leu Ala Pro Glu Leu Pro Ile
                165                 170                 175

Trp Val Tyr Phe Pro Pro Gln Tyr Ala Tyr Leu Thr Val Gly Asp Val
            180                 185                 190

Asn Thr Gln Gly Ile Ser Gly Asp Ser Lys Lys Leu Ala Ser Glu Glu
        195                 200                 205

Ser Ala Phe Tyr Val Leu Glu His Ser Ser Phe Gln Leu Leu Gly Thr
    210                 215                 220

Gly Gly Thr Ala Thr Met Ser Tyr Lys Phe Pro Pro Val Pro Pro Glu
225                 230                 235                 240

Asn Leu Glu Gly Cys Ser Gln His Phe Tyr Glu Met Tyr Asn Pro Leu
                245                 250                 255

Tyr Gly Ser Arg Leu Gly Val Pro Asp Thr Leu Gly Gly Asp Pro Lys
            260                 265                 270

Phe Arg Ser Leu Thr His Glu Asp His Ala Ile Gln Pro Gln Asn Phe
        275                 280                 285

Met Pro Gly Pro Leu Val Asn Ser Val Ser Thr Lys Glu Gly Asp Ser
```

-continued

```
290                 295                 300

Ser Ser Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
    370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
        435                 440                 445

Leu His Gln Pro Pro Pro Gln Ile Phe Leu Lys Ile Leu Pro Gln Ser
    450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
        515                 520                 525

Asp Ala Lys Gln His His Arg His Gly Tyr Glu Lys Pro Glu Glu Leu
    530                 535                 540

Trp Thr Ala Lys Ser Arg Val His Pro Leu
545                 550


<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:  primer
      VP-5

<400> SEQUENCE: 36

aggaagtttg ccggaagttc                                              20


<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:  primer
      VP-3

<400> SEQUENCE: 37

gtgctgaaac tctaaaggtg                                              20


<210> SEQ ID NO 38
<211> LENGTH: 24
```

-continued

<212> TYPE: DNA
<213> ORGANISM: Artificial Sequence
<220> FEATURE:
<223> OTHER INFORMATION: Description of Artificial Sequence: primer VP2-5

<400> SEQUENCE: 38
gacatggata tgaaaagcct gaag 24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: primer VP2-3

<400> SEQUENCE: 39
gttgttcata tctggttaag tact 24

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: primer K-1sp

<400> SEQUENCE: 40
ataaatccat atactcatt 19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: primer K-2sp

<400> SEQUENCE: 41
ctaaagtatc ctgaccttg 19

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: primer Hicks-5

<400> SEQUENCE: 42
cccgccttat gcaaatgggc ag 22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: primer Hicks-3

<400> SEQUENCE: 43
ttgtgttagg ctgtcttata gg 22

<210> SEQ ID NO 44
<211> LENGTH: 54
<212> TYPE: DNA

-continued

<213> ORGANISM: Artificial Sequence
<220> FEATURE:
<223> OTHER INFORMATION: Description of Artificial Sequence: primer
NS1-5

<400> SEQUENCE: 44
atactctcta gacaaaacaa aatggagcta tttagagggg tgcttcaagt ttct 54

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: primer
NS1-3

<400> SEQUENCE: 45
gagtatgtcg acttactcat aatctacaaa gctttgcaat ccagacag 48

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: primer
VP1-5SN

<400> SEQUENCE: 46
atactcaagc ttacaaaaca aaatgagtaa agaaagtggc aaatggtggg aaagt 55

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: primer
VPALL-3

<400> SEQUENCE: 47
gagtatgtcg acttacaatg ggtgcacacg gcttttggct gtccacaatt c 51

<210> SEQ ID NO 48
<211> LENGTH: 55
<212> TYPE: DNA
<213> ORGANISM: Artificial Sequence
<220> FEATURE:
<223> OTHER INFORMATION: Description of Artificial Sequence: primer
VP2-5SN

<400> SEQUENCE: 48
atactcaagc ttacaaaaca aaatgacttc agttaattct gcagaagcca gcact 55

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: VSPC1

<400> SEQUENCE: 49
aaaaaaaaaa aaaaaaaaaa atccttaaca gcaatttctg ata 43

<210> SEQ ID NO 50
<211> LENGTH: 39
<212> TYPE: DNA
<213> ORGANISM: Artificial Sequence
<220> FEATURE:

-continued

<223> OTHER INFORMATION: Description of Artificial Sequence: VSPC2

<400> SEQUENCE: 50
aaaaaaaaaa aaaaaaaaaa cgccctgtag tgctgtcag 39

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: VSPC3

<400> SEQUENCE: 51
aaaaaaaaaa aaaaaaaaaa tatacccaaa taggaagttc tg 42

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: VSPC4

<400> SEQUENCE: 52
aaaaaaaaaa aaaaaaaaaa taaaatgctg attcttcact tgc 43

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: VSPC5

<400> SEQUENCE: 53
aaaaaaaaaa aaaaaaaaaa tgctgtacct cctgtaccta 40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: VSPC6

<400> SEQUENCE: 54
aaaaaaaaaa aaaaaaaaaa agccctctaa attttctggg 40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: VSPC7

<400> SEQUENCE: 55
aaaaaaaaaa aaaaaaaaaa ctcctaatgt gtcaggaacc 40

<210> SEQ ID NO 56
<211> LENGTH: 51
<212> TYPE: DNA
<213> ORGANISM: Artificial Sequence
<220> FEATURE:
<223> OTHER INFORMATION: Description of Artificial Sequence: primer
VSA1

<400> SEQUENCE: 56
aattctaata cgactcacta tagggagaag gccatatact cattggactg t 51

-continued

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence: primer VSA2

<400> SEQUENCE: 57
aattctaata cgactcacta tagggagaag gccagagcac cattataa 48

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: primer VSA3

<400> SEQUENCE: 58
aattctaata cgactcacta tagggagaag gcacaatgcc agtggaaa 48

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: primer VSP2

<400> SEQUENCE: 59
gtgctgaaac tctaaaggt 19

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: primer VSP1

<400> SEQUENCE: 60
ggaggcaaag gtttgca 17

<210> SEQ ID NO 61
<211> LENGTH: 20
<212> TYPE: DNA
<213> ORGANISM: Artificial Sequence
<220> FEATURE:
<221> NAME/KEY: misc_feature
<222> LOCATION: (1)
<223> OTHER INFORMATION: where 'c' is modified 5' with fluorescein phosphoramidite
<220> FEATURE:
<221> NAME/KEY: misc_feature
<222> LOCATION: (20)
<223> OTHER INFORMATION: where 't' is modified 3' with DABCYL
<220> FEATURE:
<223> OTHER INFORMATION: Description of Artificial Sequence: primer VSPPR1

<400> SEQUENCE: 61
cccatggaga tatttagatt 20

<210> SEQ ID NO 62
<211> LENGTH: 700
<212> TYPE: DNA
<213> ORGANISM: Artificial Sequence -continued
<220> FEATURE:
<223> OTHER INFORMATION: Description of Artificial Sequence: isolate
      CH80-1

<400> SEQUENCE: 62
ataaatccat atactcattg gactgtagca gatgaagagc ttttaaaaaa tataaaaaat     60
gaaactgggt ttcaagcaca agtagtaaaa gactacttta ctttaaaagg tgcagctgcc    120
cctgtggccc attttcaagg aagtttgccg gaagttcccg cttacaacgc ctcagaaaaa    180
tacccaagca tgacttcagt taattctgca gaagccagca ctggtgcagg aggggggggc    240
agtaatcctg ttaaaagcat gtggagtgag gggcccactt ttagtgccaa ctctgtaact    300
tgtacatttt ccagacagtt tttaattcca tatgacccag agcaccatta taaggtgttt    360
tctcccgcag caagtagctg ccacaatgcc agtggaaagg aggcaaaggt ttgcaccatt    420
agtcccataa tgggatactc aaccccatgg agatatttag attttaatgc tttaaatttg    480
tttttttcac ctttagagtt tcagcattta attgaaaact atggaagtat agctcctgat    540
gctttaactg taaccatatc agaaattgct gttaaggatg ttacagacaa aactggaggg    600
ggagtacaag ttactgacag cactaccggg cgcctatgca tgttagtaga ccatgaatac    660
aagtacccat atgtgttagg gcaaggtcag gatactttag                         700

<210> SEQ ID NO 63
<211> LENGTH: 700
<212> TYPE: DNA
<213> ORGANISM: Artificial Sequence
<220> FEATURE:
<223> OTHER INFORMATION: Description of Artificial Sequence: isolate
      CH81-3

<400> SEQUENCE: 63
ataaatccat atactcattg gactgtagca gatgaagagc ttttaaaaaa tataaaaaat     60
gaaactgggt ttcaagcaca agtagtaaaa gactacttta ctttaaaagg tgcagctgcc    120
cctgtggccc attttcaagg aagtttgccg gaagttcccg cttacaacgc ctcagaaaaa    180
tacccaagca tgacttcagt taattctgca gaagccagca ctggtgcagg aggggggggc    240
agtaatcctg ttaaaagcat gtggagtgag gggcccactt ttagtgccaa ctctgtaact    300
tgtacatttt ccagacagtt tttaattcca tatgacccag agcaccatta taaggtgttt    360
tcgcccgcag caagtagctg ccacaatgcc agtggaaagg aggcaaaggt ttgcaccatt    420
agtcccataa tgggatactc aaccccatgg agatacttag attttaatgc tttaaattta    480
tttttttcac ctttagagtt tcagcactta attgaaaatt atggaagtat agctcctgat    540
gctttaactg taaccatatc agaaattgct gttaaggatg ttacggacaa aactggaggg    600
ggggtgcagg ttactgacag cactacaggg cgcctatgca tgttagtaga ccatgaatac    660
aagtacccat atgtgttagg gcaaggtcag gatactttag                         700

<210> SEQ ID NO 64
<211> LENGTH: 700
<212> TYPE: DNA
<213> ORGANISM: Artificial Sequence
<220> FEATURE:
<223> OTHER INFORMATION: Description of Artificial Sequence: isolate
      B19SCL1-4

<400> SEQUENCE: 64
ataaatccat atactcattg gactgtagca gatgaagagc ttttaaaaaa tataaaaaat     60
gaaactgggt ttcaagcaca agtagtaaaa gactacttta ctttaaaagg tgcagctgcc    120

-continued

```
cctgtggccc attttcaagg aagtttgccg gaagttcccg cttacaacgc ctcagaaaaa    180

tacccaagca tgacttcagt taattctgca gaagccagca ctggtgcagg agggggggc     240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                           700
```

```
<210> SEQ ID NO 65
<211> LENGTH: 700
<212> TYPE: DNA
<213> ORGANISM: Artificial Sequence
<220> FEATURE:
<223> OTHER INFORMATION: Description of Artificial Sequence: isolate
      B19SCL2-1

<400> SEQUENCE: 65

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg agggggggc     240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                           700
```

```
<210> SEQ ID NO 66
<211> LENGTH: 700
<212> TYPE: DNA
<213> ORGANISM: Artificial Sequence
<220> FEATURE:
<223> OTHER INFORMATION: Description of Artificial Sequence: isolate
      B19SCL3-1

<400> SEQUENCE: 66

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg agggggggc     240

agtaatcctg tgaaaagcat gtggagtgag ggggccactt ttagtgccaa ctctgtaact    300

tgtacatttt ccagacaatt tttaattcca tatgacccag agcaccatta taaggtgttt    360
```

-continued

```
tctcccgcag caagtagctg ccacaatgcc agtggaaagg aggcaaaggt ttgcaccatt    420

agtcccataa tgggatactc aaccccatgg agatatttag attttaatgc tttaaattta    480

ttttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                          700
```

```
<210> SEQ ID NO 67
<211> LENGTH: 700
<212> TYPE: DNA
<213> ORGANISM: Artificial Sequence
<220> FEATURE:
<223> OTHER INFORMATION: Description of Artificial Sequence: isolate
      B19SCL4-3

<400> SEQUENCE: 67

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

ttttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                          700


<210> SEQ ID NO 68
<211> LENGTH: 700
<212> TYPE: DNA
<213> ORGANISM: Artificial Sequence
<220> FEATURE:
<223> OTHER INFORMATION: Description of Artificial Sequence: isolate
      B19SCL5-2

<400> SEQUENCE: 68

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

ttttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660
```

-continued aagtacccat atgtgttagg gcaaggtcag gatactttag 700

<210> SEQ ID NO 69
<211> LENGTH: 700
<212> TYPE: DNA
<213> ORGANISM: Artificial Sequence
<220> FEATURE:
<223> OTHER INFORMATION: Description of Artificial Sequence: isolate B19SCL6-2

<400> SEQUENCE: 69
ataaatccat atactcattg gactgtagca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaaaaa 180
tacccaagca tgacttcagt taattctgca gaagccagca ctggtgcagg aggggggggc 240
agtaatcctg tgaaaagcat gtggagtgag gggccactt ttagtgccaa ctctgtaact 300
tgtacatttt ccagacaatt tttaattcca tatgacccag agcaccatta taaggtgttt 360
tctcccgcag caagtagctg ccacaatgcc agtggaaagg aggcaaaggt ttgcaccatt 420
agtcccataa tgggatactc aaccccatgg agatatttag attttaatgc tttaaattta 480 ttttttttcac ctttagagtt tcagcactta attgaaaatt atggaagtat agctcctgat 540
gctttaactg taaccatatc agaaattgct gttaaggatg ttacggacaa aactggaggg 600
ggggtgcagg ttactgacag cactacaggg cgcctatgca tgttagtaga ccatgaatat 660
aagtacccat atgtgttagg gcaaggtcag gatactttag 700

<210> SEQ ID NO 70
<211> LENGTH: 700
<212> TYPE: DNA
<213> ORGANISM: Artificial Sequence
<220> FEATURE:
<223> OTHER INFORMATION: Description of Artificial Sequence: isolate B19SCL7-3

<400> SEQUENCE: 70
ataaatccat atactcattg gactgtagca gatgaagagc ttttaaaaaa tataaaaaat 60
gaaactgggt ttcaagcaca agtagtaaaa gactacttta ctttaaaagg tgcagctgcc 120
cctgtggccc attttcaagg aagtttgccg gaagttcccg cttacaacgc ctcagaaaaa 180
tacccaagca tgacttcagt taattctgca gaagccagca ctggtgcagg aggggggggc 240
agtaatcctg tgaaaagcat gtggagtgag gggccactt ttagtgccaa ctctgtaact 300
tgtacatttt ccagacaatt tttaattcca tatgacccag agcaccatta taaggtgttt 360
tctcccgcag caagtagctg ccacaatgcc agtggaaagg aggcaaaggt ttgcaccatt 420
agtcccataa tgggatactc aaccccatgg agatatttag attttaatgc tttaaattta 480 ttttttttcac ctttagagtt tcagcactta attgaaaatt atggaagtat agctcctgat 540
gctttaactg taaccatatc agaaattgct gttaaggatg ttacggacaa aactggaggg 600
ggggtgcagg ttactgacag cactacaggg cgcctatgca tgttagtaga ccatgaatat 660
aagtacccat atgtgttagg gcaaggtcag gatactttag 700

<210> SEQ ID NO 71
<211> LENGTH: 700
<212> TYPE: DNA
<213> ORGANISM: Artificial Sequence -continued

```
<220> FEATURE:
<223> OTHER INFORMATION: Description of Artificial Sequence:  isolate
      B19SCL8-2

<400> SEQUENCE: 71

ataaatccat atactcattg gactgtagca gatgaagagc ttttaaaaaa tataaaaaat      60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag gttttaatgc tttaaattta    480

ttttttttcac ctttagagtt tcagcactta attgaaaatt atggaagtat agctcctgat   540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                         700

<210> SEQ ID NO 72
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL9-1

<400> SEQUENCE: 72

ataaatccat atactcattg gactgtagca gatgaagagc ttttaaaaaa tataaaaaat      60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcaat taattctgca gaagccagca ctggtgcagg aggggggggc    240

agtaatcctg tcaaaagcat gtggagtgag ggggccactt ttagtgccaa ctctgtaact    300

tgtacatttt ccagacagtt tttaattcca tatgacccag agcaccatta taaggtgttt    360

tctcccgcag ccagtagctg ccacaatgcc agtggaaagg aggcaaaggt ttgcaccatt    420

agtcccataa tgggatactc aaccccatgg agatatttag attttaatgc tttaaattta    480

ttttttttcac ctttagagtt tcagcactta attgaaaatt atggaagtat agctcctgat   540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                         700

<210> SEQ ID NO 73
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL9-9

<400> SEQUENCE: 73

ataaatccat atactcattg gactgtagca gatgaagagc ttttaaaaaa tataaaaaat      60

gaaactgggt ttcaagcaca agtagtaaaa gactacttta ctttaaaagg tgcagctgcc    120
```

-continued

```
cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                         700
```

```
<210> SEQ ID NO 74
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL10-2

<400> SEQUENCE: 74

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                         700
```

```
<210> SEQ ID NO 75
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL11-1

<400> SEQUENCE: 75

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360
```

-continued

```
tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttat                         700
```

<210> SEQ ID NO 76
<211> LENGTH: 700
<212> TYPE: DNA
<213> ORGANISM: Artificial Sequence
<220> FEATURE:
<223> OTHER INFORMATION: Description of Artificial Sequence: isolate B19SCL12-1

<400> SEQUENCE: 76

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tcaaaagcat gtggagtgag gggccactt ttagtgccaa ctctgtgact    300

tgtacatttt ccagacagtt tttaattcca tatgacccag agcaccatta taaggtgttt    360

tctcccgcag caagtagctg ccacaatgcc agtggaaagg aggcaaaggt ttgcaccatt    420

agtccgataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacagacaa aactggaggg    600

ggggtgcaag ttactgacag cagtacaggg cgcctatgca tgttagtaga ccatgaatac    660

aagtacccat atgtgttagg gcaaggtcag gatactttag                         700
```

<210> SEQ ID NO 77
<211> LENGTH: 700
<212> TYPE: DNA
<213> ORGANISM: Artificial Sequence
<220> FEATURE:
<223> OTHER INFORMATION: Description of Artificial Sequence: isolate B19SCL13-3

<400> SEQUENCE: 77

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtgcatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660
```

-continued

```
aagtacccat atgtgttagg gcaaggtcag gatactttag                        700


<210> SEQ ID NO 78
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL14-1

<400> SEQUENCE: 78

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                        700


<210> SEQ ID NO 79
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL15-3

<400> SEQUENCE: 79

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                        700


<210> SEQ ID NO 80
<211> LENGTH: 700
<212> TYPE: DNA
<213> ORGANISM: Artificial Sequence
<220> FEATURE:
```

-continued

<223> OTHER INFORMATION: Description of Artificial Sequence: isolate B19SCL16-2

<400> SEQUENCE: 80

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttat                          700
```

<210> SEQ ID NO 81
<211> LENGTH: 700
<212> TYPE: DNA
<213> ORGANISM: Artificial Sequence
<220> FEATURE:
<223> OTHER INFORMATION: Description of Artificial Sequence: isolate B19SCL17-1

<400> SEQUENCE: 81

```
ataaatccat atacttattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                          700
```

<210> SEQ ID NO 82
<211> LENGTH: 700
<212> TYPE: DNA
<213> ORGANISM: Artificial Sequence
<220> FEATURE:
<223> OTHER INFORMATION: Description of Artificial Sequence: isolate B19SCL18-1

<400> SEQUENCE: 82

```
ataaatccat atactcattg gactgtagca gatgaagagc ttttaaaaaa tataaaaaat     60

gaaactgggt ttcaagcaca agtagtaaaa gactacttta ctttaaaagg tgcagctgcc    120
```

-continued

```
cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                          700
```

```
<210> SEQ ID NO 83
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL19-1

<400> SEQUENCE: 83

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                          700
```

```
<210> SEQ ID NO 84
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL20-3

<400> SEQUENCE: 84

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag ggggccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420
```

-continued

```
agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                         700
```

```
<210> SEQ ID NO 85
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL21-3

<400> SEQUENCE: 85

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggccactt  ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                         700
```

```
<210> SEQ ID NO 86
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL22-11

<400> SEQUENCE: 86

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcggg aggggggggc    240

agtaatcctg tgaaaagcat gtggagtgag gggccactt  ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatttag attttaatgc tttaaattta    480

tttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660
```

-continued

```
aagtacccat atgtgttagg gcaaggtcag gatactttag                        700


<210> SEQ ID NO 87
<211> LENGTH: 700
<212> TYPE: DNA
<213> ORGANISM: Artificial Sequence
<220> FEATURE:
<223> OTHER INFORMATION: Description of Artificial Sequence:  isolate
      B19SCL2-14

<400> SEQUENCE: 87

ataaatccat atactcattg gactgtagca gatgaagagc ttttaaaaaa tataaaaaat     60

gaaactgggt ttcaagcaca agtagtaaaa gactacttta ctttaaaagg tgcagctgcc    120

cctgtggccc attttcaagg aagtttgccg gaagttcccg cttacaacgc ctcagaaaaa    180

tacccaagca tgacttcagt taattctgca gaagccagca ctggtgcagg aggggggggc    240

agtaatcctg tgaaaagcat gtggagtgag gggcccactt ttagtgccaa ctctgtaact    300

tgtacatttt ccagacaatt tttaattcca tatgacccag agcaccatta taaggtgttt    360

tctcccgcag caagtagctg ccacaatgcc agtggaaagg aggcaaaggt ttgcaccatt    420

agtcccataa tgggatactc aaccccatgg agatatctag attttaatgc tttaaattta    480

ttttttttcac ctttagagtt tcagcactta attgaaaatt atggaagtat agctcctgat    540

gctttaactg taaccatatc agaaattgct gttaaggatg ttacggacaa aactggaggg    600

ggggtgcagg ttactgacag cactacaggg cgcctatgca tgttagtaga ccatgaatat    660

aagtacccat atgtgttagg gcaaggtcag gatactttag                        700


<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence:  primer
      Vpara 8

<400> SEQUENCE: 88

tccatatgac ccagagcacc a                                               21


<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence:  primer
      Vpara 9

<400> SEQUENCE: 89

tttccactgg cattgtggc                                                  19


<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence:
      substitute sequence in the internal control

<400> SEQUENCE: 90

agctagacct gcatgtcact g                                               21


<210> SEQ ID NO 91
<211> LENGTH: 26
```

-continued

```
<212> TYPE: DNA
<213> ORGANISM: Artificial Sequence
<220> FEATURE:
<223> OTHER INFORMATION: Description of Artificial Sequence:
      target sequence

<400> SEQUENCE: 91

ctacttgctg cgggagaaaa acacct                                         26

<210> SEQ ID NO 92
<211> LENGTH: 681
<212> TYPE: DNA
<213> ORGANISM: Artificial Sequence
<220> FEATURE:
<223> OTHER INFORMATION: Description of Artificial Sequence: internal
      control

<400> SEQUENCE: 92

gaattcactt gtacattttc cagacaattt ttaattccat atgacccaga gcaccattat    60

acagtgacat gcaggtctag ctctgccaca atgccagtgg aaaggaggca aaggtttgca   120

ccattagtcc cataatggga tactcaaccc catggagata tttagatttt aatgctttaa   180

atttattttt ttcaccttta gagtttcagc acttaattga aaattatgga agtatagctc   240

ctgatgcttt aactgtaacc atatcagaaa ttgctgttaa ggatgttacg gacaaaactg   300

gagggggggt gcaggttact gacagcacta cagggcgcct atgcatgtta gtagaccatg   360

aatataagta cccatatgtg ttagggcaag gtcaagatac tttagcccca gaacttccta   420

tttgggtata ctttccccct caatacgctt acttaacagt aggagatgtt aacacacaag   480

gaatttctgg agacagcaaa aaattggcaa gtgaagaatc agcattttat gttttggaac   540

acagttcttt tcagctttta ggtacaggag gtacagcaac tatgtcttat aagtttcctc   600

cagtgccccc agaaaattta gagggctgca gtcaacactt ttatgaaatg tacaacccct   660

tatacggatc ccgctgtcga c                                            681

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: probe
      Vpara10

<400> SEQUENCE: 93

taaggtgtt ttctcccgca gcgagt                                         25
```